United States Patent
Palaniappan et al.

(10) Patent No.: US 9,631,195 B2
(45) Date of Patent: Apr. 25, 2017

(54) **IDENTIFICATION AND CHARACTERIZATION OF THE SPINACTIN BIOSYSNTHESIS GENE CLUSTER FROM SPINOSYN PRODUCING *SACCHAROPOLYSPORA SPINOSA***

(71) Applicant: Dow AgroSciences LLC, Indianapolis, IN (US)

(72) Inventors: Nadaraj Palaniappan, Carmel, IN (US); Paul Lewer, Indianapolis, IN (US); Paul Richard Graupner, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 69 days.

(21) Appl. No.: 13/713,586

(22) Filed: Dec. 13, 2012

(65) Prior Publication Data

US 2013/0172215 A1    Jul. 4, 2013

Related U.S. Application Data

(60) Provisional application No. 61/580,947, filed on Dec. 28, 2011.

(51) Int. Cl.
*C12N 15/74* (2006.01)
*C12P 19/62* (2006.01)
*C12N 15/52* (2006.01)

(52) U.S. Cl.
CPC ............ *C12N 15/74* (2013.01); *C12N 15/52* (2013.01); *C12P 19/62* (2013.01)

(58) Field of Classification Search
CPC .... A01N 43/22; A01N 2300/00; A01N 43/90; A01N 51/00; A01N 53/00; A01N 31/14; A01N 63/04; A01N 65/00; A01N 25/04; A01N 49/00; A61K 2300/00; A61K 31/7048; A61K 31/365; A61K 31/351; A61K 45/06; A61K 31/165; C12N 15/52; C12N 1/20; C12N 1/14; C12N 9/1048; C12N 9/1051; C12N 15/1027; C12N 15/1037; C12N 15/63; C12N 15/74; C12N 15/905; C12N 1/00
See application file for complete search history.

(56) References Cited

U.S. PATENT DOCUMENTS 5,227,295 A    7/1993  Baker

FOREIGN PATENT DOCUMENTS

WO    03070908 A2    8/2003
WO    2010149956 A1    12/2010

OTHER PUBLICATIONS

Extended European Search Report for EP application No. 12198936.2, dated Apr. 24, 2013.
Pan Yuanlong et al., Genome sequence of the Spinosyns-producing bacterium Saccharopolyspora spinosa NRRL 18395., Journal of Bateriology Jun. 2011, vol. 193, No. 12, pp. 3150-3151.
Broughton, Matsushima P., et al., Conjugal transfer of cosmid DNA from *Escherichia coli* to saccharopolyspora spinosa: effects of chromosomal insertions on macrolide A83543 production, Gene 1994, pp. 39-45, vol. 146, No. 1.
Challis, Gust B., et al., PCR-targeted streptomyces gene replacement identifies a protein domain needed for biosynthesis of the sesquiterpene soil odor geosmin, Proc Natl Acad Sci, pp. 1541-1546, vol. 100, No. 4.
Quadri et al.; Identification of a Mycobacterium tuberculosis gene cluster encoding the biosynthetic enzymes for assembly of the virulence-conferring siderophore mycobactin; Chemistry & Biology 1998, vol. 5, No. 11; 631-45.
Baba et al. (2006) Mol. Sys. Biol. 2;2006.0008.
Thanassi et al.; (2002) Nucleic Acids Res. 30(14):3152-62.

*Primary Examiner* — Mindy G Brown
(74) *Attorney, Agent, or Firm* — Yung H. Lee; Carl D. Corvin; Magleby Cataxinos & Greenwood

(57) ABSTRACT

This disclosure concerns methods for producing a spinosyn producing host cell that comprises modifying a nucleic acid molecule encoding for spinactin by introducing, mutating, deleting, replacing or inactivating a nucleic acid sequence encoding one or more activities of a polypeptide encoded by the nucleic acid molecule. Methods for producing a modified *Saccharopolyspora spinosa* organism or strain are also disclosed.

6 Claims, 6 Drawing Sheets

Contig 261 S. spinosa wt
32893 bp

SEQUENCE LISTING

```
<160> NUMBER OF SEQ ID NOS: 12

<210> SEQ ID NO 1
<211> LENGTH: 64118
<212> TYPE: DNA
<213> ORGANISM: Saccharopolyspora Spinosa

<400> SEQUENCE: 1
cgatttgacc ttcgcggaac gactcgcccg cgcgctgcac acacgcatgt ggacaacacg      60
agccgacgtg attcaaaccg tggacaaccg tgtccacgcc acccaggtca ccgtcgccga     120
agacggcacc ttggtgccga ccttcgtcaa cggcctgggc accgggcact ggcacctgct     180
gggctccgaa ggccaacacc tatggagatc cggcccggaa ctgggtaccg ccgtcacccg     240
ggacggctcg acaccccgc gttacaccga cggaacgcac cccgccccgg taatcagatg     300
ggcgggaagc aacagcggcc actctggaca acaggatgcc gaagcggaaa cggcgaagca     360
gactcggcgg cccgggatag agaaggatga gttgaacgag tgggtggagc gggctaagaa     420
cgagggcaag gccgaaacgg cagcggcagg actgaaatgg ttgaaaggac aggggggccgg    480 ggttaataac gaggtttggg ggaaggcatg gcttgctgcg gatgggaagg agaagcaggt     540
ccggcggcct ggggtagata aggagcggtt gaaggagtgg gttgagcggg ctaaaaacga     600 gggagggggtt acgtcggcag cggcaggact gaaatgggtg cgtgaaaagg ggatcgggggt   660 tgggaaaaac gtttggggggg acgcgtggct tgctgcgact gggaaggaga agcaggttcg     720
gcggtctggg gtagataagg agcggttgaa tgagtgggtt gtgcgggcta aaaacgaggg     780 agggccgag acggctgcgg caggactgca atgggtgcac ggacagggga tcgaggttaa     840
caaaaacgtt tgggggggatg catggcttgc tgcggctggg aaggagaagc gggttcggcg     900
gcctcagcta gataaggagc ggttgaatga gtgggttgtg cgggctaaac acgagggagg     960
ggccgagacg gctgcggcag gactgcaatg ggtgcgtgga cagcggttcg cggttaacac    1020
cgaggcttgg ctggatgcgt ggcgtgatgc ggccgggaag gagaagcagg ttcagcggcc    1080
tcagctagac aaggagcggt tgaatgagtg ggttgggcgg gctaaaaacg agggagggggc   1140 caagtcggct gcggcaggac tgcaatgggt gcacggacag gggttcgggg ttgacaaaaa    1200
cgtttgggcg gatgcgtggc gtgctgcggc tgggaaggag aagcaggttc ggcggcctgg    1260
ggtagataag gagcggttgt ttgagtgggt gttgcgggct caacaggagg aggggccga    1320 gacggttggg gcagggctgg aatgggtaaa tcggcagggg gtcggggttg agaaaaaggt    1380
ttggtcggag gcgtggcgtg gtcgtggggt tttggattac tggcctgctg attttgacgg    1440
```

```
tgacgaggat ccattcgtgt gggaaagggg tgttggtgag ggcgatgtcg ccggcgttct   1500
ggatgtgtcg ccggtggatt gggagaggtt taccgagttg gagggtcggc cggaggccga   1560
ggtggcgagg ttgcagtcgg ctgctgcgga gctggtgagt ccgctcttgt tcgctccgca   1620
gtttgtgggt gtgaagccgc cggagcgggt ggcgtttgat ttggtggtgg atcaggttgc   1680
gatcacgctg catcgagcct cgcgagatgg tctgcccgaa ctggaggccg gtgaggccgc   1740
gcggacgcgt gccgaagagc tggcggcaag ggtgcgcgag gtgggtttgg aaggcgcgcc   1800
ggatatgcgg cgcactgcct caccgccagc acgtggtgtt gaggatgtgt cgtcctctgt   1860
tgggggagtc gggcagcgcg aaccggtggc ggtgggggat gcggcctcgg aacgggggtc   1920
ggcggatgcg tatccgggtg agtcgcagcc tgggccgtcg acggtccagg ccaccgccca   1980
ccaggggtcg gctgcgggtg atgtggccgc ctccgggcag caggatgctg atgcgggaac   2040
ggcgaaacgg gttcagagcc ctgcgataga taaggagcgg ttgaaggagt gggttgtgct   2100
ggctcaacag gtgggagggg cggagacggt tgaggcagga ctggagtggg tgcatcggca   2160
ggggtttggg gttgataccg gggcttgggg ggaggcgtgg cgtggtcatg gggttctgga   2220
tcactggtct cctgattttg aggatgaggg ggatccattc tcgtgggagg ggtttgacgg   2280
tgttggtgag cgggatgtcg ccggcgatct ggatctgttg ccggtggatt gggagaggtt   2340
tgccgagtcg gagggttggt cggaggtcga ggtggcgagg ttgcagttgg ctgctgcgga   2400
gctggtgagt ccgctcttgt tcgctccgca gtttgtgggt gtgaagccgc cggagcgggt   2460
ggcgtttgat ttggtggtgg atcaggttgc agtcacgctg catcgagcct cgcgagatgg   2520
tctgcccgaa ccagaggccg ttgcggcggc gcggacgcat gctgaagagc tggcggcaag   2580
ggtgcgcgag gcgggtttgg aaggcgcgcc ggatatgcgg cgcactgcct caccgccagc   2640
gcgtggtgtt gaggatgctt cgtcgtctgt tgggggtgtc gggcagcgcg aaccggtggc   2700
ggtgggggat gcggcctcgg aacgggggtc ggcggaggtg tatccgggtg agtcgcaggc   2760
tgggccgtcg acggtccaga tcaccgccca ccaggggtcg gctgtgggtg atgtggccgc   2820
cgctgggcag caggatgctg atgcgggaaa ggcgaaacgg cggcctgcga tagataagga   2880
gcggttgaat gagtgggttg tgcgggctca agaggaggga ggggccagga cggctgcggc   2940
aggactgaga tggatgcgtg gacaggggct tgggcttgat agcaaggttt gggggggatgc   3000 gtggcgtgct gcgactggga aggagaagca ggttcagcgg cctggggtag atagggaccg   3060
gttgtatgag tgggttgtgc gggctcaaga ggagggaggg gccaggacgg ctgcggcagg   3120
actgcaatgg gcgcgtggaa aggggttcgg ggttaggaaa aacgtttggt cggaggcgtg   3180
gcgtgctgcg gctgggaagg agaagcaggt tcggcggcct ggggtagata aggagcggtt   3240
gtatgagtgg gttgtgcggg ctcaagagga gggaggggcc gagacggttg cggcaggact   3300
ggattgggtg catcggcagg ggttcggggt taacaaaaat gtttgggggg aggcgtggcg   3360
tgctgcggct gggaaggaga agcaggttca gcggcctggg gtagataagg agcggttgaa   3420 tgagtggg tt gtgcgggctc aagtggaggg aggggccgag acgattgagg caggactgga   3480
ttgggtgaat cggcagggg t tcggggttaa caaaaatgtt tgggggga gg cgtggcgtgg   3540 tcgtgggg tt ctggatcgct ggtctgctga tcttgaagat gaggggg at c cattctcgtg   3600 ggagggggcc gacggtgttg gtgagcggga tgttgccggc gatctggatt tgttgccgac   3660
ggattgggag aggtttgccg agttagcaca agccgggcac gatttctctc ccgtcgcaca   3720
cgatctgcac gacacgctgg accgtacgca caaggacctc cccagcgacg cccgttccac   3780
cgacgacgtc ggactgaccg caccgccgcc gtttccgcac gccgaaggac cggcacgggc   3840
```

```
ggagatctgg atgcagccgg gcagcgacgg ggtgaaaccg gtaccagaca cgatccagga    3900
ccgacgcccg aaacgagacg gcgcacgacg gcgcctggcc tggcccggta gtaggcgggc    3960
cgacgacacc gcccccacca ccgcatcggg ttcctcccac gcgatctcac gggcttcccg    4020
ggaagcccgt gagatcccca gtggggcggt tccgatcagg ccacaggaaa acaccgggca    4080
ggtcaccggg agggacggtt tcgctggttt ccttggtggg tacagcgacg accacgggat    4140
gggttcggtc gggctgtctg acgaaagcac tttcggtgac ccgtcaccgg aagctgcggc    4200
gtggccgggt gcggggcgtg tggtggggtc tgggttccgg tttgtgcggg gggtgaatca    4260
ggccaattac ttctttggtg atgcgcgttt tcgggtgaat tgcctggagg cgtgtgtggc    4320
gtttcataat tcggtgaagt tcggtcggca gttcgtggcg ggtccggccg gtgctgatcg    4380
ggatccggct cggttggagg tggcgttcgg ccggcaggcc cggcaggtgg aggctgtggc    4440
cggggttgag cggtatgtgc gtggcgggcc ggtgggggcg actgtgccgg tgctgtacca    4500
gcgacccgac ggcagcgcgc atgtgatcaa tgccggtgcgt accggcagca aagaccctgc    4560
tgggcgcggt gtggtcgtgt tgtgggatcc gcagcggggc gaggaagccg aggtagccga    4620
tgtttctgcg gtgacgggga tgtgggtgat cccggtgccg gaggcggaag cagcggggat    4680
ggtggtgttg ccgtccagtg gttccgggtt gcgtagccag ggctggggat ccgggttgcc    4740
caacgaggtg gcgggtccga agcgtcagcc cggtgcgtcc gggccggagg ccgggaaacc    4800
cggcgcgggc gcgaaaagga cacaggcgga gaccggtgag agttcgccgg gtgccaagcg    4860
gcggaagggg gcagcagccc cggctgggat tgacccgggg agtccgggca atggcgaggc    4920
tggggtgctc accccgaccg atcaggcaac acaacaggac gagcgggcga cggagcggaa    4980
agagaaaaag aaggcaaggg acgcgaagta tcgccaggcg agaagggccg aggccgatcg    5040
tgttgtggtg ttggaggagt tggaggggcg ggggcagttg actgaggagc aggcgacgga    5100
gctggcggag ctccagccga aggtgacgga gcggaagcag caaaagaagg aagagaacgc    5160
gaagcagtac aaggcgagaa aggctgccgc tgcgcgggtt gtggagttgg aggagttgga    5220
ggggcggggg gagttgactg aggagcaggc gacggagctg gcggcgctcc agccgaaggt    5280
ggcgcaacag acgcagcaaa cgaaggaaaa taacgcgaag cagtaccagg cgagaaaggc    5340
tgccgccgat cgtgttgcgg tgttggagga gttggcgggg cgggggagt tgactgagga    5400 gcaggcgacg gagctggcgg cgctcaagcc gaaggtagcg cagcggaagc agcaaaacga    5460
aggaaaagac cgcgaactat agccagggt taaaggctgc cgatcgtatt gcggtgttgg    5520
aggagttggc ggggcggggg ccgttgactg gggagcagga ggcggagctg gcggaactcc    5580
agcgcaaggc ggcgcagcgg aagcagcaaa agaaggaaaa gagcgcgagg cggtaccagg    5640
cgagaaaggc tgccgccgat cggggttgtgg tgttggagga gttggagggg cggggggagt    5700
tgactgagga gcaggcgacg gagctggcgg cgcttcagcc gaaggcgcag cagacgcaga    5760
aaacgaagaa agataacgcg aagtatcgcc aggcgggcaa ggctgctgcc gcgcgggttg    5820
cggtgttgga ggagttggcg gggaggggc cgttgactga ggagcaggcg acggagctgg    5880
cggcgctcca gccgaaggtg gcgcaacaga agcagcaaaa cagggcaaag taacgcgaag    5940
tatgctcagc gggtaaacgc tgctgccgat cgtgttgtgg tgttgaggag ttggcgggg    6000 cggggggagt tgactgagga gcaggcggcg gagctggcgg ggctccagcc gaaggcgcag    6060
cggaagcagc aaaggaaggc aagggacgtg aagtataacc aggcgagaag ggctgctgcc    6120
gatcgtgttg cggagttgga ggagttggcg gggcacgggc cgctgactga ggagcaggcg    6180
```

```
acggagctgg cgccgctccg gccgaaggca gcggggcggg ggcgagggcg gaagaagaag    6240
gaccgggagg tgatggagac cggggtgggt gaggccccgg tggcggggcg ggatgagcgg    6300 attgcgggc  cggaggggt  atcggagtgg actgggactg atcaggaagg tcggacgca     6360 tggtcggctg acttcgatct cggtgcgtgg cccgagcagg cggtggcggg ttcagcttgg    6420 tcgggggtg  tgggtgcggg agatgccggg gtgatgctgg gcgagggcgc tgtcgaggac    6480
gttctcgcga ccgagttgac cgcgttcctg gacaggatg  ccggagcgga tgatttcgcc    6540
ggattcctcc ccgactacca cgactgggac ggctccgttg ggttgttcgg ggccgaaggg    6600
cctgacaggg gacctttcgg tgacccattt ccggaaggtg cggtgtggcc gaatgaggtg    6660
gctgcggatc cggtgggtgg gatgggggcg tctgggtgt  gggcggattc cgaccgggat    6720
gcggacggcg cggtggggtc tgggttccgg tttgtgcggg gggtgaatca ggccagctac    6780
ttctttggtg atgcgcgttt tcgggtgaat tgcctggagg cgtgtgtggc gttccataat    6840
tcggtgaagt tcggtcggca gttcgtggcg ggcccggctg gtgatcggga tccggctcgg    6900
ttggaggcgg cgttcggccg gcaggccgg  cgggtggagg tgtggctgg  ggttgagcgg    6960 tatgtgcgtg gcgggccggt gggggtggct gtgccggtgc tgtaccagcg acccgacggg    7020
agcgcgcacg tgatcaatgc ggtgcgtacc gagagcaaag accctgctgg gcgcgatgtg    7080
gtcgtgttgt gggatccgca gcggggtgag gaagccgaga gagccgatgt ttcagcggtg    7140
accgggatgt gggtgatccc ggtgccgaaa gcggaggcgg aaccggacca ggggatggtg    7200
gtgttgccgt ccagtggttc cgggttgcgc agccagggct ggggctccgg gctgcccacc    7260
gaggtggcgg gtccgaagcg tcagcccggt gcgtccgggc cggcggccgg gaaaaccggc    7320
gcgggcgcga agaggacacg gggcgaggct gatgagagga catgggcgga gaccggtgag    7380
agttccgggg gggccaagcg gcggaaggtg gcagcagccg cagctgggat tgaccccggc    7440
attccgggca atggtgagag tgaggtgctc accccggccg atcaggcagc acaagaggcg    7500
gcgcagcaga gacagaaaaa gaaggaagag aacgcgaagt ttctccaggc gagaaaggcc    7560
aaagtcgctc ggtttgcgga gttggagaag ctgaaggggc aggggcagct gactgaggcg    7620
caggagacgg aactggcggc actccagccg aaggtggcgc attggaaaca gctagagaag    7680
gcaagaaacg cgaaggatca ccaggcgaga aaggctgctg ccgcccgtgt tgcggagttg    7740
gaggagttgg cagagcgggg gccgttgact gaggcgcagg cggcggagct ggcgaagctc    7800
cagccgaagg tggcgcagcg gaagcagcaa aagaaggaaa atagcgcgaa gcggtcccag    7860
gcgggaaagg ctgctaccgc ccgtgttgcg gagttggagg agttggcggg gcgggggag    7920 ttggctgagg cgcaggcggc ggagctggcg gagctccagc cgaaggtggc gcagcggaag    7980
cagcaaaaga aggaaaatag cgcgaagcgg tcccaggcgg gaaaggctgc taccgcccgt    8040
gttgcggagt tggaggagtt ggcggggcgg ggggagttgg ctgaggcgca ggcggcgag    8100 ctggcggagc tccagccgaa ggtgcgcag  cggaagcaga acagaaggaa aagaacgcg    8160 aagcggtccc aggcgggaaa ggctgctgcc gcccgggttg cggagttgaa ggatcaggag    8220
gagctgacta aggaggaggc ggcggagctg gcgaagctcg aggcggaggt ggcgaagcag    8280
agggaaaggt ggaggaaagc tagcgcgaag catcgcccgg cgaaaaaggc cgccgctgcc    8340
gccgcgattg cggagttgga ggcgttggag gagcagggga cgctgacttc ggagcagcag    8400
gccgagctca atttgcggcg ggaaataaaa atgaacgaaa ctgaggtaca tcgcctggta    8460
aaccaggtat cgctagggaa caatgccgct aaggaagtca aggcgctgga ggcgttgccg    8520
cggagtgttg agattgaggc caagctgcct acgttgcgga gcaaggtggc taggttggcc    8580
```

```
gcgtttgcgg agccgttgaa ggaaacgaaa caaaggcttg cggaaagcag gaagaagctc    8640
aagctgatgc aggaggctgg atcggggcgg attgcgggtt tggaggcaag tgggcagcag    8700
gatgagcaga gcgcaatggt ttcgagcggg gtatcggagt ggactggggc tgatcgggac    8760
gagcggggcc aggggatggc cgacttcgat ctcggtgcgt ggcttgatcg ggagctggcg    8820
gatttggatg tgtcgtggga tgcgggtccg gcggagcagc gtggggcgga acgggacgcg    8880
tggtcgggtg gggcgttga tctcggtgcg tcggttgatg aggcgatcga ggattcagct    8940
ggcgacgggc aggctgcggc atcgccgtcc actttggacg aaaatcggca gacggatttg    9000
gaggcgttgc gggagtcgga tgcggctatg cagacggagt gggggggagcc gcgagagggg    9060 ttggacgagg ctgatcaggg gcaggtggag ggtgcgatcc gcgatgcggc gcaggattcg    9120
cgggttgcgc agctgcggga gtcgctgaag caggctgagt ctgacctggc ttcgttggag    9180
gcgttgccgg gttgggacga gaacctgcgg gcggagttcg cgacgttgcc gatgttcgat    9240
cagggtttgc ggacggactg ggagcaggcg cagcggcgta tcgaggcgtt gcgggcggaa    9300
ttggccgaga tggtggatga cgcgggcgaa ccggccgggc aacacatggg tgagtctcgg    9360
gaggggcggc tgcggcatt cgtgccgact gagattgcga cgttggctga ggtgacgggt    9420
cggatggagc ggcatttgcg gacgatgccg ctggaattca atccgaatcg tgtgcgtgag    9480
aacgtcgaaa ctgcgaagca gtgggtgcag caggggcagt ggactccagc gcagttgcgg    9540
acggttgagt cgaggttgga ggcgatacat gcggcggaga gggcgttgct cgatgctcgc    9600
ctggcaatgg atgcgcaggc gataggcggg gctgagttgg gggctgggta tcggttcctg    9660 gaggggcga accgggccaa ttatctctct ggtgatgtgc gtttccaggt gaattgcctg    9720
gaggcgtttg tggcgtttca taattctctg aagttcaacc gggagtttgt ggcggggccg    9780
gccggtactg atcgggatcc ggctcggttg gaggtggcgt tcggccggtg ggcctggcgg    9840
gtgggtggtg tggctgaggt tgagcagtac gtggggagcg ggccggtggg cgttgctgtg    9900
ccggtgattt accagcgagc cgacggtagc gcgcatgtga tcgctgcggt gcatgccgga    9960
gaccgctatg ggcatcaggt ggtggatctg ctggatccgc ataagggga ggtcgctgag    10020 aaagctgatg tcttggctgc gaccgggatg tggatgattc cggtgccggt gccggtgccg    10080
gtgccggtgc cggtgccggt gccggtgccg gaccgggaga tggtggtctt gccgcccagt    10140
gggtccgggt tgcgcagcca cggctgggga tccggactgc ccaccgaggt gacgggtccg    10200
aagcgtcagc tcggtgcgtg gccggtgacc gggaaaaccg gcccgaaagg cacaaagagg    10260
acgcaggcgg aaggccgatg agagtgtgcg ggcggcggct ggcgagagtt ccggggccca    10320
ggtggcagca gcagcggctg ggattgatcc agggagtccg ggcaacggcg agagtgaggt    10380
gctcactccg accgatcagc cagcacaaca ggacgagcgg gcggcggagc ggagacagaa    10440
aaagaacgaa ttgaacgcga cgtatcgctg ggcgaaaagg gccgaagccg atcgggttgc    10500
ggtgttggaa gaagctcaag ctgatgcagg aggctgggtc gggtcggatt gcgggcgtgg    10560
tggcaagtgg gcagcaggat gcaatggtgc taggtgaggt ggggggagtgg actggggctg    10620 ggcagggcga acaggacgcg gggccggctg acgtcgatct cgatgggtgg catgatcgga    10680
cgttgcggga gttggatgag ggcagggcgg atgcggtgga gggcacggcg gatgctggcg    10740
tgatgcaggg cgaggatgct gcttacgagg agtttgtcgc gaccgcgttg accgcgttcc    10800
tgcgacagga tgctcgggag ggcgcggcgg atgctgtgga gtcgggcaat gaggcaatga    10860
gggctgggta tcggcacaca atcaggctgg aaaacccacc acagcgtgaa taatgcaggt    10920
```

```
atctccaagg atgcccgcca gcttcggcag aggcggatca tcgcgagtgt gatcatggtt    10980
tcggagttgg cggtcaggcg ttcgtcgtct cgtgcgaggc ggcgatgtcg gatcaggcac    11040
ccaaaaggtc gttcgaccac ccacctgcgc ggtaggccct ggaacccctt gacatcgtcg    11100
ctgcgtttga cgatttccag taccagtccg aggttttcct tcgcccaggc cggcaggccg    11160
ttgatgatgg agttggggtg tccggcatcg gtctggacca gcgcgatcgg gggaaccggg    11220
cggccaggtt ttgcaggatc tcccgccctc cgacgtggtc ctgtactgac gcggaggtga    11280
ccatgacggt cagtagcagg ccgagggcgt cggccgaggg tgtccacggt gaggtggcgt    11340
ttgcggcctg tcgtcttctt atcgaacccg tgtgcttcgc cgcgctcgct gctttcgatg    11400
gactgggcat ccagcaccgc cgccgtcagg tccgcctggt gcccggcctg gatacggacc    11460
tgatcgcgca gcgcgtcgtg aacacggtcg atggtgccct cgctgttgcg ctacgtgccc    11520
acctggttac ccaacagtct cttggcttgc ctctaaaaag ttaccctggt caaactggcc    11580
gctgtgtgat cacggaacgc cttgggtgat cattttctt gccaacaact caagcggcgc     11640
cggcatgacc ccgtcccggt gcaggggcag tggctggcca gtgtcttgcg agagcacacg    11700
gcctactacg ccgtaccagg caactccgat gcgtatcgac cttccgccat caggtgacca    11760
ggctctggca caaggcgctc cggcgccgaa gccggacatc cctggtgggt gtgtgaaccg    11820
cattgttgac cgcgaatgat cgccacgaac accaggatga tcgcctgcat cacgacagtg    11880
atgaggttct gcggctaggt cagtatgctc gccgcgaggt cgctgatcga gtggtaccag    11940
tggccagccc gtgtcactcc agcgcgcgaa ggttcggcac gacgtccacg acggagtccg    12000
gtaccagagt gccgcagccg ttgaaccgtc gcggcctgga ttacgtgtgg ctaccaaaac    12060
gctgatcgga gccccatcca tcggtgctgc agggcggaag gagtggtaga tggcgagctt    12120
attgtctcgt cggacgcaaa ccgctggcga tgatgcgctg atccggtcgc tgttcgagga    12180
gcacggtcgc gccctgctcg cttactcgac gcgactgacc ggcgatcgag cggcggccga    12240
ggacgtcgtg caggagacgc tggtacgagc gtggcgaaat cccaacgccc tggtgaacgg    12300
gaagggttcc gttcgcgggt ggttgctgac cgtggcgcgc aacatcgtca tcgaccgcag    12360
ccgcgcgaag gccgctcgtc caccggaggt cgcggccacg ccgacagcgc cgccggcagt    12420
gcgtgaccac gccgactccg tggtcgactc gatggtcgtc accgaggcgc tggatacgct    12480
ttcggaagac caccgcgacg tgctggtgca gatctacttc cgaggactca gcgtggctga    12540
ggcagccgct gaactggcaa taccgccggg aaccgtgaaa tcacgatcct actacgcctt    12600
gcgggcactt cgtgaagcgt tgggcggcgc agcgttggtc gcatggaaag aggtggctcg    12660
atgagcagcc aggatcacaa ggtcgacctg ggcgcctacg tgttgggcgt actcgacgaa    12720
ccggaacaca gcgcgctcga cgagcacctg acgtcctgcg gacactgccg tggggaactg    12780
gaggacttgg agcagatgcg ggccgtgctg gacgaggtcc cgccggagtt gttcctggac    12840
ggacctccgg acgacgcaga cctgctgttg cagcgcacct tgcggcaggt tcgttcggag    12900
aaatccaggg cgtatggcat caggcacgcc gtggtaggcg cggcggcggc tctcgtcgcg    12960
gccgtcgccc tcggcggcgg cgtgctgatc ggccgagcgg gtgacagcgc accgccgctg    13020
gtcgtcgcgc agccgccgat cgcgtccatg ccgcccgccg gaacgaaggc cgccacggcc    13080
gtcgactcgg ccagtggggc gaggctgact gtgacggtca cgcctgcagc tggctgggtg    13140
cggttgaacg ccgcggtcaa cgggataccg gcgggcgaac ggtgccgctt ggtcgtagtg    13200
ggcaaggacg gtagccggga gatcgctggt agctggctgg tgtccgagaa gggcgcgaac    13260
gaaggcagcg cgctggatgg ttcggcgctg atggcgccgg acgatgtggc ggccgtcgaa    13320
```

```
gtggagaact tcgagggcac cagattcgtc tccacggcgg tctgaccagg cgacatattc   13380
cgacgtcaag ccccgtcccg gaacatccgg ggcggggctt gctcaggccg cggcccggga   13440
gtgcgatgat ggctcggtgt ccacaagcca aagacagtct gggcgccggg cgtggcggct   13500
ggccgcagtt ctgctgccgg tcgggctcgt cgcggcgttg ggtgtcgggt acgtcgacgg   13560
gcacggtgtt catggcgctc cggggccggt gaccggcgat ttcgtcgaca tcgcagatgt   13620
tcccccgatg ggtccgcaaa accgttcgg ccccgacgcc tcgaccggcg tgatgacggt    13680
tgactgcggt cgtaacgaaa cgcccaccg caacgcggac aacgtcatcg catcgcctgc    13740
cgtgtccggc ggagcgcatc acatgcacga ttacgtgggc aacctggcaa cggatgcgtt   13800
cgccaccgac cagagcctcg ctgcagccga aaccacttgt gtgaacggcg acaggtccac   13860
ctactactgg ccagtgcttc gcctgctgaa cggcgacgag ccgggttccg ccgatatgcc   13920
gcacaaccgc ggcacgattc ttcaaccggc ctcagtactg ataagtttcc gcggcaatcc   13980
ggccagcaag gtgatcccga tgccccggtt cctgcgggcc gtcatcggcg acgcgaaggc   14040
gctcaccaac ggcttggaca acgccgcccg agtgcactgg acctgttccg gaatgctcga   14100
ccggcagacg aaccgctatc cgaggtgccc ggacgggcat cgagtggtcc gggtcttcga   14160
ctttccgagt tgttgggatg gcaggaggaa cgacagcccg aaccatcgcg atcacctggt   14220
gttcccggcg ggaaacgggg tatgcccgac caactcgttc gccgtcccgc agttgcgcat   14280
cgaagtcgac tacgacgtgc ccagcgacgc ggagtacgcc atcgacacct tccccgatca   14340
gcagcgcagc ccgatcacgg atcacagcga tttcataaac gtgatgaccg atgagcagat   14400
ggcacacgtc gtggccgtcg tgaacaacgg gcgcatcggc tgaggaagaa acctccgaaa   14460
tgaaaatggt cgtgagtgcg ttgtccgggc tccgcccggc aacgcactca cgaccattgg   14520
tcagcggtag gtcagccgaa gaacaccgac tccacggcat tgtcgaatcc gacctcgccg   14580
agatcggcga catcaccgtt gatgaccaac gacttgccgg tgcagttctg cccggaccac   14640
agcttcaagg acccggacgc cgaaatcgac gacgtcacgt cgcgccgcgc gacgttcttg   14700
cagcccggtc cggccacgcc ctgcgaagca ccgtcgtcgc tgaaattctt gtcgtcgaag   14760
agaaccgcgc tgtcggcgga ttcggtcggc tgcgtgctgc cgtcctgcgc atcgccgttg   14820
ccgtcaccgg tttcggtccc ggctttctgg ccgttcggag tgatcccgaa ccacgttccg   14880
cccacacctt ggcccttggc gtcgcccggc ttggtgtcct tggcgaagcg gtagaccggc   14940
cagccaccga tggtcacctg gaggctgccg tcgtcccgtt tgacggtgcc caccttggac   15000
ttcgaaacgc cggccaagaa gatcctgccg ccccgagcca cggtcaacgg cggccaggtc   15060
ttcgcgcaat ccccgttgca gttcgacacc gagggcttgg ccgtgtcctt gtcgaaccgg   15120
tacaacgtga gtccggcacc gttgaccact accgggtcca gagcacctgc ctgggaagcc   15180
ttcaactgca cccactttcg cgcaacattc tggtccgcgg tgttggctgt gccgtcggac   15240
ccggttgccc agtcccggt cttcgccgtc gcattgtgcg ccttggcggt cccgccagt    15300
aaggacaggc cggcgcttcc ggtctcgggg acctgcgcac tcggcgcggc aggcgccgga   15360
cccgccgcga aggtcggcaa cccgcacgcg ctcaacgaca ccgctccggc gacgacgagg   15420
acggcaacgt acttggctcg cttttgacagc atgagttctc ccctcaaatc ccgggctcca   15480
gccaatctgc agccacgtac ggcggaaaca cgtgccccga tccgcaccgg ttcaagagat   15540
cgctgaattt ttcggacgcc cgccgttgac tcgatggatg cgtatggtg atcgcgtcat    15600
gtctgtgagt gacatgtgga cagaggcggg atggacgccg gggcgctggg cagcggcgat   15660
```

```
caaccgcatc ttggcttcgg tgcgtgcggc ggcggctcgc gcattaggtg atcggcttgg    15720
ccgcacgatc accaaggacg atctttggtc gacgctgcgt tcagcaagta ctcgatctcc    15780
gtgagccagc acttcaacac gtccagcgtg gcgacgatcg gcggtctcct acggaccggc    15840
gtgggcgtgg cggctttgcc ggccttggag ttgcagggtt tcggtttgga ggatctcgtc    15900
gcggtacccg tggattcgcc gggagcgacc agggtcatcg gcgtggtgta ccactgctcc    15960
caggacctct cgcctgtcgc ggctcgtttt ctggacttca tgcgtgcgac cgagatcgat    16020
cccccgcgag gagtctcccg cggcctcgac ggcgacaccg gcgaaccaga cgcgatcaac    16080
tggcaccgta catgatcagc cagcgcgccg atgccggctt gttgcgcgcc gtgtgtccat    16140
ttcgtgcgga ctttccccgg tatgaaggcg ttcctgggca cgattccgct tccgcccgaa    16200
atctgtccaa ttgcgactct ccagcgaggc ttagtctctg cggttcctat tcctggtgcg    16260
ccaccagacc acgggagccc tcttgagccc tctacttcct ggcccgagtc accgaccccca   16320 gctgagccgg gggcctgctt agaggctccg gcaataggcc gggaaagttg attagaaccg    16380
caggtagaag tccgtgagcc cgttgggtgc tgcagaggcc gctgtagaac ccgttctgcc    16440
tagaggtttc ggtggcgatc ccaacggggcg cggtctcgtt ccgcctcccc aaccgatgtg    16500
aagcgaacgg cctgttcgct tcggtaggtg gcacgaacgg tccgttcgct tcgttcccct    16560
tggtgtgggt gccggggttg ccggtgtggg gcgaacggcc tgttcgcttc ggtaggtggc    16620
acgaacggtc cgttcgcttc aaacaacacg ccaaacgctg ctaccgcacc cagccgcgct    16680
cacggtttct gggcgggcgg gcgggcgggg ggcccggttc ttaccagggg actcgggtga    16740
gcttttccgg gttgacgatg tcgcagatct gcgtctcgct gcgttcgctg accagcggcg    16800
attagcgggc gccctaccag ggcgaccagt gctgcggcca cgtcgggaac cttgaacgac    16860
gccgcgggta cgccgccggt gatgtccgct gccgggctgg ccagagcccg tgtggtgccc    16920
cggcgtcgag ggcggcgtag cggtcgccat cgacgaattt cgttgccaga ccgaaagtgt    16980
tggcgtaaaa ctgcacggca gcgtcgacgt ccgccaccgg tgttgcgtg ttcccgattt     17040 tgattgggtc gatcttcgcg ggggcactca tcgggcgacc cgtagccggt tccttctgcg    17100
ccgtcgaggt gtgcagctcg gcacctccgc gacggaggat ccggggcagc agtgggggttt   17160 cgagcccgcg gctgctccag acttcggcac ctccgctcca gacttcggca cctccgcgtc    17220
cgttccttcc ggtgaataga ttcttgcgat agttgtggtg ccactcgcg ccgtacggcg     17280 cgaacgtggc ctcggcctcc cgctgcaccg tcagcgcggg ggttcttcac gaacccgttc    17340
ggcccctgca ccagcagcgc ggagccgctg accagcttgg tcgcctgctt gtaccgggtg    17400
agcgcttcgc aaaccaccgc gaaggcatcc acgtcccaag gcgtgagcac tccgaccgcc    17460
atcagattgg gcgccaaccg gtcccacgcc gcacgggcgt cctcggacgg ctccttcaac    17520
ggggtgacct cgccttcggg cgggatcggc tggttgatgc ggtcgtggcg gtcgccgtgc    17580
agcaccttca gcgcgcgatg gctttccgag ccccacaggc tcggggagtc aagccaaagc    17640
gcggcaagct ggtcgagccg ctgccggacc gccgggtggt cctaaaagtg caggagcagc    17700
acgggaccgc gctccagccc gccgtcctcg taggaggaca ggtgggcgga cacctcgtgg    17760
tggcggggaa gtcgagcggg ttccacgacc ggcggcgtcg cacacggcgt tcgcccttt     17820 gtgcagtgtt cgcggaagct cgtgcagcaa aggctttccg gggttgcccc ggtttgttcc    17880
cgcgaatatc acagttcaat gcgctggacg ttgccaacat atcgaacgga ggcgcctaaa    17940
tgcctctccc gcagtacccg cctcaccacg gccgccgtgc tcgccctcgc cgtgggcggc    18000
atgaccgcgt gcggtgacgg cggcgccact gaggcggccg caccgttcaa cgcgtcgttc    18060
```

```
tgcgccgagc tccgcaagag ccacccggaa ctcgtcgggg ccgagctgaa ggtcggcacg    18120
accgttgggc agggcaactt cgaattcatc acccccgacg agccggatgt ggtgaagggc    18180
ctcgaccccg acctggtgag ccttgtgggc gactgcctcg gcttccgctc cacgttcgcc    18240
cagatggagt tcaccggcct ggtgcccgcg ctccagtccg gacgcgtgga cctcgtcgcg    18300
tcgaacctct acgtgaccga ggaacgcgcg cggaaggtcg acttcgtcac ctacctgaag    18360
acgatgagtg ccgtcgtcac gcagaagggg aacccgagga agctcacgag cgccgacgcg    18420
ctgtgcggca ccacggccgc gcaggtcgcc ggaaccgtcg agagcgagat catcgagaag    18480
cagtcgcagt catgcgagcg gtccggccgc gccgggatca caccgctggt cttctccgcg    18540
ctggaccagg ccgtcgccgc gaccaccacc ggccgcgccg acttcttcat gaacgacgcg    18600
ggcatcgcga agtcagccgt tgagaagtcc cccgaacacc tcgaccacgg tttcttggtc    18660
gacaccaacc tcgtcatggg catcgccacg aacaagaaca agagcgagct ccgcgacgcc    18720
gttcacgagg tgctggtgcg tgccgaggcg acggtgcgc tgcgcgagct ccagcggaag    18780
tggggcttcg gcgagaatca gctcatcgcc ccccagatcg tggcctgacg gaggttcccg    18840
tgccgtcctt ctggcactac ttcctgctgc cgtcgatgtg gcagggcctg ttcaccgggc    18900
tgaagatcgc cgccgtcgcg ttcgctgcgg gtctggtgct cgggctcgcg ctggccgtcg    18960
cccgcgacgc cgcgctgggc gtcgtccgcc tgatgagtgc gggctacgtg tggctgttcc    19020
gcggtacgcc aatcctgctg cagctggtct tcctgttcaa cttcctcccc gccgtcggga    19080
tcgggctgcc gccgctgcag accgcgatgc tcggcttcgc gctcaacgag gccgggtact    19140
gcaccgagat cttccgtggc agcctccggt cggtgagccg gacgcagacg acggccgcgg    19200
cgtcgctcgg gatgggccgg tggctcacgc tctcgcgcat cgtcctgccg caggcactca    19260
aggccgccat cccggcgctc ggtaacgagg cgatctcgct cgtgaaactt acctccatcg    19320
cgtcagcgat ctcggtcacc gagctgacat tccgcagcca gcagatcgtc gccaccaact    19380
tcgaggtcgt gcccgtatac ggcgtggcag ccgtgatgta cctgctcgtc atcacggcga    19440
tgaccgccgc gcagtccgcg ctggaacgtc gattcggcgc tccggccgac cgtccgtcgg    19500
cccgggcgcg cctcttcgcg ttccgcagcc ggacgcgcct tccgcgcgcc gggcgctcag    19560
cggtgccggt tgccggggtc gaccgctccg gccgcgacaa cgcgttcctc tcgatccgca    19620
acgtctccaa gcgcttcggc gaccgcgagg tgctgcggga cgtaagcctc gacgcccggc    19680
gcggcgaggt tctcgtgctg accggtcgca gcgggtcggg caagagcacc ctgctgcacc    19740
tggttaacca tctgcaggcg gtggacggcg gggagatcct ggtcgacggt cgccacgtgg    19800
gctatgtcga gcgcggggga cagctcgtcg aggtcgccga cctcgcacgg gcccgcgctg    19860
aggcccggat cggcatggta ttccagcact tcgacctgtt cgagaacctg tcggtgctgg    19920
acaacgtggc gttcgccccg caccacgtgc acgggctcag cgaggaggcg gcgcgcgagc    19980
gggcgagaca gctgctggtc cgagtgggcc tcggcgagca cctcggctcg ttccccgcca    20040
ccctctccgg tggtcagcgc cagcgggtcg cgatagcccg cgcgctggcc gtcgaccccg    20100
tcgtgatgct gttcgacgag cccacgtcgg cgctcgaccc cgagctggtc gacgaggtgc    20160
tcgacacggt gcgtgggctt gcggcaagcg ggatgacgat gctggtcgtc acccatcacg    20220
tcgagttcgc gcgggagatc gccgaccggg tggtcgtcct cgcggacggg cgcatcgtgg    20280
cccagggccg ccccgacgag gtgctgggag gcccggctgg cgcgcgtggc tgagcagagc    20340
cgcagcggaa tggtctttcg gttttaggtt gatctgcttg tggggtttg cgggcgggtg    20400
```

```
agttgatcga gcgagtgacc ggcgtccggt attcggtgac gcagacctgg acggtgttgc    20460
gcgaacggct tggctggagc cgcaagtcga gttatcaatc ccttgccgcc gcacgttccc    20520
ccggcgtcga cctcgctcac gctgcgacgg cacgctcggt ccgttgcgga cgtacgtgtc    20580
gaccgccggg ggcgagcagt actactcggg gcgctggcgg ggaagcatct tcacggacag    20640
caccgccgct acgacggaga agacgatgct gcctatcacc actgtgctca ggccgctgct    20700
gaacgcgtcc cgcaacagat ccgcggagat ctgcgggtgg gcgacgatcc ttccggcagc    20760
cacctcgtgc gcgatctggg ctgcgcgctc caccgggaag cccatgtcac ccagctggcc    20820
gccgaggaca ctgtggacgt tggcggatag caaggtgccc agcgctgcga caccgacgac    20880
cacgccgagc gggcgcatgc tgttggcgat cccacttgcc aggccagccc gttccacggg    20940
cacgccgccc agggctgccg ccatgatcgg tgcctggcaa agcccgcctc ccgcgccgag    21000
cagcacgaaa gcgggtccga gcagcagcca gctggtgtcg gtggtgatca gggtcagcgg    21060
cagcaggccc agcagcgtca gtgccaccgc cgtcgtggta acggcagatg tgctgtagcg    21120
gctcaacaac ttgccgcccc acggcgcggt caccaggaac ggcaggatga tcggcagcag    21180
ggcgctcccc gcagccaagg cggagtagcc ccggatctgc tggaaccaga tccccaggta    21240
cgtcatcagg ccgaagaagg acgccacgac cgcgaacagg atgaccagtg cccgctgta    21300 gttgcgctgc cggaacaggc tcaggtcgac caggggtgg cggaggcggt gctcagccag    21360
gatgaacacg gcgaacagga cgatggcagc gatcagtgag ccgagcacga cggcgtcgcc    21420
ccagccccgg ccagccaccg agatgatgca gtacgtgatg aagaacagcg ccgccgaggc    21480
cagcagcaga ccggtcaagt ccagcttgcg gtcggcgttg cgctggtcgc ccggcgtgcc    21540
ccgggaggcg atcaggaccg ccatcgagat gggcaggttg atcaggaatg cccaccgcca    21600
gcccggcccg tcgaccagca cgccgccgag caggggcccc acgacgaagg aaaccgaccc    21660
gaccgtggtg tagatgccca gcgcgcgggc gcgttggccg ccggtgaagc ctgcggtgag    21720
ctgcgcgagt ccgctggccg tgagcaccgc tgccgccagc ccctgcaccg cccgggcgcc    21780
aatgagcacg cccggggtct gtgcgatggt gatcagcatc gaagcgagag cgaaggccag    21840
cacgccgatg ccgaacacct tgcggaagcc gatgcggtcg gccagcacgc ccgcggcgag    21900
caggctggct ccgtagacga ggctgtaccc gtcgacgacc cattgcatgc ccgagagcga    21960
aagcgagagg tccgtgctca ttcgggggcag tgccacgttc acgatcgtcg tatcgatgcc    22020
ggccatgccg acggccacgg ccaccacggt cagcagcctt ttctgtcctg ggctccacgg    22080
ctgttctttc agccgcgcag cagcgctttc ctccgaggac gcctctgtca ttgcggggat    22140
tccttcagta actggattgt ttacttgtaa tcaaacctgt ctgcgcagtt atcgtcaagc    22200
cgcgccgaac agctcggaca atgcgctgtg caaggtgtcc gcagggccgg tgccatcgcc    22260
cgcccacgcg atatgcccgt ccgggcggat cagcattgcg tccacaacgg acggttccgt    22320
ggtcttggcg gcgatcaact tcactcgatc ggaccaggct gccgcgactg agcggcaccg    22380
cgaaccgccg ctcagctcca gcagcaccgg tctgccgtcg cgcagcagct ccgccaggcg    22440
ggtggcggtc gcgtcggtga tcaggggaac gtcgtgggcg aattccccgg ccagcggatg    22500
ggagtcgagc ccagcggggt gacggatcca ggtgccggtg atcatctcgg tgagatatcg    22560
gttgacctcg tccatctcga tcatttccgc gaacagctcg cgtagcgcgt cgacctgtgc    22620
gcccggacgc atgagtgcga cctgggcgcg ggtgttggtc aatacgcggg ccgccactgg    22680
gtgttgctcg ctgtggtatg tgtccagcag cgtcggcgac gccagccgc gcacctcggc    22740 agccaacttc cagcccaggt tgaacgcgtc ctgcaggccc aggttcaggc cctgccctcc    22800
```

```
ggtggggaag tgcacgtgcg cggcatcccc ggcgagcagg atccgcccgc tccggtattg   22860
cgccgcctgg cgggtgttgt cggtgaaccg gctcaggtgc tccggggtgg acagcgggaa   22920
gtcctggcca gtgacgcgtc gcacgctcgc cctgatctcg tcgctggtcg ccgggctgtc   22980
gaagtcgacg tcctggtccc attcgcaggt catcacccgg ttgccgagcc agttcaggca   23040
cacaccgcga tcggttcgca cccgcccggg cgggaagttc tcggtcggtg ccggggcgaa   23100
gaaacccaac cgcgccacca cggtgtgccc ggatccgggg aagtcgatgt cggcctgcct   23160
gcgcacagcg ctgcggccac cgtcgcagcc gaccaggaac ggcgcccgcg cccggtaggt   23220
tccgtcgggg gcggagatgt cggcgacgac gccgttctcg tcgtgctcca tcgacgtgaa   23280
ctcgtgcccg tggcggatgg acgcgcccag gtgcagggcg tgttcgcgga ggatttcgtt   23340
gatgctgtcc cggctgaacg ccagggcccg cggctgctcg gtgcgcacct cggacttgcc   23400
gatcacgaac atgccggaga agtgcccgcg cacgcgcgga tgcccgtcgt cgtcctggaa   23460
gtactcctgc agttcgtggg agctgcgcgc gcgtcgtcg aaggcctcca gcagaccgcg    23520
gcgatcgagg agttcgaggc ttcgggagtg cagtcccacg atccgaggct cggtctgctc   23580
cggtcggcac cgctcgacga caagcgtgcg cacgtcgtgc agccgcaact cgcaggcgaa   23640
caggaggccc accgggccac cgccgacgat tatcacctcg aagtctgctt ctggccgcat   23700
ggttctccta atgcaggatt gacacggcgg cacgccgtgg acgaaatgag gggattcaga   23760
cgaacgcttc aaacccagga gcgccgcatg cggccgtccg gagtaaatct cttcctgggg   23820
gtttgtttac atggtaacat cgtcttacgg aaacggctag cggtaagtgg ggaaaccgcg   23880
ctcggggaag ttggctccgg atttcggaac attccgtttg ttgcccttgg tgttggttga   23940
acacctggcg aactcgccga tgctcgcctg caaatagata tgcgtgtgag ggatagatgg   24000
cagatcaggg atatccgcga tctcgtgccg aagcggcggc ggtgttcgaa gcggtcgagg   24060
acagcgtcgc ggccctgacg cgttcgacca cgtgtgccgc gtggacgcgg gacccgggatg  24120
atctgttgct ggtgatcgag gagcccgaag gtggtgctcc aggggacttc ggcgcgctcg   24180
ctcaagaggt gcgcgcggcc gtgtcgcggc agcacgacct cgtgcctgcg gagatcgtgt   24240
tcgtcccagc tcgatccatt cctcgcgcg gcaacgacga ggtgctgcgc gcggagacgg     24300
ctgccattca tctccggggt ggcttggacg tgctgcacgc gacccggcag ctggagtcg    24360
cggcgccgcc gctgctcggc gcggaagaat ccattgtgga cgacgaggtg ctgcgcggcc   24420
tggctgacgc ggccgaaagc ggtggcgagg ccgcgccgct ggacctcgaa ctcatgcggc   24480
tggacgtcgc cgagttgctc ggtgaatcag cggagagcat cgccgacgac gaagacctga   24540
tcatgcgggg cttggactcc atcatgatca tgaccttggt caaccagtgg cgcgccgacg   24600
gggtgcaggt cagcttcccg gagctgttcc aggacgcggt tctggccaag tggtgggaga   24660
gcatcagcgg gaccagcgag cccgaggccg cgacgaggc ggcggtcgac gaggcggtgg    24720
tcgacgagcg ggcgccgttc gacctgtcgg tgatgcagca tgcttactgg gtcggacgcg   24780
gcgacgagca ggtgctcggc ggggtcggcg cgcacttcta caacgagttc agcggtcgcg   24840
acgtggatcc gccgcggctg gagcgcgcgg tgcgggcgct gaccgaacgc cacggcatgc   24900
tgcgagcccg gttcaccgat gacggcaggc aatggatcgc cgccacctgc ccttggcccg   24960
gtctgtcggt gcacgatctg cgtcagctcg ccgcggacga ggtcgaccac cgcctgagct   25020
cgctgcgcga gcgcctgtcc caccgccggc tggaggtcga gcgggggag gtgttcgacg    25080
tccagctctc cctgttgcct ggcggtgcca gccgggtgca cgtcaacatc gacatgctgg   25140
```

```
tcgccgacgc gttgagcttt cgcatcctgc tcaccgacct ggccaggtgc tacgaggaac   25200
cggaggccga gcagccgccc atcggctaca gctacccgaa gtatctggcg cagcgcaacc   25260
gccggcggac ccaggcggcc gagcaggcgc gcgcatactg gcgggaccgg atcgccgacc   25320
tgccaggcgg gccggagctg ccgttggcca tcgcacccga acggatcagc cagcgccggg   25380
tgaccaggcg ttaccactgg ctcgacgcgc aggggcggga tctgctggcg gccaaggcgc   25440
ggcagcacgg gctgaccatg cccgtggtgt tcatgaccgc cttcgccgaa gtgctcggga   25500
cctggagcgc cagcaagagg ttcctgctca acctgcccct gttcgaccgg gaggcggtgc   25560
accccgacgt gttccgcctc agcggcgatt tcaccaactt gatcctgctg gaagtggacc   25620
tgaccgagcc gagctccttc gctgagcgcg cccggcggct gcgtgcgcag ctgcagtccg   25680
acacggccaa cgccgagtac tccggcgtcg cggtcctgcg cgacctggcc agggccaacg   25740
gcggagaacc ggtgcgcgca ccagtggttt tcaccagcgg gctgagcctc ggcgagctgt   25800
tcagcgagga ggtccgccgc tgcttcggca gcccgacatg gatgatctcg cagggccccc   25860
aggtgtggct ggaccaccag gtcaccgagc acgacggggg cttgctgctg aactgggacg   25920
cggagaacga gctgttcccc gacggtcttc ttgacgccat gttcgccgcc taccgcgtcg   25980
tgctggactg gctggccgca gccgactggg cgcagccggt gccgccgttg ctgccggccg   26040
agcaagcggc ggtccgggct accgtcaatg agaccgaggg gccgacgtct ggcctactgc   26100
tgcacgaagg tttcttccgc actgccgaga tcgcgccgca acggcccgcg ttgctttggg   26160
gcgagcaggg cgttctcagc tacggagcgc tcgccgaccg cgcccgccgc attgccggct   26220
tcctgctggg gcgcggggtg cggcccggtg agcgggtggc gatcacgctg ccgaagggtc   26280
ccgaccaggt ggccgcggcg ctcggggtac tactggccgg ggcgacctat gtgccggtgg   26340
gggtggacca gccggtggcg cgccgggcga agatctaccg ccgcgccgag gttcgccagg   26400
tactcaccac tgccgaggag cggacggact cgacctggcc cgccgatgtc gaaccggtcg   26460
cggtcgaggt cgccacgtcg gtggaccccg tgaccaccca ggtgccaggg gaccgaaccg   26520
acctcgccgc ctacgtgatc ttcacgtccg gttcgaccgg cgagccgaag ggtgtgatgg   26580
tcagccatgc ggcggcgatc aacaccatcg ccgacctcaa cgagcgcttc gaggtcggcg   26640
ccgaggaccg ggtgctggcg atctccgcgc tggacttcga cctgtcggtc tacgacatct   26700
tcggcctgct ctcagctggc ggggcgctgg tgctggttcc cgaggccgag cggcgcaacg   26760
ccgcgcactg ggtggagttg gcacggcgct ggaaggtcac gatctggcag tccgtgcccg   26820
cgttgctgga catgctgttg accgcggccg cggctgcgga ccaggtgctg gacctgcggt   26880
tggcgctgct gggcggtgac tgggtgaccg tcgacctgct cgacctgctg cgggcctgct   26940
cgccgaaggg caggctcgtc ggtctccggc ggaccacgga ggccgccatc cactccacca   27000
tttgcgaggt cgaagagatc ccggcccagt ggagctcggt gccctacggc accccgctgc   27060
gcaacgtccg ctgccgggtg gtcgatgagc ggggccagga ctgcccggac tgggggtgg   27120 gggagctgtg gatcggtggc cgtggtgtcg cgctgggcta ctgcggcgac cccgaccgca   27180
ccgccgaacg gttcgtggtg cgggacggga tccgctggta ccgcaccggt gatttggccc   27240
ggtactggcc ggacggttcg ctggagttcc tgggtcgcgc cgaccaccag gtcaaggtgc   27300
ggggccatcg catcgacctg ggtgaggtcg aagccgcgct caacagccac cccgacgtcg   27360
cccgcagtgt cgtggtggtg acggtggcgg ccggtacccg gctggtggct gccgtgtttc   27420 ccggtggggcg tgtgccgcct ctggaagacc tgcgggactg gctcggcacc cagcttcccg   27480
cgcacatggt gcccgccgac ttcgtggtgt tcgacgagct accactcaac gccaacggca   27540
```

```
agatcgaccg caagcggctc gttcgactgc tggcgccgga agagcgcacg acggcggagc    27600
tgcggtcgcc gcagggtccg gtggaagagc tcgtggccca ggcctggtcg gatctgctcg    27660
gcggggagcc gatcggacgc gacgacgact tcttcacccg cggcggtgac agcctgctgg    27720
ccacccgcgt cgtgggcagg ctgcgcgcgg ccggtctgcg cggggctgag ctgcgggcgt    27780
tgttcgccaa gccggtgctg cgggacttcg caacagacct cgaaatcggt gcgtcaccgg    27840
ttgcgagcgc gctcccggct gacccggccc accggtacga gccgttcccg ctcaccgacg    27900
tgcagcaggc ttacctgctg gggcggggcc gggacttcgc gctcggcggt gtcgcgtccc    27960
actggtattg ggagttcgac accgccgatc tggacctgcc gcgcttggag gaggcatgga    28020
accgggtcgt cgcccgccac gagatgctgc gggtcgtgtt cgaggacggc cggcagcgca    28080 tcttgccccgc ggtgccgcgc tatgccctct ccgtcgaaga cgcgcgtggc ggtgctgagc    28140
aggtcgcgct ggaccgaatg cgggccgcca tgtcgcacca ggtgctcgac gtctcgcgct    28200
ggccgctgtt cgacatccgc gccgtgcgct acagcggcgg gcgggtgcgc ctggggttca    28260
gcctcgacct gttgatgctg gacgcgctga gcatcgtgat cgtgttcgcc gagctgagcg    28320
agctctacca ccgtcccgga acccggctgc ccgagatcgg ggtctccttc cgcgactacg    28380
tgctcggtgc ttgcggggat cgagagcagc tcgccgagag caagcgctac tgggcagagc    28440
gggctccttc gctacctccg gcaccgcaac tcccgctgcg caccgatccg gaactcgtcg    28500
cgcagccgcg cttcacccgc aggcagagcc ggattccgcg gcaacgctgg caacgcattg    28560
tcgaacgagc gcggcagcgc gggctcaccc cggcttcggt gctggcgact tgcttcgcgg    28620
aggtcctggg acgctggagc aggcagcggg agctgacgct gaacctgact ctgttcgatc    28680
gccgcgaggt ccaccccgag atcaatggcg tggtcgggga tttcaccgcc ctgctgctgg    28740
tgggttacga gccgagggcg gggagtgct tcgccgagcc gcgcggccgg ttccagcgcc    28800
aaatgtggca ggacctcgac caccgcgacg tctcggcagt gcaggtgatg cgggacctgg    28860
ccgcttcccg cggatctgcg gccgctatgc cggtggtgtt caccagcgcg ctgggcatcg    28920
gccgtgacgt cgccgccgag cggttcgccg aggaggtttg ggggctgtca cagaccccgc    28980
aggtctggct cgatcaccag gtgcgcgacg acgagggcgg catgcggttc aactgggacg    29040
cggtggagga gttgttcccg gaagggctgc tcgacgccat gttccaagct gagtgccgcc    29100
tgctggactg gctggccgat gccgactggt cgcagcaatt gccagacctg cttcccactt    29160
cgcaacgagc ggtgcgcgag caggagaact cgacccgcga accgaccgcc gcagcgacgc    29220
tgctccacag cggattcttc gctcgtgcgg acgccgaccc ggcgcgtacc gccctggtgt    29280
ggggtgcgga ccagcggtgc gagtacggcg aactggccga cctcgccctg cgggtggccg    29340
cgcacttggt ggagcgcggg gtgcgggcgg gcgacaatgt ggccgttgcg ttgcccaagg    29400
gacgcgacca gatcgttgcc gtgctcggcg tcctggccgc tggagccgtg tacgtgccgg    29460
tgggcgtcga tcagcccgat cagcgcaggc agcggatcta ctcgcgggcc ggcgtgcgcg    29520
tggtgctgga cgacctggcg gaggcgtacc gccggaagcc cttggcgggt ccggttgagg    29580
tggatccgga gagcctcgcg tacgtgatct tcacctcggg ttcgaccggt gagccgaagg    29640
gtgtgatggt cagccacgcg tcggcgatga acaccatcgc cgacgtcaac gcccggttcg    29700
gagtcggcgc cgaggaccgg gtgctggcga tctccgcgct ggacttcgat ctgtcggtgt    29760
acgacatttt cggcttgttg tcggtcgcg gttcggtcgt gctcatcgac gaggacggaa    29820
ggcgggaagc ccgcgaatgg gccgggcttt gccgccgctg aacgtcacg gtttggaaca    29880
```

```
ccgtgcccgc tctgctggac atgctgctgg tggtggcaga cgtcctgccc gggtcgtttc    29940
ggctggctct cgtctccggc gactgggtcg gcctggacct ctgggaccga cttcgcgagc    30000
gggcaccggg gtgcgcgctg gtcgcgcttg gcggtgccac cgaggccgcg atctggtcga    30060
acttcttcga agtcgaacgg gtcgaccccgc gatggcgttc gatccccctac ggcagaccgc    30120
tggccaacca gcggttccgc gtggtcgacc ccaccggtca ggactgtcct gagtggaccg    30180
aggggggagct gtggatcggt ggccgcggtg tcgcggccgg ctactgcggc gacgccgatc    30240
gcaccgccga gcggttcgtc gaatgggacg ggatccgctg gtaccggacc ggggacctcg    30300
ggcggtactg gcctgatggc gtgctggagt tcctcggccg ggtcgacaac caggtgaagg    30360
tgcgaggtca ccgcatcgaa ctgggcgaga tcgaggcggc gttgaccgcg catcccgacg    30420
tcggccaggc cgtcgccgcc tccgtcgggg accgggctcc cgcgctcgtg gcggtggtgg    30480
tacccgaggg cgaccggtcc tgcgattccg acgaactgcg atcgtggctg ctcgaccggc    30540
tgcccgccta catggtgccc gagcggatcc ccgagatcgc tgaggtgccg ttgaccgcca    30600
acggcaaaact cgaccgcgcc tcggccatcc gcgggctggc cgacgcgcg cgggaaccgg    30660
ctgagaccgg tgaaccgctt cgcggcgagg tggagatcgc gctggccgag caatggcgcg    30720
aagtgctggg cgtgccggcg ctcgcccgtg acgacaattt cttcgtactc ggcggcgaca    30780
gcctgttggc cacccgcgtg gtggagcgca ttcgccgcct gttcggcgtg gacatcgcgt    30840
tgcgcgagtt cctcgccggg ccatcgcttc agcagcaggg ggaattggtg aaacagcgtt    30900
cgcaggccgg tcaccagatg gaggaaggcg tcatctgatg gcccatcgcg ctacctcgac    30960
cgatgggtgc ggatgggta cgctgcctgt ggaatacgcg tatacaaacc tctgctgtcg    31020
ggagttctgg atgcagaccg agcgcaacaa actgctttac cggcgctgga tcgaagagat    31080
gtggcacgcc gatcccgcga acatggatca gctggcggcc gagctggcgg cacccggttt    31140
cgtcgcgcac tggcccgacc gggaagcgcg cggtccggag gcgctggccg aaatggtccg    31200
acgggggggtc tcgatgttca ccgacgtcaa ggtggccgtg gaggtgggtc cgctggcgga    31260
cggcgacctg gtgtcggggc gctgggtgtt tcgcggttcc tacaacggcg aactgccggg    31320
ggcgccagtg gcgcgcggta ccgaagtggt gttcgcgggt atcgacgtga tgcgctgcgc    31380
cgacggcaag ttcgtcgagt actgggtcag ttccgatggt ttggaattca tgaaacaact    31440
cgggttcacg ccgaagccct gactaaatcc aggtgttctt tgtcgccact tccgacgaac    31500
tgtcggaagt ggtcggcgtt ggttcgcgtt aattgtgtga acgcggctgc taatagtgtg    31560
aacgggtgct gctaagtcct ccgctgctgg attttggatg cttgtcgtcg tggttcggcg    31620
gtgctatgtt ggcgacagcc gaagatctga attcagcggc gaatgcaggt gaagctgggg    31680
gggctggaac accatttccg gcttcgtgga aatcttctc cagttcgctc gctgctcgtc    31740
gaatcgtcgt tttttgggtg ttcacgacgg tggtgtcgat tcggtaagca cacgcgcgcg    31800
tccgacctgg gaggatgaca gatgaatgcc gcagagctgg tcgcggtgct cgaagggctg    31860
ggggtgagcc tgtgggcgga aggcggtcag cttcgtttcc gggcgcccga gggcgtgctg    31920
actgacctcc accggcagca gttgcgtgcg gataaggaag cagtcctcga cgtgttgcgt    31980
gccgcggccg gcaggtgag cgtcgtcgcc gatggcggtg cgcggttcga ccgttcccc    32040
gtcaccgaca tgcaggccgc ctacctcctc ggccgccgcg acgtcttctc ctacggcggg    32100
gtgtcctgcc acggctacgg ggagctcgag ttcaccgagc tcgacccggt ccggttggag    32160
gccgcctggc agcggctgat cgagcggcac gacatgctcc gcgctgtcgt ggacgacgac    32220
ggtacccagc gggtcctgcc aaaaaccctcg ccctaccgca tcagtttcga cgatctttcc    32280
```

```
gaattgggcg agggagcgcg ggcgaagcgc atcgccggga tccggaggga gatggaccac    32340
cgggttcagc ccaacgacgt gtggccgctg ttcgagctgc gggtcagcag ggagccggcc    32400
ctgtcccggc tgcacttctc catcgacttc ctcatcgccg acttcgtcag cattcagctg    32460
ctgctcgaag agctccggca ctgctacgaa cacccccgacg aaccgttgcc gccgttggag   32520
gtgacgttcc gggactacct cgccgcagaa cgccaactgc gcagcggccc ccgctacgaa    32580
cgcgaccgcc agtactggtt gggccgcatc gacgagctgc cgccgcgccc ggatttgccg    32640
atggccgaaa ccaccggttc cgctggccag gcccgtttcc ggcgctacgc gttaatgctc    32700
gaacccgagc agtggtcggc gctgcgggat cgcgccaggg cgaagggcat gacgccatcg    32760
acggcggtgc tggccgcata cgccgaagtc atcgggaagt ggtgccgccg cccggacttc    32820
acgctcaacc tgaccttgct caaccgacag ccgctgcacg ccgacgtgcc ccgcatcatc    32880
ggcgacttca cctcggtcga cctgctcggc gtgtggcaga accgtgcgac gagcttcgct    32940
gatcgggcgg cggcgctgca ggaccaggtc tggcgcgacc ttgaccaccg cctgttctcc    33000
ggcgtcgagg tcatgcgcga aatcgcccgc cgcaacgact ccgacgccgc gctgatgccg    33060
atcgtcttca ccagtgccat cggcgtcggc ggaaccgacg atgggctcgg cgaaaaccag    33120
tggggcaggc tcggctacgg catcagccag accccgcagg tcttcatcga ctgccagaac    33180
atcgagcgct caggcggcct ttcgacgaac tgggacgtgc gggaaggcgt gctgcccgag    33240
tccgtcgtcg cggacatgtt cgcggcatat cgtcagctgc tgacccgcat gtgcaccgag    33300
gacgaggtgt ggaccaagcg gttcccggtc gacctgccgg agcaccagcg agttcgacgg    33360
cactcggtga acgacaccgc ggccccgatg ccggacgcgc tgctgcacga cggcttcatc    33420
gcgcaggccg agcgcgcctc gcaccggacc gccatcctca gcgcccgcgg cgagctgacc    33480 tacgcgagc tgctcgaccg cgcccgcggg gtggccgccg cactgcggga agcgggctgc    33540
cagcgcgggg acgtcgtggg cgtggtcatg gacaagggct gggagcaggt ggccgcggtc    33600
ctgggcatcc acctcggtgg tgccgcatac gtcccggtgg acactgccca accggaggtg    33660
cgccgtgagc ggatgctcgg cgatgccggc gtgcggctgg tgctcaccca aacttggctg    33720
cacgacgagc tgggcctgcc cgagggcatc acgagcatcg tcgtcgacga gcacgggccg    33780
gctggagcct ccgcagcgcc ggacgagcgg gccgcgcccg acgacctggc gtatgtcatc    33840
ttcacgtcgg gctcgaccgg ccggcccaag ggcgtcatga tcacccaccg cagcgcggtc    33900
aacacgatca acgacatcaa caccagattc ggcgtgaccg cgacgaccg ggcgctgatg     33960 ctggccaatc tcggcttcga cctgtcggtc tacgacatct tcggcacctt ggccctcggc    34020
ggggcgctgg tgatccccga gcacgatcga cgatccgatc cctcgcactg ggcggagctg    34080
gtcgccgagc acggggtgac ggtgtggaat tccgtaccag cgcagatgca gatgctccag    34140
cagtatctgg acgccgaaca gctccggctg cccgccgccc ggctcgcctc gctgcgcctg    34200
gcgctgctct ccggtgactg gattccggtc gggctgcccg ccgcagtcga caagcacctg    34260
cccgagctgc ggatgatcag cctcggtggt gcgaccgaag ccgccatctg gtcgatcttc    34320
cacgaggtaa acacgtcggt gatccaccag cgcagcatcc cctacggcaa gccccctgacg   34380 aaccagacct ttcacgtgct ggaccaggac atgcaggact gtccggaagg gacggtcggc    34440
gagctctaca tcggcggtgc cggggtagcc ctgggatacc tcggggatcc agagcgcact    34500
gccgagcgtt tcgtcgtcca ccccaccagc ggcctgcgtc tgtaccgcac gggtgatctg    34560
ggccgctacc gcgaggacag tgagatcgag ttcctcggcc gcgaggactc gcaggtcaag    34620
```

```
atccgcgggc atcgcatcga attggctgag gtcgaggctg cgttgcagtc ccacccgcag   34680
gtgggccggg cgatcgcggt ggtcgacggg gagcgctcga cgaacaaacg gctcgcggcc   34740
ttcgtagaag gccgcgagcc ggaggcggag ccgccgaccg cggagccggt ggtgcgggag   34800
gtgacccgcg ccgcgcagct gatccggcgc ggtttggacg ccgacattga tcgcgaccgc   34860
atcgcggagt tcctcgagcg gctcgacgcg gccctgctac acgccatgac gcacgcgctc   34920
gccgacggtg acccgttcgc cggtggagcc gtccttccg ccgaccaggt cgccgccgcg   34980
ctcggcgtcg cgcaggtgta ccggtcgctg gtgccgcggt ggctcgccga actggcgggg   35040
gccgggttcg tcgagcatga cgagaacgga taccacgacc tgcgcgtggt cgaagccgaa   35100
caggtcgaac ggtgctgggc cgaggccgag gcggtgcgac cggagcggat ctgcccgacc   35160
gcgctgatgg gctacttccg cgactgcgcg cggcaactgc ggcaactgct gcgcggcgag   35220
gtcagcgctt cccggatgtt cttcccggaa ggccggatgg acatcgcgga ggcgacctac   35280
agcgacggcg tggcagcaga ccacaacaac caggtcgccg cccaggcgct gcgcgcgatc   35340
gctgcgcaaa ccggcgggaa acggctgcgg gtgctggagg tcggcggcgg catcgccagc   35400 accaccggc acgtgatgga cgtcctcgcc ggtttcgacg tcgactacac cttcaccgac   35460
gtgtcccagt tcttcctcaa cggcgcgcgg acgcgcttcg ccgcgcagtc gatggacatc   35520
cggatctacg acatcaacca ggactaccgc gaacagggcc tgcgcccgca gtccttcgat   35580
gtggtgctct cgcgcggcgt gctcaacaac gcccgcgata tcgcgtggac cctgcgccag   35640
ctcaaggaga tgctggtccc cggcggttgg ctggtgttca tcgaggcgac tggtgagcac   35700
ttggagatca acgtgtcgca ggcgttcatg atggaggagt tcgaggactt ccgccgcgag   35760
gagggcacca cgttcctcga ccggcggcgc tggctggaac tcgtcgggtc cttggatgcg   35820
gactgggtga cctgtctgcc cgccgagaac gacccgctct ccctgctcgg acagcatgtc   35880
ttcgtggtgc gcctgcggcc cgggaaggtg cgggtcgaag ccgccgacgt cgtcgagcac   35940
gcccgcaagc tgctcccgga acacatgctg cccgtgaaa tgcaggtcgt gcacgacatc   36000
ccgctcagcg acaacggcaa ggtcgaccgc ggcgtgctgc agcagtggtt ggcgcgcagc   36060
gcgccaaccg aacgggcgga caccgccgag gaccacggtg acgagctgga ggagcggctg   36120
gcgagcatgg ccgccgacgt gctcggcgtg cccaggctcg gccgagagca gaacttcttc   36180
gactgcggtg gcgattccct gctggtcgcc cagctcgtcg gccggatacg ggagcaggtt   36240
cccgaagccg ccggcctgta cttcgacggc ctgctgcgcc gcatcctcaa ccagccgaca   36300
attgcggcgc tagccgagca catccggcag acccagcgga ccgagcacga ggcggtggcc   36360
aataccgcga tgtcgccatt gatcgtgctc aacgatccgg gtgcggagcc gctgcgggtt   36420
ctcgtgcacg aagggatcgg cacgatgcg ccgtaccggt ggctggccaa ggaactcctc   36480
gaggcgggac cgctggtcgg gctcgcggtc aacgacacgt ccggttacct gggcctgccc   36540
gccgaggagc tgatcccgcg actcgccgag cgatacgccc gtgagctgct ggaccagggc   36600
ggtgagcagt tccacatcgt cggctactgc ctcggcgggg tgctggcgac cgagatcgcc   36660
ggtcggctca cggaggccgg tgcgcacgtg gcgagcctgg tcgtggtcag cagctaccgc   36720
gtgccctacc agattggcga ggagctgctg ttcgagtacg ccttcggccg ggtgctgtcg   36780
gccgatctcg ggaggatggg gttccccacc gacgaacagc tcgtggggca ggcgttccaa   36840
cgagtgctcg cggcgacccc cggccaagtg ccggacgggg cgttcgacgc gctcgacggg   36900
cagccaggcc tggtggaagt ggcggagcgg ttcgggcgc tgcgccgacg ttcaccggaa   36960
gaacgccggg ccgcgatggc gcggcagttc gttgatgagg gcctcgccgt cggctccccg   37020
```

```
gaacaggcga cccagctgta cgaggtgttc cggcagagct tccgcgcggc gaacctgcat    37080
cagccggagc tctacgcggg tgacatgacg cttctgcggc ctcggggcac gctccggttt    37140
ctgcccggcc tgcaggcgga catgaccgag ttctggcgcg atgtctgcct cggcgagctc    37200
gacgtgatcg acgtcgccgg cgaccacttc agctgcctgg acgcgtcgaa cgtcgccgaa    37260
gctgtccgcc acatccgcgc ggtggccgag aagtccgcag tcagctgatc tccagtcgga    37320
agaaggagca catgagcaga gtcctcgacc ccgggcgcag gccgaaggtc gtggtgtgcg    37380
ggaccaggtg gggccgcgtc tacctccagg cgttcctgga gccggacttc ccgttcgaac    37440
tcgccgggat cgtcgcccag ggcagcgacc ggtcccatgc ctgcgcagag ttctaccagg    37500
ttccgctgta caccaacgtc gaccagctcc ccgacgacat cgacatcgcc tgcgtcgtca    37560
tcagcgcagg agtgcagggt gggcgaggcg cggaaatggc gcaggccatc atgggccgcg    37620
gcatccacgt gctgcaggag cacgcgttgc accacgatga gctggctgaa tgcctgcggt    37680
gcgcccgcaa acacggggtg cagtaccggt tgaacaccca ctaccccgcac atcgagccgg    37740 tccgccggtt catcgccgca gcacgggagc tggtcagcaa gcagcggccg ctgttcatcg    37800
acacgacctg cgccatccaa gtcgcgtaca cgctgttcga catcctgggc cgggcgctcg    37860
gcgaggtccg cccgtggggt ttcgacgacg tgccggtggt gtccgaccgg attcgcggga    37920
tgaccgacct ggagttcccg taccgcgtcg tgaacgcgct gttcgccggt gtgccgatgg    37980
tgctgcgtgt gcagaatcag ctcaagtcca gcgacccgga caactacacc cacctcttcc    38040
accggatcac ggtgggcacc gacggcgggc acctgacgtt ggccaacacg cagggtccgc    38100
tgctctacag cccccgcccg cacggcccgg agcgggcgtg gcacacggtg cggctgttcg    38160
acaccgacgc cgagcatctc acctacccga gcgccaccgt catcggtgac gtcgaaggac    38220
ccgactaccg gcggattgtc ggcgatatct ggccaggtgg tgtccgcaca gcgctaggtg    38280
cgctacgcca tgccgcgctc tccggcaacg atccgctcaa gcaggggcag tactacctga    38340
ccctgtgccg gctgtggcag gacctcacta ccaggctcgg ctatcccgat cagctcaccc    38400
gcacggatcc gccggacgtg ctgccggtcg acgacatgat ggccgccgcg cttgcagtcg    38460
aagtgaagga gggctggggg tgactagcac gatggcgccg ttgtaccagc gctggttccg    38520
gtgttatcgg cccgtggagc actgcgcggg ccggctgatc tgcctgccgc acgccggtgg    38580
ttcggcgagc gcttttcgca cctgggcgcg cgccctgccg ccggacgtgg aactgctcgt    38640
cgcgcagtac ccgggcaggc aggaccgcat ctccgaaccg cacgtccggg acatggacgc    38700
gctgttggcc ggtctgatca gggcgatgcg acccgtgctg gaccggccgt tggccttgct    38760
gggcaacagc atggggggcgg cagtggccta cgaactcgcg cagcatctcg ggtcggcgtg    38820
cgcgcagctg ttcgtttccg ggcggcctgg cccgagccga cagcgacccg gggtggtgca    38880
cctcagcggt gacgacgggc tgctggccga cgtgcgcaat ctcggaggtg tcacacccga    38940
agtgctcgaa gacccggtgc tccgcgaact cttcctgccg actctgcgcg ccgactacca    39000
gctgatcgag acttaccggc cgacgacaag cccgttgccg gtgccggtga tggcgctcat    39060
gggcagcagc gaccccgagg tcgacgaggc cgatgcccgc gcctgggcgg cggccacgac    39120
aggcgagttc gagctgcgct ggttcgacgg tggtcacttc ttcctgaccg accgaccgga    39180
cgacgtggtg aaggtggtcg ccgagcgcct ggccggatcg ttcggagtgc gcgatggccg    39240
ctgaatccga ggctcacgca cgcggggttcg cgatccgcat gttcaccgcc gcagtcgccg    39300
cgcaggagct gttcacaagc tacctcgcc tgaagctcgg cttctaccgg gagttggccg    39360
```

```
ccggtggacc ggcgaccccg ccggagctgg cccggcaatg cggcgccgac gtccggtacg   39420
tgcgggaatg gcttgagcag caggccgtgg cgggaatcct ggaggtgcac gaccaggcaa   39480
tgcccgaact ggaccgccgc tacctgctgc ccgcaggaca cgcggaggcg ctgctgggta   39540
ctgatagccc gtactcgatc tcgccgatcg cggtgctgcc gatgggcgcc accggccggg   39600
tgctgcccgc gctgctggac gcctatcgca ccggcggcgg cgtgccctac accgaatacg   39660
gcgaggattc ccgggacggc cacgccggct ccaaccgagc gctgttcacc aacaacctgg   39720
ccgactggat tcggcgtttc cttccggaca tccacaaccg gctgctcatc agcggccgtg   39780
tcgccgacgt cggatgtggg gcggggtggg cgagcatcgc gctcgcgaag gcctaccccg   39840
atgtccacgt cgacggcttc gatctcgacc agcagtccgt tttggatgcc cggcgcaacg   39900
ctgcggagca cggcgtggcc gaccgggtca gcttcgaggt ccgcgactgc ggcgatgccg   39960
aactggccgg tagctaccag ttggtttgca tcttcgacgc gctgcacgac atgtcgcgtc   40020
cggtcgaggt actgcggacc tgccgtgtgt tgcgcgccaa cgcgggcacg gtgctggtga   40080
tggacgccaa ggtgcccgat cagttccacg cgcccgcgg gacgtcgag cgcttcctgc   40140 acgcggcgag cgttctgcac tgtcttccgg tcggcaggtc agaagagcct tcggcggcca   40200
ccggaacggc gatgcggccc tcgaccgtcc ggacctacgc ggtgaaggcg ggtttctccg   40260
acatcgcggt gctcccggtg gacgacctgt accaccgctt gtaccggctg ctcgactgaa   40320
gtgccgaaat cggactgggg aggaaaggtg accggacgac tcgcacccgg aagcagctcg   40380
tgccggtgat cttcgcatgg cgagggccgg cttgacgcgt tgcaacccgc ccggcccttg   40440
gcggccgcag tggtaaaggc cagggccgaa ctcgccggcg aatgcgtcaa cgccgagcag   40500
gcgcaccggc tcgtgcaccg cttcggttcg ctgctgtagc cgcagattgc gctcggtact   40560
aggggtttcg cggaacagtg ccgggaaagg ttgatcatgc gcacgctgat tatcgacaac   40620
tacgattcct tcacgtacaa cctcgctcac tacctgcaag acgtgaacgg cgaaccgtgc   40680
gaggtcgtcc gcaacgacga tccgacgttc cggttgagtg atctcgaccg gttcgacaac   40740
gtcgtcctct ctcctggacc tggccaccgc gaacgcccgg cggacttcgg ccactgcgcg   40800
gaggtcatcc ggcacgcggc cctgccggtg ctcggcgttt gcctcgggca ccagggcttg   40860
tgcctcgcct acggcggaac cgtggcggcg gctccggagg tccggcacgg gcggctctcg   40920
caggtgaacc acgaaggccg gggcctgttc aacggactgc cctcgccgtt ccggccgtc   40980 cgctaccact cgctggtggt gacccagctt cccgacgagt tcgaggtcga cgcgtggacc   41040
ccggacggcg tgctgatggc cgcacatcac cgaaatcgtc cacagtgggg agtccagttc   41100
cacccggagt cgatctgcac cgagcatggc cacctgctgc tgtgcaactt cgcggagctg   41160 accgccgct ggcagcggga aaacgcacgg ccagcgttac ccctgcgggc ccgggtcgcg   41220
gcgacaccgc acgctgcgca gtcgaggcg aagctgcggg tgctggccga ggaactaccg   41280
ggatggtgcc cgccagagcg ggtgttcgac gcgctctacc aggaaagccc gatttcgttc   41340
tggctggaca gcagcctcgc cgaggggag cagggccggt tctccttcat gggtgacgcg   41400
tccgggccgc tggcgcgggt cgtcgaggcc gacgtctggc agggcttggc gatcgttcgg   41460
gaggcggacc ggaccattga ggtgcgcggc ccgttcctgg actggctgga gtccgatctg   41520
gcggcgctgt gggccgatgt gcccgacctg ccgttcgatt tcgcgctggg ctgggtcggc   41580
tacctcggat acgagatgaa ggccgaatgc ggcgcgcggc gggcgcaccg ggcgcagacg   41640
cccgacgcgg gcatgatctt cgccgaccgc gccgttgcgt tcgaccacca ggagaagcgc   41700
gcctacctgc tcgccctggc cctggtcgac tgcgagcagc ccgcgcagca gtggttggtg   41760
```

```
gagaccggcc gacgatggcg ggaactgcgc tctcaacagt ccgatgagga cgttccggca   41820
ccggccggac cggtccagga gctgcggctg cgccacgatc ggcacgacta catcggactc   41880
atcgaacggt gccaggagca gatccaggcc ggcgagagct acgaggtctg cctgaccaac   41940
atggccaccg gcgaatgcga cctggatccg tggcacagct acaagttcct gcgcgcgcac   42000
agcccggcgc cgttctcagc gctgttgagg ttcggggcgc tgtcggtgct gagcacctcg   42060
ccggagcggt tcctgcggat ttcccgggac cgggcgtgg agtccaagcc gatcaaggga    42120
acgcgacccc gctcggacga ccccgtggag gacgcacgcc tgcgcgagga actgcggacc   42180
agcgagaagg accgcgcgga gaacctgatg atcgtcgacc tggtccgaaa cgacctgggc   42240
aggtgtgcgg aagccggttc tgtccacgtc ccgaagctgt tcgacatcga atccttcgcc   42300
accgtgcatc agatggtcag caccgtgcgg gcacacctgc ggccggacgt ctcgcccatt   42360
gcgtgcgtgc gcgcggcctt ccccggcggt tccatgacgg gtgccccgaa gatccgcacc   42420
atgcagatca tcgacgagtt cgaaagcggt gcgcggggta tctactccgg tgcactcggc   42480
tacttctccc tgagcggggc gaccgatcac agcatcgtca tccgcacgct cgcggtgaac   42540
gctgggcagt tgagcttcgg ggtcggcggg gccatcactg ccctgtcgga tcccgaagag   42600
gagtggaccg agacggcggt gaaggccgct ggactgctgc ggttgttcgg cgcgggcttc   42660
ccgggcaatg acgtggtcgc gaccgaatga gtcgcgatgc aggtcctatg tggacgaaag   42720
ccaaccagtg atcatggctt tcaggccctc ggggtagctg tcggtttcac gggcggtgga   42780
ccactggtcg gagaggcagg cgaggttggg catctgctcc cggtcgacgt cggagaccag   42840
cacgatcgcg aagggcggcc ggtcgagttc gtcggtgcgg cggcgggtgg cagtgcgcac   42900
gagcgcttcg ccgagagtga agtgccacac cgcgcggtag gccgcggcgg cgcacttgcg   42960
gtcgagtccc gccttgacga acgtggcgag gatttcttcg acgatccaga gcaccgaagg   43020
cgccatcatg tcgcctgcgg cgagtacttc gatcgcccag ggatggcgga tgagctgtcc   43080
gtgcaggagt ttccagagct cgatgaggcg atcttggggg ttgtcgggca gttccgggcg   43140
gggtaggcgg gcgacgagcc tgtccaggat gaggacgagg agttcgtcct tgtcctggac   43200
gtggcggtaa acggccatcg gggagctgcc gagttctttc gcgacccggc gcatcgtgag   43260
ggcttctatg ccatcgcgga cgaggatgcg ctcgccgacg tcgacgatgg cgttctggga   43320
cagccgcggt gggcggccgc cccgattcag agtcttgcca gccgggctca tcctgccatt   43380
atgtcagccg gcgggtgcag ccgggaccga actcaccacg tcccacttcg caagatgaag   43440
cggcggagct tgccggtgcc ggtgcgcggg agggcggtca cgaccgcgac ggaccgggga   43500
accttgaacg gcgccagccg gtcgcgcact aagtcgagca attctctttc cagatcctgc   43560
acttccgcgt gccgggtggg gacgatgtag gcgcgcagct tggtcgcacc ccgctggtcg   43620
gcaatcgcgg ccaccgcgga ttcttgcacg gtggggtgct cgtcgaggat ccgttcgatt   43680
tccaccggat ccaccgtgat cccgccaacc atttccagat cgtccttgcg tcccttgtgg   43740
atcaggcgcc cccggtcatc gaatgccgca cggtcgccgg tgttcaacca tccgtcgcgc   43800
agcgcctgcg cggtgcgttc cggctggttg aggtagccgg cgagcagcgt cggcccggtc   43860
acccagagct cgccgtcgac accgcagtca acgatgtccc gaccgctgtc gtcgcgcagg   43920
cgcacctggt aacccggcag cgcgaagccg agcgtgcccg gtcctggtga gtcgagcgtg   43980
ttggcgcaga acgcgccgcc aacctcggta cagccgagct cgtcgagcac gggggccccg   44040
aggatgtcgg tcaaccgctt ccccagctcg gcagcgagcc gttcaccggc cgacaccgca   44100
```

```
acgcgcagcg acgggaaacg ctgcccgtcg atctcggcga ggaggttggc gtatgcggac   44160
ggcaccgcgt gcagcaccga gaccaggtgc cgatcgatcg cttcggccac ggtggacggg   44220
gccgggtgct ccggcagcag caccgcggcc gatccggaca gcagcgggta aacgaacgag   44280
ttgccgaagc cgtaggcgaa gtggagcttc gacaccgaca agctgacatc ggcttcggtc   44340
atgtgcagca tcgccgaacc gacagcgcgg tggtagtgct cgagatcggc gtggcggtgc   44400
ggaacgccaa tggacggcc ggtggtcccg gaggtgtact gcacgtacag cggggcgtgc   44460
gccggtaccg cttgggcggc cgcgaggggg gaggtttcgg cgcgggcgag aagttctccg   44520
gcgtcgaggc accggacgcc atcgaatcgc tccggcgagt cggtgatgac gagctgcgcg   44580
cggcagtctt cggcgatgaa ggtgtggtcg acgaccgtca gcctgggtt ggtggtcacc   44640 gcgacgcgc ccaggcgtgc gagggcgagg aaggtcgcaa tccaggcgat cccgtccggc   44700
atgctcagca gcacgtgctg gcggggccgg acgccgcgct cggccagcac ggttgcggct   44760
cgcgcggcga ggccgtggac ctggccgtgc gtccagctcg aagagccgac gaggtaagcg   44820
gggttgtgct gccagttgtt gcgcgctgag cgtcggcga gtgcctgcgc aacgttcacc   44880
gtttctcctt gtcgacgacg agcggatcag cgggcgggga ggaactcgat gagctggtag   44940
cggatcaccc cgccggatgg cgactcgtag ccgacggcac gccggacggc cggggtccac   45000
ccgtgggcgt cggccaaccg cgcgactcgc ctgccgtcgc cgaggctggt gaaaccgagc   45060
agcaacctgc caccggctt cagccgttcg cccgcttggc gcagaaaagt tcgtgcgcc    45120 tggtagtcga tgtcgtagaa agcttttttcc agatcggaaa tggcgatggt ttcggcggtc   45180
gtcggcacga agttcgagtt ccataaaatg gtgtcatatc gttctcccgg gggaagcggg   45240
gagaacatgt cgccgcagtg cgcggtgagt cgtcggcca ccgcgtgccg tctggcgttc    45300
agctcgatgt tgtcggtggc ggctttgttg atgtcggtgg cgcgaaccag gcggcagccg   45360
cgcagcgcgg cgagcaccgc caggtatccg gtgcccgcgc cgatctcgca gaaacagcca   45420
ccggtcgggt agcggaccca ctccgcgtaa agggctgctg agcgggtcag atggggtgcg   45480
tacacgcctg ggagcaggtc ccagtccagg ccgagcaagc ggaatgtggt tgcgttcgcg   45540
atctggcggt gggcttcgat caggcgggtg accatttgct cgctggaggc gtccatgacc   45600
gcgtgttgct cctctgcgaa acagtcggat tcagggcgag tctaccgatt ccgggtcaat   45660
ggacaagggc tagaaaattg ccaaatgaaa gagtgattta gatcacatat cgcccttttgt   45720 tggggtttgt taacgtgtac gcgtgaaggc aagtgccggg tatccgagga attgccggca   45780
gggcggttcg gttgcgcttg acgacctgtg cgaaaatccg ttcgacgagt tctcgagatg   45840
gcattccgaa ctgggcatga agcgtcgccg ggggcatttc cgcgccgtac tggcggccac   45900
cgggctggac ggcgcgccag aagtgcggtc cgtcgcggtg atccgggtga cgggcgggtt   45960
cgcgttcttc gccgcccacc acggagcggt catcggccgg ttcggggcag accccgtgc    46020 cgcggtgtgc ttcgactggt cggagcaccg ggccgaggtc agagcctgcg gccaggttca   46080
gcgcttgtcc gatgtggact ccgatggtta cttcgggacg ctgccggagc gagagcagct   46140
gacgatctgg ttgcgtgacc aggaaccgac gagcgcgccg cgagccgaga tgacgcgccg   46200
gctcgccgag gtcgcggacc acttccgggg gcagctggtt ccccgccccc agcactgggg   46260
cggttaccgg atcatcgtcg atgacatgct tcttcgcctg cggggcgcgg acgaggtgtg   46320
ggacgaagtc aggtttcggc gcaccgcgag cggatcgtgg ggccgcacct ggagttcctg   46380
ctgacccggg gggcgggcgt cggatcgagg aggcgacgtg ctggcaggat gtgtcgagtg   46440
gcccgacgag gtcgcggcgg agtaccgccg gaagggttac tggcgcgatg agaccctcgg   46500
```

```
cggcctgttg cgcagatggg ccgcagagta cgggcagcgc acggcagtgg tgcgtggcga    46560
ggtgcgttgg agctacgtcg aactcgaccg gcgggccgac cgcctggccg ccggtttcgc    46620
ccagcggggg atcggttcag gtgatcgagt cgttgtgcac ctgccaaaca tccccgagtt    46680
cgtcgcggtg tgcttcgcct tgttccgcct cggtgcggtg ccggtgttcg cactgccacc    46740
gcaccggagc gcggagatca ggtacctgtg cgagtactcg gcggcgattg cctacgtggt    46800
gcccgaatcg cacgccaaaa ccgactaccg gctgatcgcg gcgggcgtcg tctcgaccgt    46860
gccatcgctg cggcacgtgt tcgtggtggg cgatccgggc gaattcaccg cgctcgccga    46920
tgtcgacgct gaacccgccg ccgtgcccga acccggtccg gcggacgtgg ccttcttcct    46980
gctctccggc ggcaccaccg gactgccgaa gcttattccc cgcacccacc gcgattacgc    47040
ctacaacgtc cggatcaccg cggacaacgc cggtctcgat gtcgacacca cctatctggc    47100
ggtgctgccc gcagcgcaca actacgcgct gggctgcccc ggtgtgctgg gtgcgctgtc    47160
ggtcggcggc acggtggtgc tcgccgacag cggcaaccc gatgaggcgt tcaccctgat    47220
cgaacgggaa aaggtgacga tgtccgcact cgtcccgccg ctggcgctgc tgtggaccga    47280
caccgcgacc gagcgggatc tgtcgagcct gcgcctggtg caggtgggcg gttcgcggtt    47340
cgaggccgca ccggctgcca ggttccgggc tcggttcggg tgcgtgttgc agcagtcctt    47400
cggcatggcg gaagggctgc tgagccagac cgcgctgtcg gattcagctg aggtggtcga    47460
ttccacccaa gggctcccgc tctcgcccga tgacgaggtc cggctggtcg acgccgacgc    47520
cgacgccgac gccgacgccg acgccgacgc cgacgccgcc gacgtcgcgg tgggcgaggt    47580
gggccacctg ctggtccggg gtccgtacac gatccgcggc tactaccacg ccccggaaca    47640
gaaccagcgg gacttcacgc cggacgggtt cttccgcacc ggagacctag cgcgccgcac    47700
tccggaaggg cggctgatca tcgagggccg cgtcaaggac gtgattaacc ggggtggtga    47760
gaaggtggcc gccgaagaag tcgaaggtca cctgctggcg cacgaggcgg tgcgggaggt    47820
ggccgtggtg gccgtgcccg acgcggtcat gggcgagcgg acctgtgcct tcgtggtggg    47880
ccgggccgca gtcggcgccg ccgagctcaa ggagttcctc cggggcgcg gcctggccgc    47940 ctacaagctg ccggaccggt gggagcaggt ggagtcgctg ccccgaacgg ccgtcgggaa    48000
gatcgacaag gctctgctgc gcgagcaggt agcggcgaag gtcagccggg cgtcggccag    48060
cagcaggcgt cggcgggcga tccgatgagt cccgtggtcg tggtgggtgc cggccccggtc    48120 ggcctgacgg ccgccctgtg cttgtgcgca cttggcatcg aggtcaccgt gctggagaag    48180
cggggccgcg atgcggtccg ccccggcagc cgggcgctct tcgtgcacaa cgattcgctg    48240
cagctgctcg accgggccca gcgcgggctc ggcaccgaga tcgccgagca cggcaccacc    48300
tggcacaccc gccgcacgct gtttcgcggc cgggaggtct actcgaagac ctatcggaag    48360
ccgaccgggg ccgaactgcc gccattcgcc agccttcgcc agatcgacac cgagcgattc    48420
ctgttgcgtg cggcggagtc ggcaggtgct gacgtcgtct gggacgccga tgtcacccgg    48480
gtctcggcaa cggacgccga cgtgacgttg gaggcggggg acgggcgcag ttggcgcagt    48540
cactacgtga tcgccgccga cggcgcccgt tctgcggtgc gatcggccgt cggcatcgcg    48600
ctggcgggct cccgcgcgtt gggttccac gtcgtggtcg atgtttccgc cggtgcgcgg    48660
ccccggccgc tggagcgcag ctatcactac gcgcaccccg cactgtccgg gcgcaacgtt    48720
ttgacggttc cgttcacggg cggcttccag gtggatctgc agtgccgacc tgatgacgat    48780
ccggacgacc tgaccgcaga ggctgcggtc gcgcgctgga tccgcgccgt cgtcgacgag    48840
```

```
gacgagatcg cgacgtgct ctgggtctcc cactaccagt tcatgcaggt gatcgccgag    48900
cggttcgtcg acgcgagccg ccgggtcctg ctcgccgggg aagcggcgca cctgttcccg    48960
ccgttcgggg cccgcggcat gaacagcggg atggccgacg cggaagcggc ggcgcgtgcg    49020
gtagggctcg cgctgacctg cggcaagcgc acgtctgtgg aggactacga tcgggtccgg    49080
cgagaagctg cccgccgcaa cagctgggcg gtcggtgcag cgttgcggca cgtggcaccg    49140
ccatccccgt tcggcaagat gaagctggcg ctggccggat ggctggctcc gcacgtcccc    49200
aagatcgggg agtggctcga cgggcaccc tacgggccgc ggcggccccc gcgaccaggc    49260
ggaagaggac ggtactgacc atcgcgacga aacgcgggga ccgagtgctc gtgtggcaca    49320
acggtgcgct ccacgaggag tccgctgaac ccaatcgtcc actgtgggtg gtggattcgt    49380
ggctgctcga cgagggcgag gtgcgtggcc tggcgctgca ccgagatcgg ttcgtcaacg    49440
gctgccgcga agcggacaag aaggcccccgg acgaggtgct tggcttctgg ctggagatgt    49500
gccgtgcgtt gccgaggacg ggcaggtggt ttccgcgcgc ggagctcagc ggccatccca    49560
agaagctccg cgcggtgatc cgcccttgcc ccgacaccgg gggagaagtg gtgctgtggc    49620
cgtgcctgga cccgcgcaac tcgcctcgcg gcaaggggcc ggacgtcccg cgcgtggcga    49680
acgcgcggca gaacgcgctc gttagaggtg ctcatgacgc ggtgctgcta acgaaatccg    49740
gagcgctgct tgaggccgct cacggtgcct tgctgtggtg gagcggcgaa cgcatctgta    49800
tgccggtgca tgacgacttg ctgcttccca gcgtcaccct gcgcctgatc cgtcaactcg    49860
cgagccgcga cggcgtccca atagcgcgcg ttgacgccca gctgcaggac ctcgcgaact    49920
gcgaggtgtg gtatgcgaac gccctgcacg gcattcgcct agtgcgctcc tggctgggaa    49980
gtccagtccg gctcggggaa tccgtgcgag cggcgcgctg gcaggacgcg ctcaccgagc    50040
tgcgtgagcc gctgccctga gcggcgcggt gcacgcgcat gacgctgccc ttgccgtgaa    50100
tcccgggatc cgggtgcccc gcattcgacc agcgcgggga acttcccgtc ccgatcgttc    50160
gggtgccggg tcgatccccg tctccttgtc ccggtcgctc attggcagcg gtcgagcaac    50220
atgcgaccac aaccggccaa aaacgaaacc agcgggctca ccttccggca aacccgctgt    50280
tcacagccgt cgagacgacg ggattgtctc gacggcgtcg ttcacgcgct gatcgacacg    50340
accggatcaa cggggtgcgt tgccaacgga tgcacggtga cggccatgta gggccacacg    50400
ggcagggcgc tgatgatgtc gtggagctct gttgcgtcct cggcgcgcca gagtccccag    50460
ttctcccgcc ggcccgggac tcgccacatc cggacgagat gtccttctgc tgcccgctcg    50520
gcggccatct tccgctcgtc gatcgagagt tgccggatcg tgtcggccga agatcgcgt    50580
ggccactcga ttttgatgtt gaccagaaat tccttcatcg aagtctcaaa ctcctcacca    50640
ttttgttcac caatgtcgcg gcgttacgtc ctggtgctcc ggtgacgtat ccgccgggcc    50700
agctgcccgc gccgccacg acgattccca tcgaccgtgc ggcgcgcgtg aagtcggttc    50760
cgggcctgcc gtccagcagt tgtgacggaa gcatgtcgcc gtgggtgatg ttgcttccgg    50820
tgagtccgaa ctcatcttcc aggtcgtgtg gcagaaacca ccgcgcgtcc tcgattcttg    50880
tctgaaggcc ggggaaggac tcttccagct gtgccagaca ggcgccgaag aaagtcgcac    50940
catgctcgcg ccagtactcc cggccgagtc ggtacgcgc gtgccacacg ttgatgctca    51000
tcaggtgttt gcccttgggt gccaaacctt ccgacgtgag actcgggatg agtccccaca    51060
tgatcggctt ggccgaaggg cggcctgcga tgccgtcctc gactgccgcg gtgatgtaag    51120
ccgggtccgg ggcgacccgg aactgggccg agagcagtgt ctccagtggt acgtcctcgg    51180
gagcgccggc gacgccgggg agcgaatcga gagccagggc tatcttgaag gccgacccct    51240
```

```
cgggcggttc gggggtcgcg gcctccgtga gcgccccgga tggaagcatg gtggcgaggc   51300
gggacggttc gactgcggac accaccatgt ccacccecggt gatctgttca cccgactcca   51360
gcaccacggc cgtaacctgt ccgtgttcgg ccagctccag acggacgaca ggagcgttag   51420
ttctgatctg gacgccgtgc tcgcctgcgg ctcgcgcgag tgcgtcgacg atcgcactca   51480
tggagccgac cggtagcccg accgagccgc gcagcggcgc atcgccgatg ccgagcacgt   51540
cttcggtcga cgaggctcgg gagatgggtc gcatgagcag tcccatagcc gaaccgggcg   51600
catccggaga gacgagttgc ccattgaggg cgagcatcat catcaagctc ttggcggcgt   51660
cggtccgcaa cgactcggcg agcaggtcgt tcaggcttcc gtcgagcacg acaaggcgga   51720
actcgtcgcg taccgctgtc ggcatccggt ccagcgcttc ctgcaacgag ggcggcggtt   51780
cccacaacga gagcccgctc gcggcgccga gagcatcgag gcgctcgacg agcagacgat   51840
gccgcttggc ctcaccggta gcgaacgtct ccagctgtgc ggccacccga tcacggtcgc   51900
gccagccgac gaacaggccc tcacccatgc gctgcaacag ggtcacgtcc gggctgacga   51960
accgcaaccc gtgtcgcgcc agctccaact cctggatgat gcgtccctcc aatgaccccg   52020
gggagttggt gatcgcgccg aggtaccegg gaaggtactc cagccgaccg gccatcccgc   52080
cgagcgtggg gcgagcctca aggagggtga cgcgcatccc gaagcgcgcc aggtagttgg   52140
cagcgaccag gccgttgtgt cccccgccga cgacgaccac atggggactc atgcggacgg   52200
gcggtcgaag gtctgctcga acaggcgcag ccagttgccg ccgagaacca ggtccagatc   52260
ggcggcggtg aaccecgctcc gcatcatggt gctgacgagc gtcgggaagg cggcagggga   52320
ctggaaccac gtcggccact cgaccaccgg ggcgctctcg tcgatcggga ccgggctttc   52380
gcgaccccac cggcccatcc gccaccattt gacggcctcg acgtcatacc cggtgtagaa   52440
gtcggtgccc agggcgacgt gttccacacc gaaccgctcg acggtccacg aaatcatgtc   52500
cacgaattcc tgctcggtgg tcttgacgcc gttcttgagc atccgcacgt acgggctcag   52560
gcccacaacg ccgccggcgc tcgcgagctc gcgcagcacg tggacgact tcgggcgccg   52620 gccgagttcg acatcggtac cgacgaactc cagcgggttg gcatgcgtga tcgcaaccgg   52680
aacctggctg aactcgatgg tgtcgaggca cgtccgctcg gagcagtgcg acaggtcgac   52740
gagcattccg acctggttca gttccttcac gaactgccgt cccacgtgag tggacaagcc   52800
ggcgtcgtcg tcctcccagc aaccggcggc gatgctgttc tgggtgttgt aggtgagttg   52860
cacgatccgc acgcccaggt cgtgaaagac ctgcaccagc cggatgtcgt cttcgaaggg   52920
ggaggtgttc tggaatccca gaacgaccgc ggtacgcccg gaggagacca cctcacggat   52980
ctcggccgcg gtgcgggccg gcgcgatcag gtcggcgttc tcggcgaaga ggtcgttcca   53040
gtggcccagg acagacaatg tttcccgggc ggtctcccac accgcgaccg ttacgtggac   53100
gcagccgacg tggccgtcgc gccactccaa gaaccgcttg cgggaaggcc tgctgtactc   53160
gagacaatcc acgatgatgg ccccggtttg cgctcctgct gtcatgtcct ctgctttctt   53220
tccgagtccg attcttgttg acactgattt gggtcaggcg agtccgaaag ggtctgcggc   53280
tgaggcaaag tcctgcacaa tcgctttgac ctcttggaac tcgcgcaagc cttcgatacc   53340
gttctcccgt ccgatgccgg attgcttcac acctccgaac ggtgtctgcc agtccatgcc   53400
ccggtaggtg ttgatccaca cggttccagc gttcaggctc tgcgacatcc ggcgggctcg   53460
cgccatatcg gaggtccagc agccggcagc gagcccgaag gccgagtcgt tggctatcgc   53520
gactgcctcc tcctcggccg cgaactccac gagcgtcagc accgggccga agacctcggt   53580
```

```
ctggcagatg ccggcgctgt tgtcagctac ccgaaggacg gtcggcgcca cccagtaacc   53640
ccgctcgagg ccggcagcca ccggtggggg ctcggcgccg cccgcgagca cggtggcacc   53700
gtcggcgatc gcctgggaga tcaacgactg gatgcgctgc tgctgctgga ccgaggcgac   53760
cgggccgaga tgtaccccgg cctccgtggg ggcaccgacg cgcagccggg acacgcgctc   53820
cagcagcgca gcggtgaatt cgtccgccac accgtgttgc acgagcaccc gagagccggc   53880
cacgcaggtc tgcccggtcg cggagaaccc accctgcacg accgcggtca ccgcatcgtc   53940
gagcggcgca tcatcgaaga tgatgtgagc cgacttgccg ccggcctctg cgacgaagtg   54000
gccgagatga ctcgagacag acatcccgac ctgcgcagcc gcggctgtgc tgccggtgaa   54060
cgagaccatg tccaccgact tgtgctcaac gagccgctgc ccgacgccgg tgccaccctg   54120
gacgatggtc acagcaccgt tgggtacgcc ggcctcggtc acgatctgct tgaggaggat   54180
gctcgagccc ggcgagttaa gcggcggctt gataatgacg gcatttccgg aagccaacgc   54240
cggggcgagt ttccaggtgc cgagggagaa tgctccgttg aatggcgtaa taagtgtcac   54300
gactcccacg ggctcatacc gcagggtcgc ctccttggtc gccgagatgc tgaggcgttc   54360
ctcacgcgta gtgcgcagca gcgcggcgta gtactgccac cagcgtgcgc tgacggctac   54420
ctcggcctta gtcgcaggaa atggcttgcc attggccagc gtctcgagcg ccgcgatttc   54480
atcgacgcgg gcgtcgatgc cgcgcccgat cgcatcgagc acgtcggcgc gctgaaggtt   54540
gctgaccgag cgccattctc cgctggcgta ggtcgcccgg gcaacagcga cggcctcgtc   54600
gaccagatcg acgttgtggc tcaccgtacc ccagggctgg ccggtcgctg ggtcagtgag   54660
tgcttcgtgc cgggtacctt gacgtgtgcg gccgttgatg tccgagtgga attcggttgt   54720
ggagagcaga gcgaataggt ctggcgaggt cgttgcagtc atacagactc ctgtgcggtt   54780
ctcgatatga attcagattt ccgagccgga aaagggcgca atgaagggct caaccggttc   54840
gggcacgcgc tggaatcgtc ctgcggatta cctatcggct gctgtcgacc gcgcacccct   54900
ggtcggcact gatgcgcgag ctgcacgtgt ctccaccgtt cgtccgcctt gcggaatttc   54960
atggccgggg acggagccga gcagctttct cgtgtagggg tgctgcgggt tttcgaagat   55020
ctcgttgttg ctgttggctt cgacgacctc gccgtccttc atcacacaga cgtagtccgc   55080
gatcaaccgc accactgcga gatcgtggga gatgaacagc aagctgaggc cgagctcggc   55140
ctgcaaccgg tcgagaagcc ggaggatctg cgcctgcacc atgacgtcga gggcggacac   55200
gggttcgtcg cagatgagca gatcagggtt gagggcgatc gccctggcga tcgcgacacg   55260
ctgccgctgt ccgccggaca gttcgcgggg gcggcggtcg atcacgtccg aggaaagtgc   55320
gacctgatcg agcagctcga gcacccgcgc gcgtcgttgc gccttgcctc cgcgcttgta   55380
gaaggccaat ggctcctcaa cgatcctgcc gatcgtgtac atcgggttca gcgaggcgta   55440
cggatcctgg aataccggct gcacacgctg ccggaatccg gcgagctggg ccttatccat   55500
cgtcgcgatc tcctgcccct cgaagaagat cgagcccgaa gacggctcga tgagccgaag   55560
gagcatccgc gatgtcgtcg tctttcccga acctgactcg cccacgacgg cgaccgtctt   55620
tccgcccggg atgtcgaacg tgacgccggc agcggctcgg acctccttgc gattgcctcg   55680
gggacggtag attttggtcg cttcccggac ctccacgagg ctcggcttgc cagcgtccgt   55740
ctcaccggtg gcagtatggc ccgagtcgac gcgcacgggc gcgatgctcg ggcggcgtc   55800
gagcagggcc ttcgtgtact ggtggcgcgg agttgccaga acctgcgcag tgggccctgc   55860
ctcgacgatc tcccctcgt tcatcacgat gatccgctgg gcacgttcag ccgcgagggc   55920
gaggtcgtgg gtgatgagca ggaccgcggt gccgatctcg gcggtcatcc tgtcgatctg   55980
```

```
gtcgagaatc gtccgctgga cggtgacatc gagcgcactg gtgggctcgt ctgcgatgag   56040
cagcttcggc cggcaggcga gcccgatcgc gaccagcacg cgctggcgca gcccgccgga   56100
cagctcgtgc ggatactgcg cggcacgctg ttccggctcc gggattcccg cggctcgaag   56160
tgcttcgtgg cttttcccc ggacgtcgcg cctggtcgcg aacccatgtg tcagcagggt   56220
ttccgcgacc tgggtaccta tcttcatgct cgggttcagg ttcgacatcg ggtcctgcgg   56280
caccaaaccg atgagacggc ctcgtacgct acgaagttcg tgtccgact tcgtggtgag    56340 gtcggtgttc tcgaagcgga tgctaccggc gcggattttg ccgttggcgg cgagcagccg   56400
gatgacggac atggccattg tggacttgcc ggaacccgat tctccgacga tcgcgactgt   56460
ctcgccgcgt ccgacacaga acgacacgcc cttgacaacg tcggaggaac cgttgggtcc   56520
ggtgaaactg acgacaaggt tgtcgacagc aagcagcggc agcccgtcgg gggagtcact   56580
catgggtttg ccccttctcg ttggtgacgc tcgccgggct tttcccaatc cgccgtcccg   56640
gcgctgggcg gcggctgtga cgactcccgg atgacgagct tccggggggac ggtgatcggg   56700 ggcatcgcat tgccttgtgc ctcgcccctta accaagctga tgagcctgtt ggtcgccgct   56760
ccggcgatct cttggacaga gccgctgacc gaggacagcg gtggcacgag gtacggcgcg   56820
aagtcgaggt cgccgaagcc gacaacggcg atatcagtgc caacggtacc gccgaggtcc   56880
gtgatggctc ttatcgcgcc cacggcgagt tggtcattcg acgcgagcac cccttcggc    56940 cacggaccga cgcgcaggtg cgccgacatg gccgagtaac cggccttgta gtcgtagccg   57000
tcggtgacga tacggatccc atccgcctgc ccgtggcggc ggaccacgct gctaaatccc   57060
tgccaccgat tctcagcggg gaccgagccc ctgatcgcac caaggaatac aagcggcaca   57120
ccccagtcct cgacgaggtg ggcggtggcc tcttcggcac cgcagtagtc gtcatagaga   57180
atcgtcggga cgtccaggcc cggaatggtc tgtccgatcg tcacgacatg aatccccgc    57240 tcggcgatcc tcgccagctg tgcgcggatc tccggactgc cgaggtcgtc acctgtgttg   57300
atgatgattc cgtcgacgcc ctcgtacggg atgcgggcga ggtagctgag cgccttggcc   57360
tgatcgtggc cgaagctctt cagctgtagc gcgaagctgt gctctgcgca cacggtgtcg   57420
accgacttcg cgatcatcga ataccacggc tgcgagatgt caccgaccag gagggccaga   57480
caccggtggg agcctgatcg caggccggac gccgcccgat tggggtggaa cgacagctcg   57540
tccgcgacct tcagcacctt cttccgcgtg ttctcggcca ccagctccgg acggttgagc   57600
gcccgggaca cggtcgagat ggaaaaaccg gtggcttcgg cgatctcggc catcgtgccg   57660
gcatctggcc tcgtcacagc tttgctcggc tcccggcctg ggccgctagt catgcgcatt   57720
ccccgagaac gtcaccagca cgaacatctg gtctcccctc aactgagctt gatcttcgga   57780
ttgaagtagg cgtacaggat gtcaaccagg aagttgatca atacgaagat cacggcgatc   57840
aacaggatgc cgccctgcaa cagcacggtg tcgcgctgag tgatcgcctg ggacaaggcc   57900
agacctatac cgggccatgc gaataccgtc tcggtgagca cggcaccgct gagcaggaag   57960
ccagcctgga ggccgacgac ggtgatcacc ggggcatcg cgttgggcaa cgcatgccga    58020
aacacgacct tgcgctccgg cgtaccgcgg gatcgggcgc tgcgcacgaa gtcgctgctc   58080
atgacatcga gcatggacgc tcgcgtcatt ctcgcgatga ccgctaccga ccacgccgcg   58140
agcgtgagca cagggaggat cgcgtggctg gcgacgtccc ccagtccacc cccgccgacg   58200
atgcttcgca taccgctaac cggcagccag ccgagggtca gaccgaagag caagacgagg   58260
atcagcccca gccagaacga cggcatgctg gtcagaacaa gcacgaacac cgtcaggccg   58320
```

```
cggtcgcgca acgagttggc cttcagcgcc gcccagctgc cgagcacgat cccgagaacc    58380
gccgccacga ttacggcggg aaccgcgatg acggcggtgt tcaccagccg tgacaacagc    58440
acgtccagag caggctgatg ataggccgtc gagacgccga gatctcctcg aaggagatgt    58500
cctaggtaga tcaaatactg gacgaagatg tttcgatcca cgccgagctg gtcacgcaga    58560
gcctgcttct ccgcctcgct cgcgttgccg cctagccgca catcggctat atcacccgga    58620
atgatctggc tgagcaggaa gaccgcgaac gtcacgccga agatgaccgg gagcagctgg    58680
agcgcacgtt tgcctgtgta cctgagcatg ggtgtgcctc ctcaggagtt gttccgcact    58740
cgcggatcca ggtggtcacg aacgcgtcg ccgaccaggt tgaagccgac agtgagggtg    58800
acgatcgcca gcccggcgag cgtcgccacg tgcggcgcgc tcaacaaggc tgcccggccg    58860
ccgttgagca tcgctcccca gtccggcgtc ggggttta cgccaagccc caggaaactg    58920
aggctcgccg ccaggatcac gttcttgccg gtctgcagcg cgccgatgac caccagcggg    58980
ctcacaacgt tgggggcgac gtgcagggtg gccgtccgga agtgtcccag ccccagcgtg    59040
agagccgact cgacgtaggg ctgctccttc tcgcctagga cgcttccgcg cacgagacgg    59100
ccaacctcgg gaatggtcac cacgaccatc gcgatgatca tcgagaccat gcccgcccc    59160 agggcggcgc cgatccccag cgcgagcagg acgcccggga atgcgaagac gacgtcgaac    59220
acgcgcataa tcaccgcgtc gatcttgccg ccgacgtacc ccgacatcag gccgatcagc    59280
ccgccgatga ccagcgcgat cagtgtcggg gcgaccgcga cgaagagggc gaacctggcg    59340
ccatgaatca gccggctcaa cacgtcccgt ccgagttcat ccgtcccgag gacgtgtccc    59400
ggggagaaca gggccagata cctctggtgc gggtcggcca ggatcgggtc gtgcggcgag    59460
ataaggtcgg cgaagatcgc acagaacacg accacaccga cgatgaccac gcccgtgaca    59520
tgggtgggct tgtcaatgt cgaaagccac ccgctgagcg cgggccgctt tggagacgcg    59580
gtttcctgga caacaccagc cgccatctcg atcatcctct cggtcttgga cagttgaact    59640
caggccacag tccaaagtcg gccgaggttg gggatgacgt ccggcaagcc gagcgtgcgc    59700
aatgcgtgcc agagcgtcga ctggttactg ctgaccactg cggcacccgt gtccatttcg    59760
aggtagggca atgtctcgaa ggttcggtag gtgccacagg agatgaggat cgcgtcagca    59820
ccgccggcct tcttgtacac ggccttgccg aggcggtagg cactgtcggc gtcgtgggtg    59880
ctcgcgtcgt acgggtcggt catctggagg ccttcgatgg cactcacctt gatgccgtga    59940 cttcgagag acgctgccag cgcctcgttc acatcgttgg tgtaaatggt tccgacagcg    60000
acggtggtgg cgtcaagcgc ctgcagcgcc ttgaccgccg actcctgcat cgtaatggct    60060
ggaatcccgg tgtgcgccgt gatctcgctg gtgatgcgct cgtcggcgcc tgggccatcg    60120
aggaaggtcc ccggcgcgcc gcattgcacg atgaggtcga ccttggaggt cgccagctgg    60180
cgggacgcct ccagcacctg cgacatcatc accttcagac ccccctcgtc caccctgggg    60240
acgatggtgc gggcatcggc gaaggcgacg ccggtcgggg cgacgctccg ccactcctcg    60300
gcgccctcga tagcggttgc ggggcggatc tggccgatct tggcgcgcca gcctagaagc    60360
attctgaacc caactcctca agtcgtgatt catcggcaga ccctgtggcc cactctggtc    60420
gcttccccga taccggtcag aacgcgaccc agagggattt gagaaccgtg gcgcagagac    60480
tgacggggga gtgcgacgac gaggaccata agcgcactgc acggccaatg tcaacgtttg    60540
cagtcatcgc gtcaaaggca catgcgcccc gcttgagccg gcgacggaca cgtcgagggg    60600 cggcccgct ggaagtcgca cacgtcccgc gactgatcga ggcaggtgt cgcagcgtct    60660 cgcgagaacc gttgtgcgac agcggaaatg gagcttctac gtagcccaaa ccggacggtg    60720
```

```
tgcacgggtc tgctgaggcg agcgccgccg ttgatgggtc cgccctcggg ccgttgacag    60780
cctgaggcta gccatctacg ttatcccctc acgccacaat cgtttgcaaa gaccacgag    60840 tcccgcatga caatgcgcaa gaggcgtgtc ttggccgccg ttcttgtcgc cacatccctt    60900
ctcggcgtcg ccgcctgctc cggtgtggga cagggcggcg cgaccaacg ggttctcgtc    60960 atcgcctcgg gagggagat tccggcactc gacccgcaga gcatcagtgg aaccgtcggc    61020
cttcgtgtca ctgacgccat ctacgagact ctcgttcgcg aggatctcga tacgcagacc    61080
aagacggctc ccgaagtcag gcctgccctg ccgaatcct ggaacgtgtc ggcggacggc    61140
cgggtttaca cgttcaagat ccgggacggc gtgacgtttc acgacggcac gtccctggac    61200
gcagcggcga tcgctacgaa cttcgaccgc ctgatggacg accgctctcc ggtgtacaac    61260
cagatcgcga cgccaacat gaagttcgtg accgctgga tcgcgagcgc caaggcgacc    61320
ggcgatctta ccttcaccat cacgctcaag aagccgttcg cggagcttcc gcggctgctc    61380
accgaccgcc ggatggcaat catcagccca gtgggccctgg cgaagtaccc aggtgatgca    61440
gtcggtcgac atccggacgg caccggaccc ttccgaatcg agagtgtcga gcagggcacg    61500
gatctgcatc tcgaggccaa tgtgacgtac tggcgcggcg ccccgaaggt cgatggcctc    61560
gtattcgtga acatgcagga tcccacaacc acggcgatgg cgctgcagac cggagaaatc    61620
gatgtgattc ccagcgccag cgcggagcag atcgcgcagc tgcaaggcaa atctgcagcg    61680
gtggtgcagt accggcccc ggccaaccag tattttatcc ggctcaacac caagacagcg    61740
ccgactgaca acccgcagtt ccgccaagcc ttgaactacg cgatcgaccg cgacggaatc    61800
atcgctgccg tggatggcat ggggcagatc atgggcggtc cgatcccggt cggcaacgac    61860
gccttccaag aaggcgctcg gcagcgatac gagttcaatc cggacgaagc acgccgtctc    61920
atccacgctt ccggggtcca gcttccggcg gtcgtcaagg tatacgcccc gagcggcggt    61980
cctggcttct cccaagcaag ccagatcatg tcgctcgtgc aacaagatct gaagaacgtc    62040
gatgtccagc tcgacgtcga atacgtcgag ttcacttcgc tggtaaacct ggaggcgcct    62100
gggtacaaga acggcgtcaa cggctccttc aatgggtgga ccaccggcgc ggacagcggg    62160
tactggctgg agcgaatgtt tggtgcggac cagataccgc cggccggtgt gaaccgcggc    62220
tggtacgtga acacagatct agctcggatc ttcgaccagg cgcgtaacag catcgagccg    62280
gagacgcgcc gcggtctcta tcgcgaagcc gccgacatca tcgctgacga cgcaccttgg    62340
gtctttctct accaagaccg cctgccgcgg atcttccggg cgaacatcac gggaatccac    62400
gggacaccca gcgtgttcgt cgactacgcc actatcagca agtcgtgacc aaacgctgag    62460
caaggcacac agcgtttcgt ggcggtggac ggaatcgctg tcacgaatcc gtgcggtgtc    62520
gcaggtcccc tgccaaccgt tgaacggctt cgccatgtcg ggttgcgaat gagatcgctt    62580
tgtgaatggc gtacggccca tacggatata cagcagcagg atggcctgca ggccgagatg    62640
agcgggcatc tcggctatgc caagggtgat ccggcagggc ggggcagccc gaactcccgc    62700
aggcggcatc agcgccaaga agcatcgccg ctcccgggca ttcggacgcc gggtgatctt    62760
tacctcggcc aaccagctcg ggttgatccg tcgtgatgga accgtcctcg cgcccagacc    62820
gtttagggcc tggcggatgg tgccaaattt cggcggtgaa cggcgtcgtt aagccctgtg    62880
cgggagaacc gcatgcacgg attgacgggc gggagctgga aacggaacca cgatgagacc    62940
acggtcatgg agatcaacga tccaacggga aaccgttggg tcaccgatgg ctccgcgacc    63000
taccgccgat cacggtcacc gcgccagctc ccgaccctac tcggttttcg caggtcggtg    63060
```

| | | |
|---|---|---|
| gcctcatagg ggtttactgg ggtcaagggt cgcaggttca aatcctgtcg gcccgatgtt | 63120 |
| gccttttcgt gtccctatgt ggatcttgcg gtgttcgccg gttcgagatc aaatgggcac | 63180 |
| tggccggtgg cgcggtgcgg gccgcgccac cgccggtccc ggtcgtcagc ccgccgtgaa | 63240 |
| attcggcagg tcggcggtac gggccctgtg caggttcttg atgacgttac gagcgtttga | 63300 |
| gtacttggtc gccccggact cgtagagcag ccatgtcgtg ccgttgtagt cggcgatgcc | 63360 |
| ctccgacatg ctcggcgcct ggaagcactt ggcggagcgg tcgttgatgt tcctgccgtg | 63420 |
| ggcgaccacg tagatgttgc tggggttctt ccggccgtgt gacgtgctgt agacgaagtg | 63480 |
| cgtgtccgtg accatcacgc cctgcgtctt gtcgggtgtt acgtaggtcg cagtctgctt | 63540 |
| gagcttaccg tccttgttca ccttgtagac gtacatccgg tccttttcga aatggcccgt | 63600 |
| gtacagctcg tcgccgtagc cggtgaggaa cgacgctcct ttgaccttct gggccggacc | 63660 |
| gttcggcgcg agcgactgcc tgcccggggc cttgaacttc gccgcgaggt ccgtggtctt | 63720 |
| gtacttgttc atggacctgt tgttgccacc cggtacgaac acccagccat ttacgaccgc | 63780 |
| gatgcccccg gcgtgcttgc ttttgatgtc gaccggtccg aggactctgc tggtgcccgc | 63840 |
| ctcgatcccg tagatgcgcc ccgtgtaatc aggaaccttg ggatgatctg tgtacatgct | 63900 |
| gatcagcatc aggtcgttgc cggcgccgtc ccagttctcc caaaccccca ggccctgggg | 63960 |
| gatgtaaccc tcggacaggc cgggtatcag gttggcctgc ttgaacttgc tgtcgtatac | 64020 |
| cgttccggcg gaagggccgt ggtaggggc ttttcctccc gcgccgctgc tgttgcacgt | 64080 |
| gatcgcggcg gcttcctgcg cgaccgcggt ggccggggg | 64118 |

<210> SEQ ID NO 2
<211> LENGTH: 6942
<212> TYPE: DNA
<213> ORGANISM: Saccharopolyspora Spinosa

<400> SEQUENCE: 2

| | | |
|---|---|---|
| atggcagatc agggatatcc gcgatctcgt gccgaagcgg cggcggtgtt cgaagcggtc | 60 |
| gaggacagcg tcgcggccct gacgcgttcg accacgtgtg ccgcgtggac gcgggaccgg | 120 |
| gatgatctgt tgctggtgat cgaggagccc gaaggtggtg ctccagggga cttcggcgcg | 180 |
| ctcgctcaag aggtgcgcgc ggccgtgtcg cggcagcacg acctcgtgcc tgcggagatc | 240 |
| gtgttcgtcc cagctcgatc cattcctcgc ggcggcaacg acgaggtgct gcgcgcggag | 300 |
| acggctgcca ttcatctccg gggtggcttg gacgtgctgc acgcgacccg gcagctggga | 360 |
| gtcgcggcgc cgccgctgct cggcgcggaa gaatccattg tggacgacga ggtgctgcgc | 420 |
| ggcctggctg acgcggccga aagcggtggc gaggccgcgc cgctggacct cgaactcatg | 480 |
| cggctggacg tcgccgagtt gctcggtgaa tcagcggaga gcatcgccga cgacgaagac | 540 |
| ctgatcatgc ggggcttgga ctccatcatg atcatgacct tggtcaacca gtggcgcgcc | 600 |
| gacggggtgc aggtcagctt cccggagctg ttccaggacg cggttctggc caagtggtgg | 660 |
| gagagcatca gcgggaccag cgagcccgag gccggcgacg aggcggcggt cgacgaggcg | 720 |
| gtggtcgacg aggcggcgcc gttcgacctg tcggtgatgc agcatgctta ctgggtcgga | 780 |
| cgcggcgacg agcaggtgct cggcggggtc ggcgcgcact tctacaacga gttcagcggt | 840 |
| cgcgacgtgg atccgccgcg gctggagcgc gcggtgcggg cgctgaccga acgccacggc | 900 |
| atgctgcgag cccggttcac cgatgacggc aggcaatgga tcgccgccac tgcccttgg | 960 |
| cccggtctgt cggtgcacga tctgcgtcag ctcgccgcgg acgaggtcga ccaccgcctg | 1020 |
| agctcgctgc gcgagcgcct gtcccaccgc cggctggagg tcgagcgggg ggaggtgttc | 1080 |

```
gacgtccagc tctccctgtt gcctggcggt gccagccggg tgcacgtcaa catcgacatg    1140
ctggtcgccg acgcgttgag ctttcgcatc ctgctcaccg acctggccag gtgctacgag    1200
gaaccggagg ccgagcagcc gcccatcggc tacagctacc cgaagtatct ggcgcagcgc    1260
aaccgccggg ggacccaggc ggccgagcag gcgcgcgcat actggcggga ccggatcgcc    1320
gacctgccag gcgggccgga gctgccgttg ccatcgcac ccgaacggat cagccagcgc    1380
cgggtgacca ggcgttacca ctggctcgac gcgcaggggc gggatctgct ggcggccaag    1440
gcgcggcagc acgggctgac catgcccgtg gtgttcatga ccgccttcgc cgaagtgctc    1500
gggacctgga gcgccagcaa gaggttcctg ctcaacctgc ccctgttcga ccgggaggcg    1560
gtgcaccccg acgtgttccg cctcagcggc gatttcacca acttgatcct gctggaagtg    1620
gacctgaccg agccgagctc cttcgctgag cgcgcccggc ggctgcgtgc gcagctgcag    1680
tccgacacgg ccaacgccga gtactccggc gtcgcggtcc tgcgcgacct ggccagggcc    1740
aacggcggag aaccggtgcg cgcaccagtg gttttcacca gcgggctgag cctcggcgag    1800
ctgttcagcg aggaggtccg ccgctgcttc ggcagcccga catggatgat ctcgcagggc    1860
ccccaggtgt ggctggacca ccaggtcacc gagcacgacg ggggcttgct gctgaactgg    1920
gacgcggaga acgagctgtt ccccgacggt cttcttgacg ccatgttcgc cgcctaccgc    1980
gtcgtgctgg actggctggc cgcagccgac tgggcgcagc cggtgccgcc gttgctgccg    2040
gccgagcaag cggcggtccg ggctaccgtc aatgagaccg aggggccgac gtctggccta    2100
ctgctgcacg aaggtttctt ccgcactgcc gagatcgcgc cgcaacggcc cgcgttgctt    2160
tggggcgagc agggcgttct cagctacgga gcgctcgccg accgcgcccg ccgcattgcc    2220
ggcttcctgc tggggcgcgg ggtgcggccc ggtgagcggg tggcgatcac gctgccgaag    2280
ggtcccgacc aggtggccgc ggcgctcggg gtactactgg ccggggcgac ctatgtgccg    2340
gtgggggtgg accagccggt ggcgcgccgg gcgaagatct accgccgcgc cgaggttcgc    2400
caggtactca ccactgccga ggagcggacg gactcgacct ggcccgccga tgtcgaaccg    2460
gtcgcggtcg aggtcgccac gtcggtggac ccgctgacca cccaggtgcc aggggaccga    2520
accgacctcg ccgcctacgt gatcttcacg tccggttcga ccggcgagcc gaagggtgtg    2580
atggtcagcc atgcgcgcgg cgatcaacacc atcgccgacc tcaacgagcg cttcgaggtc    2640
ggcgccgagg accgggtgct ggcgatctcc cgcctggact tcgacctgtc ggtctacgac    2700
atcttcggcc tgctctcagc tggcggggcg ctggtgctgg ttcccgaggc cgagcggcgc    2760
aacgccgcgc actgggtgga gttggcacgg cgctggaagg tcacgatctg gcagtccgtg    2820
cccgcgttgc tggacatgct gttgaccgcg gccgcggctg cggaccaggt gctggacctg    2880
cggttggcgc tgctgggcgg tgactgggtg accgtcgacc tgctcgaccg cctgcgggcc    2940
tgctcgccga agggcaggct cgtcggtctc ggcgggacca cggaggccgc catccactcc    3000
accatttgcg aggtcgaaga gatcccggcc cagtggagct cggtgcccta cggcaccccg    3060
ctgcgcaacg tccgctgccg ggtggtcgat gagcggggcc aggactgccc ggactggggg    3120
gtgggggagc tgtggatcgg tggccgtggt gtcgcgctgg gctactgcgg cgaccccgac    3180
cgcaccgccg aacggttcgt ggtgcgggac gggatccgct ggtaccgcac cggtgatttg    3240
gcccggtact ggccggacgg ttcgctggag ttcctgggtc gcgccgacca ccaggtcaag    3300
gtgcggggcc atcgcatcga cctgggtgag gtcgaagccg cgctcaacag ccaccccgac    3360
gtcgcccgca gtgtcgtggt ggtgacggtg gcggccggta cccggctggt ggctgccgtg    3420
```

```
tttcccggtg ggcgtgtgcc gcctctggaa gacctgcggg actggctcgg cacccagctt    3480
cccgcgcaca tggtgcccgc cgacttcgtg gtgttcgacg agctaccact caacgccaac    3540
ggcaagatcg accgcaagcg gctcgttcga ctgctggcgc cggaagagcg cacgacggcg    3600
gagctgcggt cgccgcaggg tccggtggaa gagctcgtgg cccaggcctg gtcggatctg    3660
ctcggcgggg agccgatcgg acgcgacgac gacttcttca cccgcggcgg tgacagcctg    3720
ctggccaccc gcgtcgtggg caggctgcgc gcggccggtc tgcgcggggc tgagctgcgg    3780
gcgttgttcg ccaagccggt gctgcgggac ttcgcaacag acctcgaaat cggtgcgtca    3840
ccggttgcga gcgcgctccc ggctgacccg gcccaccggt acgagccgtt cccgctcacc    3900
gacgtgcagc aggcttacct gctggggcgg ggccgggact tcgcgctcgg cggtgtcgcg    3960
tcccactggt attgggagtt cgacaccgcc gatctggacc tgccgcgctt ggaggaggca    4020
tggaaccggg tcgtcgcccg ccacgagatg ctgcgggtcg tgttcgagga cggccggcag    4080
cgcatcttgc ccgcggtgcc gcgctatgcc ctctccgtcg aagacgcgcg tggcggtgct    4140
gagcaggtcg cgctggaccg aatgcggggcc gccatgtcgc accaggtgct cgacgtctcg    4200
cgctggccgc tgttcgacat ccgcgccgtg cgctacagcg gcgggcgggt gcgcctgggg    4260
ttcagcctcg acctgttgat gctggacgcg ctgagcatcg tgatcgtgtt cgccgagctg    4320
agcgagctct accaccgtcc cggaacccgg ctgcccgaga tcggggtctc cttccgcgac    4380
tacgtgctcg gtgcttgcgg ggatcgagag cagctcgccg agagcaagcg ctactgggca    4440
gagcgggctc cttcgctacc tccggcaccg caactcccgc tgcgcaccga tccggaactc    4500
gtcgcgcagc cgcgcttcac ccgcaggcag agccggattc cgcggcaacg ctggcaacgc    4560
attgtcgaac gagcgcggca gcgcgggctc accccggctt cggtgctggc gacttgcttc    4620
gcggaggtcc tgggacgctg gagcaggcag cgggagctga cgctgaacct gactctgttc    4680
gatcgccgcg aggtccaccc cgagatcaat ggcgtggtcg gggatttcac cgccctgctg    4740
ctggtgggtt acgagccgag ggcggggggag tgcttcgccg agcgcgcggc ccggttccag    4800
cgccaaatgt ggcaggacct cgaccaccgc gacgtctcgg cagtgcaggt gatgcgggac    4860
ctggccgctt cccgcggatc tgcggccgct atgccggtgg tgttcaccag cgcgctgggc    4920
atcggccgtg acgtcgccgc cgagcggttc gccgaggagg tttgggggct gtcacagacc    4980
ccgcaggtct ggctcgatca ccaggtgcgc gacgacgagg cggcatgcg gttcaactgg    5040 gacgcggtgg aggagttgtt cccggaaggg ctgctcgacg ccatgttcca agctgagtgc    5100
cgcctgctgg actggctggc cgatgccgac tggtcgcagc aattgccaga cctgcttccc    5160
acttcgcaac gagcggtgcg cgagcaggag aactcgaccc gcgaaccgac cgccgcagcg    5220
acgctgctcc acagcggatt cttcgctcgt cgggacgccg accgcgcgcg taccgccctg    5280 gtgtgggggtg cggaccagcg gtgcgagtac ggcgaactgg ccgacctcgc cctgcgggtg    5340
gccgcgcact tggtggagcg cggggtgcgg cgggcgaca atgtggccgt tgcgttgccc    5400
aagggacgcg accagatcgt tgccgtgctc ggcgtcctgg ccgctggagc cgtgtacgtg    5460
ccggtgggcg tcgatcagcc cgatcagcgc aggcagcgga tctactcgcg ggccggcgtg    5520
cgcgtggtgc tggacgacct ggcggaggcg taccgccgga agcccttggc gggtccggtt    5580
gaggtggatc cggagagcct cgcgtacgtg atcttcacct cgggttcgac cggtgagccg    5640
aagggtgtga tggtcagcca cgcgtcggcg atgaacacca tcgccgacgt caacgcccgg    5700 ttcgagtcg gcgccgagga ccgggtgctg gcgatctccg cgctggactt cgatctgtcg    5760
gtgtacgaca ttttcggctt gttgtcggtc ggcggttcgg tcgtgctcat cgacgaggac    5820
```

```
ggaaggcggg aagcccgcga atgggccggg ctttgccgcc gctggaacgt cacggtttgg    5880
aacaccgtgc ccgctctgct ggacatgctg ctggtggtgg cagacgtcct gcccgggtcg    5940
tttcggctgg ctctcgtctc cggcgactgg gtcggcctgg acctctggga ccgacttcgc    6000
gagcgggcac cggggtgcgc gctggtcgcg cttggcggtg ccaccgaggc cgcgatctgg    6060
tcgaacttct tcgaagtcga acgggtcgac ccgcgatggc gttcgatccc ctacggcaga    6120
ccgctggcca accagcggtt ccgcgtggtc gaccccaccg tcaggactg tcctgagtgg     6180 accgaggggg agctgtggat cggtggccgc ggtgtcgcgg ccggctactg cggcgacgcc    6240
gatcgcaccg ccgagcggtt cgtcgaatgg gacgggatcc gctggtaccg gaccggggac    6300
ctcgggcggt actggcctga tggcgtgctg gagttcctcg gccgggtcga caaccaggtg    6360
aaggtgcgag gtcaccgcat cgaactgggc gagatcgagg cggcgttgac cgcgcatccc    6420
gacgtcggcc aggccgtcgc cgcctccgtc ggggaccggg ctcccgcgct cgtggcggtg    6480
gtggtacccg agggcgaccg gtcctgcgat tccgacgaac tgcgatcgtg gctgctcgac    6540
cggctgcccg cctacatggt gcccgagcgg atcgccgaga tcgctgaggt gccgttgacc    6600
gccaacggca aactcgaccg cgcctcggcc atccgcgggc tggccgacgg cgcgcgggaa    6660
ccggctgaga ccggtgaacc gcttcgcggc gaggtggaga tcgcgctggc cgagcaatgg    6720
cgcgaagtgc tgggcgtgcc ggcgctcgcc cgtgacgaca atttcttcgt actcggcggc    6780
gacagcctgt tggccacccg cgtggtggag cgcattcgcc gcctgttcgg cgtggacatc    6840
gcgttgcgcg agttcctcgc cgggccatcg cttcagcagc aggggaatt ggtgaaacag     6900 cgttcgcagg ccggtcacca gatggaggaa ggcgtcatct ga                       6942

<210> SEQ ID NO 3
<211> LENGTH: 412
<212> TYPE: DNA
<213> ORGANISM: Saccharopolyspora Spinosa

<400> SEQUENCE: 3
gtctacctcc aggcgttcct ggagccggac ttcccgttcg aactcgccgg gatcgtcgcc      60
cagggcagcg accggtccca tgcctgcgca gagttctacc aggttccgct gtacaccaac     120
gtcgaccagc tccccgacga catcgacatc gcctgcgtcg tcatcagcgc aggagtgcag     180
ggtgggcgag gcgcggaaat ggcgcaggcc atcatgggcc gcggcatcca cgtgctgcag     240
gagcacgcgt tgcaccacga tgagctggct gaatgcctgc ggtgcgcccg caaacacggg     300
gtgcagtacc ggttgaacac ccactacccg cacatcgagc cggtccgccg gttcatcgcc     360
gcagcacggg agctggtcag caagcagcgg ccgctgttca tcgacacgac ct             412

<210> SEQ ID NO 4
<211> LENGTH: 20
<212> TYPE: DNA
<213> ORGANISM: Artificial
<220> FEATURE:
<223> OTHER INFORMATION: Forward PCR primer

<400> SEQUENCE: 4
gtctacctcc aggcgttcct                                                   20

<210> SEQ ID NO 5
<211> LENGTH: 20
<212> TYPE: DNA
<213> ORGANISM: Artificial
<220> FEATURE:
```

<223> OTHER INFORMATION: Reverse PCR primer

<400> SEQUENCE: 5
aggtcgtgtc gatgaacagc                                                    20

<210> SEQ ID NO 6
<211> LENGTH: 303
<212> TYPE: DNA
<213> ORGANISM: Artificial
<220> FEATURE:
<223> OTHER INFORMATION: Actinophage attachment site (attB) nucleotide
      sequence from Streptomyces lividans containing BamHI and NdeI
      sites

<400> SEQUENCE: 6
ggatcccgga atgtcgacga tgtaggtcac ggtctcgaag ccgcggtgcg ggtgccaggg         60
cgtgcccttg ggctccccgg gcgcgtactc cacctcaccc atctggtcca tcatgatgaa       120
cgggtcgagg tggcggtagt tgatcccggc gaacgcgcgg cgcaccggga agccctcgcc       180
ctcgaaaccg ctgggcgcgg tggtcacggt gagcacggga cgtgcgacgg cgtcggcggg       240
tgcggatacg cggggcagcg tcagcgggtt ctcgacggtc acggcgggca tgtcgaccat       300
atg                                                                    303

<210> SEQ ID NO 7
<211> LENGTH: 22
<212> TYPE: DNA
<213> ORGANISM: Artificial
<220> FEATURE:
<223> OTHER INFORMATION: Forward PCR primer 2

<400> SEQUENCE: 7
tgtaggctgg agctgcttcg aa                                                 22

<210> SEQ ID NO 8
<211> LENGTH: 29
<212> TYPE: DNA
<213> ORGANISM: Artificial
<220> FEATURE:
<223> OTHER INFORMATION: Reverse PCR primer 2

<400> SEQUENCE: 8
catatggata ttccggggat ccgtcgacc                                          29

<210> SEQ ID NO 9
<211> LENGTH: 4477
<212> TYPE: DNA
<213> ORGANISM: Artificial
<220> FEATURE:
<223> OTHER INFORMATION: pCR8/GW/TOPO_aac(3)-attB plasmid nucleotide
      sequence

<400> SEQUENCE: 9
ctttcctgcg ttatcccctg attctgtgga taaccgtatt accgcctttg agtgagctga        60
taccgctcgc cgcagccgaa cgaccgagcg cagcgagtca gtgagcgagg aagcggaaga      120
gcgcccaata cgcaaaccgc ctctccccgc gcgttggccg attcattaat gcagctggca      180
cgacaggttt cccgactgga aagcgggcag tgagcgcaac gcaattaata cgcgtaccgc      240
tagccaggaa gagtttgtag aaacgcaaaa aggccatccg tcaggatggc cttctgctta      300
gtttgatgcc tggcagttta tggcgggcgt cctgcccgcc accctccggg ccgttgcttc      360
acaacgttca aatccgctcc cggcggattt gtcctactca ggagagcgtt caccgacaaa      420

```
caacagataa aacgaaaggc ccagtcttcc gactgagcct ttcgttttat ttgatgcctg      480
gcagttccct actctcgcgt taacgctagc atggatgttt ccccagtcac gacgttgtaa      540
aacgacggcc agtcttaagc tcgggcccca aataatgatt ttattttgac tgatagtgac      600
ctgttcgttg caacaaattg atgagcaatg cttttttata atgccaactt tgtacaaaaa      660
agcaggctcc gaattcgccc tttgtaggct ggagctgctt cgaagttcct atactttcta      720
gagaatagga acttcggaat aggaacttat gagctcagcc aatcgactgg cgagcggcat      780
cgcattcttc gcatcccgcc tctggcggat gcaggaagat caacggatct cggcccagtt      840
gacccagggc tgtcgccaca atgtcgcggg agcggatcaa ccgagcaaag gcatgaccga      900
ctggaccttc cttctgaagg ctcttctcct tgagccacct gtccgccaag gcaaagcgct      960
cacagcagtg gtcattctcg agataatcga cgcgtaccaa cttgccatcc tgaagaatgg     1020
tgcagtgtct cggcaccccca tagggaacct ttgccatcaa ctcggcaaga tgcagcgtcg     1080
tgttggcatc gtgtcccacg ccgaggagaa gtacctgccc atcgagttca tggacacggg     1140
cgaccgggct tgcaggcgag tgaggtggca ggggcaatgg atcagagatg atctgctctg     1200
cctgtggccc cgctgccgca aaggcaaatg gatgggcgct cgctttaca tttggcaggc      1260 gccagaatgt gtcagagaca actccaaggt ccggtgtaac gggcgacgtg caggatcga      1320 acggctcgtc gtccagacct gaccacgagg gcatgacgag cgtccctccc ggacccagcg     1380
cagcacgcag ggcctcgatc agtccaagtg gcccatcttc gaggggccgg acgctacgga     1440
aggagctgtg gaccagcagc acaccgccgg gggtaacccc aaggttgaga agctgaccga     1500
tgagctcggc ttttcgccat tcgtattgca cgacattgca ctccaccgct gatgacatca     1560
gtcgatcata gcacgatcaa cggcactgtt gcaaatagtc ggtggtgata aacttatcat     1620
ccccttttgc ttatggagct gcacatgaac ccattcaaag gccggcattt tcagcgtgac     1680
atcattctgt gggccgtacg ctggtactgc aaatacggca tcagttaccg tgagctgcat     1740
tttccgctgc ataaccctgc ttcggggtca ttatagcgat ttttttcggta tatccatcct     1800 ttttcgcacg atatacagga ttttgccaaa gggttcgtgt agactttcct tggtgtatcc     1860
aacggcgtca gccgggcagg ataggtgaag taggcccacc cgcgagcggg tgttccttct     1920
tcactgtccc ttattcgcac ctggcggtgc tcaacgggaa tcctgctctg cgaggctggc     1980
gggaacttcg aagttcctat actttctaga aataggaac ttcgaactgc aggtcgacgg      2040
atccccggaa tgtcgacgat gtaggtcacg gtctcgaagc cgcggtgcgg gtgccagggc     2100
gtgcccttgg gctccccggg cgcgtactcc acctcacccca tctggtccat catgatgaac     2160
gggtcgaggt ggcggtagtt gatcccggcg aacgcgcggc gcaccgggaa gccctcgccc     2220
tcgaaaccgc tgggcgcgt ggtcacggtg agcacgggac gtgcgacggc gtcggcgggt      2280
gcggatacgc ggggcagcgt cagcgggttc tcgacggtca cggcgggcat gtcgaccata     2340
tgaagggcga attcgaccca gctttcttgt acaaagttgg cattataaaa aataattgct     2400
catcaatttg ttgcaacgaa caggtcacta tcagtcaaaa taaaatcatt atttgccatc     2460
cagctgatat cccctatagt gagtcgtatt acatggtcat agctgttttcc tggcagctct     2520 ggcccgtgtc tcaaaatctc tgatgttaca ttgcacaaga taaaaatata tcatcatgcc     2580
tcctctagac cagccaggac agaaatgcct cgacttcgct gctgcccaag gttgccgggt     2640
gacgcacacc gtggaaacgg atgaaggcac gaacccagtg gacataagcc tgttcggttc     2700
gtaagctgta atgcaagtag cgtatgcgct cacgcaactg gtccagaacc ttgaccgaac     2760
gcagcggtgg taacggcgca gtggcggttt tcatggcttg ttatgactgt ttttttgggg     2820
```

```
tacagtctat gcctcgggca tccaagcagc aagcgcgtta cgccgtgggt cgatgtttga    2880
tgttatggag cagcaacgat gttacgcagc agggcagtcg ccctaaaaca aagttaaaca    2940
tcatgaggga agcggtgatc gccgaagtat cgactcaact atcagaggta gttggcgtca    3000
tcgagcgcca tctcgaaccg acgttgctgg ccgtacattt gtacggctcc gcagtggatg    3060
gcggcctgaa gccacacagt gatattgatt tgctggttac ggtgaccgta aggcttgatg    3120
aaacaacgcg gcgagctttg atcaacgacc ttttggaaac ttcggcttcc cctggagaga    3180
gcgagattct ccgcgctgta gaagtcacca ttgttgtgca cgacgacatc attccgtggc    3240
gttatccagc taagcgcgaa ctgcaatttg gagaatggca cgcaatgac attcttgcag     3300 gtatcttcga gccagccacg atcgacattg atctggctat cttgctgaca aaagcaagag    3360
aacatagcgt tgccttggta ggtccagcgg cggaggaact cttgatccg gttcctgaac     3420 aggatctatt tgaggcgcta atgaaacct taacgctatg gaactcgccg cccgactggg     3480
ctggcgatga gcgaaatgta gtgcttacgt tgtcccgcat ttggtacagc gcagtaaccg    3540
gcaaaatcgc gccgaaggat gtcgctgccg actgggcaat ggagcgcctg ccggcccagt    3600
atcagcccgt catacttgaa gctagacagg cttatcttgg acaagaagaa gatcgcttgg    3660
cctcgcgcgc agatcagttg gaagaatttg tccactacgt gaaaggcgag atcaccaagg    3720
tagtcggcaa ataaccctcg agccacccat gaccaaaatc ccttaacgtg agttacgcgt    3780
cgttccactg agcgtcagac cccgtagaaa agatcaaagg atcttcttga tccttttt     3840 ttctgcgcgt aatctgctgc ttgcaaacaa aaaaaccacc gctaccagcg gtggtttgtt    3900
tgccggatca gagctacca actctttttc cgaaggtaac tggcttcagc agagcgcaga     3960
taccaaatac tgtccttcta gtgtagccgt agttaggcca ccacttcaag aactctgtag    4020
caccgcctac atacctcgct ctgctaatcc tgttaccagt ggctgctgcc agtggcgata    4080
agtcgtgtct taccgggttg gactcaagac gatagttacc ggataaggcg cagcggtcgg    4140
gctgaacggg gggttcgtgc acacagccca gcttggagcg aacgacctac accgaactga    4200
gatacctaca gcgtgagcat tgagaaagcg ccacgcttcc cgaagggaga aaggcggaca    4260
ggtatccggt aagcggcagg gtcggaacag gagagcgcac gagggagctt ccaggggaa     4320 acgcctggta tctttatagt cctgtcgggt ttcgccacct ctgacttgag cgtcgatttt    4380
tgtgatgctc gtcaggggg cggagccat ggaaaaacgc cagcaacgcg ccttttac        4440 ggttcctggc cttttgctgg ccttttgctc acatgtt                            4477
```

<210> SEQ ID NO 10
<211> LENGTH: 58
<212> TYPE: DNA
<213> ORGANISM: Artificial
<220> FEATURE:
<223> OTHER INFORMATION: Forward PCR primer 3
<220> FEATURE:
<221> NAME/KEY: misc_feature
<222> LOCATION: (1)..(39)
<223> OTHER INFORMATION: Based on cosmid sequence
<220> FEATURE:
<221> NAME/KEY: primer_bind
<222> LOCATION: (40)..(58)
<223> OTHER INFORMATION: Hybridizes with aac(3)-attB cassette

<400> SEQUENCE: 10

```
tcgacggcct gctgcgccgc atcctcaacc agccgacaat gtaggctgga gctgcttc         58
```

<210> SEQ ID NO 11

```
<211> LENGTH: 59
<212> TYPE: DNA
<213> ORGANISM: Artificial
<220> FEATURE:
<223> OTHER INFORMATION: Reverse PCR primer 3
<220> FEATURE:
<221> NAME/KEY: misc_feature
<222> LOCATION: (1)..(39)
<223> OTHER INFORMATION: Based on cosmid sequence
<220> FEATURE:
<221> NAME/KEY: primer_bind
<222> LOCATION: (40)..(59)
<223> OTHER INFORMATION: Hybridizes with aac(3)-attB cassette

<400> SEQUENCE: 11
aacgcaccgc gcaggcgctg cgcgacggat ggttgaacac atatggtcga catgcccgc      59

<210> SEQ ID NO 12
<211> LENGTH: 1738
<212> TYPE: DNA
<213> ORGANISM: Artificial
<220> FEATURE:
<223> OTHER INFORMATION: Junction where thiazolinyl imide reductase gene
      was partially deleted within cosmid clone 4G15

<400> SEQUENCE: 12
tcgacggcct gctgcgccgc atcctcaacc agccgacaat gtaggctgga gctgcttcga      60
agttcctata ctttctagag aataggaact tcggaatagg aacttatgag ctcagccaat     120
cgactggcga gcggcatcgc attcttcgca tcccgcctct ggcggatgca ggaagatcaa     180
cggatctcgg cccagttgac ccagggctgt cgccacaatg tcgcgggagc ggatcaaccg     240
agcaaaggca tgaccgactg gaccttcctt ctgaaggctc ttctccttga gccacctgtc     300
cgccaaggca aagcgctcac agcagtggtc attctcgaga taatcgacgc gtaccaactt     360
gccatcctga agaatggtgc agtgtctcgg caccccatag gaacctttg ccatcaactc      420 ggcaagatgc agcgtcgtgt tggcatcgtg tcccacgccg aggagaagta cctgcccatc     480
gagttcatgg acacgggcga ccgggcttgc aggcgagtga ggtggcaggg gcaatggatc     540
agagatgatc tgctctgcct gtggccccgc tgccgcaaag gcaaatggat gggcgctgcg     600
ctttacattt ggcaggcgcc agaatgtgtc agagacaact ccaaggtccg gtgtaacggg     660
cgacgtggca ggatcgaacg gctcgtcgtc cagacctgac cacgagggca tgacgagcgt     720
ccctcccgga cccagcgcag cacgcagggc ctcgatcagt ccaagtggcc catcttcgag     780
gggccggacg ctacggaagg agctgtggac cagcagcaca ccgccggggg taaccccaag     840
gttgagaagc tgaccgatga gctcggcttt tcgccattcg tattgcacga cattgcactc     900
caccgctgat gacatcagtc gatcatagca cgatcaacgg cactgttgca aatagtcggt     960
ggtgataaac ttatcatccc cttttgctga tggagctgca catgaaccca ttcaaaggcc    1020
ggcattttca gcgtgacatc attctgtggg ccgtacgctg gtactgcaaa tacggcatca    1080
gttaccgtga gctgcatttt ccgctgcata accctgcttc ggggtcatta tagcgatttt    1140
ttcggtatat ccatcctttt tcgcacgata tacaggattt tgccaagggg ttcgtgtaga    1200
ctttccttgg tgtatccaac ggcgtcagcc gggcaggata ggtgaagtag gcccaccgc     1260 gagcgggtgt tccttcttca ctgtccctta ttcgcacctg gcggtgctca acggaatcc     1320 tgctctgcga ggctggcggg aacttcgaag ttcctatact ttctagagaa taggaacttc    1380
gaactgcagg tcgacggatc cccggaatgt cgacgatgta ggtcacggtc tgaagccgc     1440 ggtgcgggtg ccaggggcgtg cccttgggct cccggggcgc gtactccacc tcacccatct    1500
```

-continued

```
ggtccatcat gatgaacggg tcgaggtggc ggtagttgat cccggcgaac gcgcggcgca    1560
ccgggaagcc ctcgccctcg aaaccgctgg gcgcggtggt cacggtgagc acgggacgtg    1620
cgacggcgtc ggcgggtgcg gatacgcggg gcagcgtcag cgggttctcg acggtcacgg    1680
cgggcatgtc gaccatatgt gttcaaccat ccgtcgcgca gcgcctgcgc ggtgcgtt     1738
```

IDENTIFICATION AND CHARACTERIZATION OF THE SPINACTIN BIOSYSNTHESIS GENE CLUSTER FROM SPINOSYN PRODUCING *SACCHAROPOLYSPORA SPINOSA*

CROSS-REFERENCE TO RELATED APPLICATION

This application claims the benefit of U.S. Provisional Patent Application Ser. No. 61/580,947, filed Dec. 28, 2011, the disclosure of which is hereby incorporated herein in its entirety by this reference.

TECHNICAL FIELD

The present disclosure generally relates to methods of producing spinosyn with reduced impurities and to spinactin and its biosynthesis.

BACKGROUND

As disclosed in U.S. Pat. No. 5,362,634, fermentation product A83543 is a family of related compounds produced by *Saccharopolyspora spinosa*. The known members of this family have been referred to as factors or components, and each has been given an identifying letter designation. These compounds are hereinafter referred to as spinosyn A, B, etc. The spinosyn compounds are useful for the control of arachnids, nematodes and insects, in particular, *Lepidoptera* and *Diptera* species, and they are quite environmentally friendly and have an appealing toxicological profile.

The naturally produced spinosyn compounds consist of a 5,6,5-tricylic ring system, fused to a 12-membered macrocyclic lactone, a neutral sugar (rhamnose) and an amino sugar (forosamine) (see Kirst et al. (1991). If the amino sugar is not present, the compounds have been referred to as the pseudoaglycone of A, D, etc., and if the neutral sugar is not present, then the compounds have been referred to as the reverse pseudoaglycone of A, D, etc. A more preferred nomenclature is to refer to the pseudoaglycones as spinosyn A 17-Psa, spinosyn D 17-Psa, etc., and to the reverse pseudoaglycones as spinosyn A 9-Psa, spinosyn D 9-Psa, etc.

The naturally produced spinosyn compounds may be produced via fermentation from cultures NRRL 18395, 18537, 18538, 18539, 18719, 18720, 18743 and 18823. These cultures have been deposited and made part of the stock culture collection of the Midwest Area Northern Regional Research Center, Agricultural Research Service, United States Department of Agriculture, 1815 North University Street, Peoria, Ill., 61604.

U.S. Pat. No. 5,362,634 and corresponding European Patent Application No. 375316 A1 relate to spinosyns A, B, C, D, E, F, G, H, and J. These compounds are said to be produced by culturing a strain of the novel microorganism *Saccharopolyspora spinosa* selected from NRRL 18395, NRRL 18537, NRRL 18538, and NRRL 18539.

WO 93/09126 relates to spinosyns L, M, N, Q, R, S, and T. Also discussed therein are two spinosyn J producing strains: NRRL 18719 and NRRL 18720, and a strain that produces spinosyns Q, R, S, and T: NRRL 18823.

WO 94/20518 and U.S. Pat. No. 5,670,486 relate to spinosyns K, O, P, U, V, W, and Y, and derivatives thereof. Also discussed is spinosyn K-producing strain NRRL 18743.

A challenge in producing spinosyn compounds arises from the fact that a very large fermentation volume is required to produce a very small quantity of spinosyns. It is highly desired to increase spinosyn production efficiency and thereby increase availability of the spinosyns while reducing their cost.

Another challenge is the production of spinosyn compounds through methods that reduce or remove impurities while having no deleterious effect on spinosyn production levels.

BRIEF SUMMARY OF THE DISCLOSURE

A particular embodiment of the invention includes a method for producing a spinosyn producing strain that comprises modifying a nucleic acid molecule encoding for spinactin by introducing, mutating, deleting, replacing or inactivating a nucleic acid sequence encoding one or more activities encoded by said nucleic acid molecule. Such introduced, mutated, deleted, replaced or inactivated sequence can result in a nucleic acid molecule encoding a spinosyn that synthesizes a polyketide other than the polyketide synthesized from a native spinosyn producing strain. Another embodiment includes a host cell that includes a nucleic acid molecule encoding a modified spinosyn, wherein said molecule is obtained by the aforementioned method.

Another embodiment includes a method for producing a modified *Saccharopolyspora spinosa* organism. The method includes: providing a nucleic acid comprising a nucleotide sequence within the spinactin biosynthetic gene cluster of *S. spinosa*; mutating the nucleotide sequence; and introducing the nucleic acid comprising the mutated nucleotide sequence into a host *S. spinosa* organism, such that the nucleic acid is stably integrated into the genomic DNA of the host *S. spinosa* organism, thereby producing a modified *S. spinosa* organism, wherein a gene within the spinactin biosynthetic gene cluster no longer expresses a functional protein.

Certain embodiments include a method for producing a mixture of spinosyns. The method includes: providing a culture of at least one *Saccharopolyspora spinosa* organism comprising a means for disrupting spinactin biosynthesis; culturing at least one *S. spinosa* organism under fermentation conditions; and obtaining a mixture of spinosyns from the *S. spinosa* fermentation culture. In further embodiment, a method for producing spinosyns includes: providing a modified *Saccharopolyspora spinosa* organism made according to the aforementioned method; and culturing the organism under fermentation conditions, thereby producing at least one spinosyn.

Yet another embodiment is drawn to a compound having the formula (I):

(I)

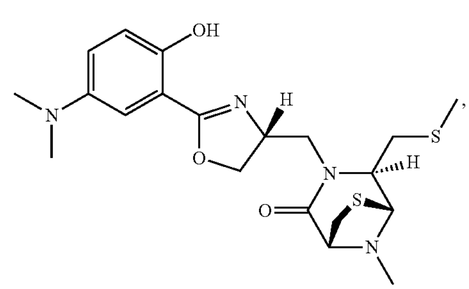

, or a salt or N-oxide thereof. In a particular embodiment, a method for isolating the compound of formula (I) includes: culturing *Saccharopolyspora spinosa* strain, NRRL 18395, under fermentation conditions; obtaining a technical material comprising secondary metabolites from the *S. spinosa* fermentation culture; forming a slurry of the technical material in a solution comprising methanol and water in equal amounts (1:1); and filtering the slurry, so as to form a filtrate comprising an enriched quantity of the compound; then separating compound (I) from the spinosyn factors by preparative liquid chromatography.

The foregoing and other features will become more apparent from the following detailed description of several embodiments, which proceeds with reference to the accompanying figures.

SEQUENCE LISTING

Figure 1:
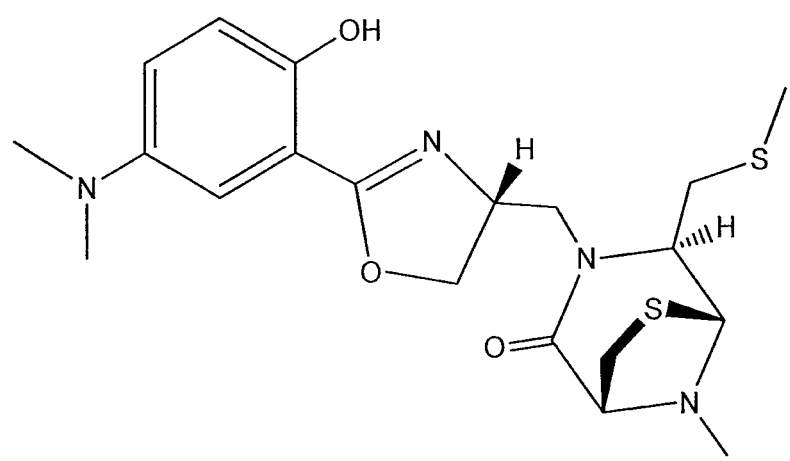
FIG. 1 includes a depiction of the chemical structure of spinactin.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NO:1 provides a polynucleotide sequence of contig 261 from the *S. spinosa* genome;

SEQ ID NO:2 provides a polynucleotide sequence of the NRPS1 gene;

SEQ ID NO:3 provides a polynucleotide sequence containing a fragment of 412 bp nucleotide sequence containing a fragment of the thiazolinyl imide reductase coding sequence;

SEQ ID NO:4 provides a polynucleotide sequence of a PCR amplification forward primer;

SEQ ID NO:5 provides a polynucleotide sequence of a PCR amplification reverse primer;

SEQ ID NO:6 provides a polynucleotide sequence of a fragment containing actinophage φC31 attachment site (attB) from *Streptomyces lividans*. The BamHI and NdeI restriction enzyme sites were added to the 5' and 3' ends, respectively;

SEQ ID NO:7 provides a polynucleotide sequence of forward primer2, a PCR amplification primer;

SEQ ID NO:8 provides a polynucleotide sequence of reverse primer2, a PCR amplification primer;

SEQ ID NO:9 provides a polynucleotide sequence of plasmid pCR8/GW/TOPO_aac(3)-attB;

SEQ ID NO:10 provides a polynucleotide sequence of forward primer3, PCR amplification primer, the underlined sequences hybridize with the aac(3)-attB cassette the non-underlined sequences are from the thiazolinyl imide reductase gene:

TCGACGGCCTGCTGCGCCGCATCCTCAACCAGCCGACA<u>ATGTAGGCTGGAGCTGCTTC</u>;

SEQ ID NO:11 provides a polynucleotide sequence of reverse primer3, PCR amplification primer, the underlined sequences hybridize with the aac(3)-attB cassette the non-underlined sequences are from the thiazolinyl imide reductase gene:

AACGCACCGCGCAGGCGCTGCGCGACGGATGGTTGAACA<u>CATATGGTCGACATGCCCGC</u>;

and

SEQ ID NO:12 provides a polynucleotide sequence of junction where the thiazolinyl imide reductase gene was deleted from cosmid clone 4G15 as confirmed by DNA sequencing.

DETAILED DESCRIPTION

Spinosyn biosynthetic genes and related ORFs were cloned and the DNA sequence of each was determined. The cloned genes and ORFs are designated hereinafter as spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa* epi, and *S. spinosa* kre.

*Saccharopolyspora spinosa* produces a mixture of nine closely related compounds collectively called "spinosyns." Within the mixture, spinosyn A and D, known as spinosad, are the major components and have the highest activity against key insect targets. Spinosyn J and L, two of the minor components within the spinosyn mixture, are the precursors for spinetoram, the second generation spinosyn insecticide.

Spinosad is an insecticide produced by Dow AgroSciences (Indianapolis, Ind.) that is comprised mainly of approximately 85% spinosyn A and approximately 15% spinosyn D. Spinosyn A and D are natural products produced by fermentation of *Saccharopolyspora spinosa*, as disclosed in U.S. Pat. No. 5,362,634. Spinosad is an active ingredient of several insecticidal formulations available commercially from Dow AgroSciences, including the TRACER™, SUCCESS™, SPINTOR™, and CONSERVE™ insect control products. For example, the TRACER product is comprised of about 44% to about 48% Spinosad (w/v), or about 4 pounds of Spinosad per gallon. Spinosyn compounds in granular and liquid formulations have established utility for the control of arachnids, nematodes, and insects, in particular *Lepidoptera*, *Thysanoptera*, and *Diptera* species. Spinosyn A and D is also referred to herein as Spinosyn A/D.

Spinetoram is a mixture of 5,6-dihydro-3'-ethoxy spinosyn J (major component) and 3'-ethoxy spinosyn L produced by Dow AgroSciences. The mixture can be prepared by ethoxylating a mixture of spinosyn J and spinosyn L, followed by hydrogenation. The 5,6 double bond of spinosyn J and its 3'-ethoxy is hydrogenated much more readily than that of spinosyn L and its 3'-ethoxy derivative, due to steric hindrance by the methyl group at C-5 in spinosyn L and its 3'-ethoxy derivative. See, U.S. Pat. No. 6,001,981. Spinosyn J and L is also referred to herein as Spinosyn J/L.

Novel spinosyns can also be produced by mutagenesis of the cloned genes, and substitution of the mutated genes for their unmutated counterparts in a spinosyn-producing organism. Mutagenesis may involve, for example: 1) deletion or inactivation of a ketoreductase, dehydratase or enoyl reductase (KR, DH, or ER) domain so that one or more of these functions is blocked and the strain produces a spinosyn having a lactone nucleus with a double bond, a hydroxyl group, or a keto group that is not present in the nucleus of spinosyn A (see Donadio et al., 1993); 2) replacement of an AT domain so that a different carboxylic acid is incorporated in the lactone nucleus (see Ruan et al., 1997); 3) addition of a KR, DH, or ER domain to an existing PKS module so that the strain produces a spinosyn having a lactone nucleus with a saturated bond, hydroxyl group, or double bond that is not present in the nucleus of spinosyn A; or 4) addition or subtraction of a complete PKS module so that the cyclic lactone nucleus has a greater or lesser number of carbon atoms. A hybrid PKS can be created by replacing the spinosyn PKS loading domain with heterologous PKS loading. See, e.g., U.S. Pat. No. 7,626,010. It has further been noted that spinosyns via modification of the sugars that are attached to the spinosyn lactone backbone can include modifications of the rhamnose and/or forosamine moiety or attachment of different deoxy sugars. The Salas group in Spain demonstrated that novel polyketide compounds can be produced by substituting the existing sugar molecule with different sugar molecules. Rodriguez et al. J. Mol. Microbiol Biotechnol. 2000 July; 2(3):271-6. The examples that follow throughout the application help to illustrate the use of mutagenesis to produce a spinosyn with modified functionality.

The DNA from the spinosyn gene cluster region can be used as a hybridization probe to identify homologous sequences. Thus, the DNA cloned here could be used to locate additional plasmids from the *Saccharopolyspora spinosa* gene libraries which overlap the region described here but also contain previously uncloned DNA from adjacent regions in the genome of *Saccharopolyspora spinosa*. In addition, DNA from the region cloned here may be used to identify non-identical but similar sequences in other organisms. Hybridization probes are normally at least about 20 bases long and are labeled to permit detection.

According to a particular embodiment of the invention, a method for producing a spinosyn producing strain comprises modifying a nucleic acid molecule encoding for spinactin by introducing, mutating, deleting, replacing or inactivating a nucleic acid sequence encoding one or more activities encoded by said nucleic acid molecule. Such introduced, mutated, deleted, replaced or inactivated sequence can result in a nucleic acid molecule encoding a spinosyn that synthesizes a polyketide other than the polyketide synthesized from a native spinosyn producing strain. The spinosyn producing strain may produce spinosyns A and D, and in particular embodiments, may produce spinosyns J and L.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 Overview of principles of hybridization and the strategy of nucleic acid probe assays, Elsevier, N.Y. Generally, highly stringent hybridization and wash conditions are selected to be about 5° C. lower than the thermal melting point ($T_m$) for the specific sequence at a defined ionic strength and pH. The $T_m$, is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC (sodium chloride/sodium citrate buffer) wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The invention also relates to an isolated polynucleotide hybridizable under stringent conditions, preferably under highly stringent conditions, to a polynucleotide as of the present invention.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in this application or the complement thereof.

Another non-limiting example of stringent hybridization conditions is hybridization in 6×SSC at about 45° C., followed by one or more washes in 1×SSC, 0.1% SDS at 50° C., preferably at 55° C. more preferably at 60° C. and even more preferably at 65° C.

Highly stringent conditions can include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

In some embodiments an isolated nucleic acid molecule of the invention that hybridizes under highly stringent conditions to a nucleotide sequence of the invention can correspond to a naturally occurring nucleic acid molecule. As used herein, a "naturally occurring" nucleic acid molecule refers to an RNA or DNA molecule having a nucleotide sequence that occurs in nature (e.g., encodes a natural protein).

A skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

"Functional polymorphism" as used herein refers to a change in the base pair sequence of a gene that produces a qualitative or quantitative change in the activity of the protein encoded by that gene (e.g., a change in specificity of activity; a change in level of activity). The term "functional polymorphism" includes mutations, deletions and insertions.

In general, the step of detecting the polymorphism of interest may be carried out by collecting a biological sample containing DNA from the source, and then determining the presence or absence of DNA containing the polymorphism of interest in the biological sample.

Determining the presence or absence of DNA encoding a particular mutation may be carried out with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques). Further, the detecting step may include the step of detecting whether the subject is heterozygous or homozygous for the particular mutation. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al.

Amplification of a selected, or target, nucleic acid sequence may be carried out by any suitable means. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad. Sci. USA 86, 1173-1177 (1989)), self-sustained sequence replication (or "3SR") (see J. Guatelli et al., Proc. Natl. Acad. Sci. USA 87, 1874-1878 (1990)), the QI3 replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. Such probes may be from 5 to 500 nucleotides in length, preferably 5 to 250, more preferably 5 to 100 or 5 to 50 nucleic acids. When PCR conditions allow for amplification of all allelic types, the types can be distinguished by hybridization with an allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available on the interne at the accelrys website, more specifically at _accelrys(dot)com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available on the internet at the accelrys website, more specifically at _accelrys(dot)com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available on the internet at the vega website, more specifically ALIGN-IGH Montpellier, or more specifically at _vega(dot)igh(dot)cnrs(dot)fr/bin/align-guess(dot)cgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. (Available on the internet at the ncbi website, more specifically at _ncbi(dot)nlm(dot)nih(dot)gov).

Another embodiment may include a host cell that comprises a nucleic acid molecule encoding a modified spinosyn, wherein said molecule is obtained by the aforementioned method. An alternative method may also produce a modified polyketide causing expression of a nucleic acid molecule in a host cell, which polyketide may also be further purified. In a particular embodiment, mutating, deleting, replacing or inactivating a sequence may comprise: providing a library of nucleic acids, which nucleic acids comprise one or more polynucleotide segments operably linked to at least one transcription regulatory sequence; introducing the library of nucleic acids into a population of recipient cells or intracellular organelles, whereby said nucleic acids disable spinactin production while maintaining spinosyn production; and identifying at least one recipient cell, intracellular organelle or organism comprising a recipient cell, with a desired phenotype, thereby controlling the spinosyn producing strain. Mutating the nucleotide sequence may include introducing a deletion, a mutation, or a stop codon. The nucleotide sequence may comprised within a gene that can be selected from the group consisting of: ABC transporter substrate-binding protein; amino acid ABC transporter permease; EmrB QacA family drug resistance transporter; monooxygenase; NRPS1; NRPS2; a gene located between NRPS1 and NRPS2 in the *S. spinosa* genome; thiazolinyl imide reductase; thioesterase; methyltransferase; pabAB; a transcriptional regulator; Acyl-CoA synthase; N-methyltransferase; pyridoxamine 5'-phosphate oxidase; 2,3-dihydrobenzoate-AMP ligase; and aminotransferase. The nucleotide sequence within the thiazolinyl imide reductase gene may be at least 80% identical to SEQ ID NO:3.

The modified *S. spinosa* organism can produce less spinactin than was produced in the host *S. spinosa* organism before introduction of the nucleic acid, or may produce no spinactin. In some embodiments, the modified *S. spinosa* organism can produce: an amount of spinosyn A that is substantially identical to the amount of spinosyn A produced in the host *S. spinosa* organism before introduction of the nucleic acid; an amount of spinosyn D that is substantially identical to the amount of spinosyn D produced in the host *S. spinosa* organism before introduction of the nucleic acid, and an amount of spinactin that is less than the amount of spinactin produced in the host *S. spinosa* organism before introduction of the nucleic acid.

A method for producing a mixture of spinosyns, the method comprising: providing a culture of at least one *Saccharopolyspora spinosa* organism comprising a means for disrupting spinactin biosynthesis; culturing at least one *S. spinosa* organism under fermentation conditions; and obtaining a mixture of spinosyns from the *S. spinosa* fermentation culture. Disrupting spinactin biosynthesis may be accomplished by inactivating a gene of the spinactin gene cluster or by mutating a gene in the spinactin gene cluster. The mixture of spinosyns obtained from the *S. spinosa* fermentation culture may include at least one of spinosyn A and spinosyn D. The mixture of spinosyns obtained from the *S. spinosa* fermentation culture may include no spinactin. In some embodiments, the gene of the spinactin gene cluster is a thiazolinyl imide reductase gene. A modified *Saccharopolyspora spinosa* organism may be produced by the method. The organism may include a transgene involved in spinosyn biosynthesis. The modified *S. spinosa* organism may include a transgene involved in spinosyn biosynthesis that is stably integrated into the genomic DNA of the organism at a site wherein the nucleic acid was stably integrated.

Another embodiment of the invention includes a modified *Saccharopolyspora spinosa* organism comprising a means for disrupting spinactin synthesis, wherein the organism is capable of producing spinosyn A and/or spinosyn D without producing a significant amount of spinactin.

Another embodiment includes a method for producing a modified *Saccharopolyspora spinosa* organism. The method includes: providing a nucleic acid comprising a nucleotide sequence within the spinactin biosynthetic gene cluster of *S. spinosa*; mutating the nucleotide sequence; and introducing the nucleic acid comprising the mutated nucleotide sequence into a host *S. spinosa* organism, such that the nucleic acid is stably integrated into the genomic DNA of the host *S. spinosa* organism, thereby producing a modified *S. spinosa* organism, wherein a gene within the spinactin biosynthetic gene cluster no longer expresses a functional protein.

In further embodiment, a method for producing spinosyns includes: providing a modified *Saccharopolyspora spinosa* organism made according to the aforementioned method; and culturing the organism under fermentation conditions, thereby producing at least one spinosyn.

Yet another embodiment is drawn to a compound having the formula (I):

(I)

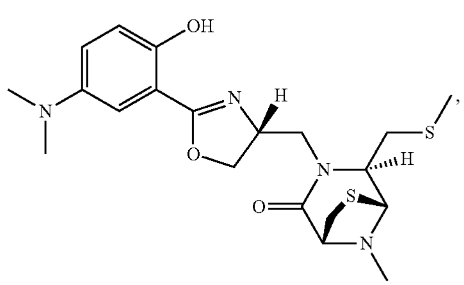

or a salt or N-oxide thereof. In a particular embodiment, a method for isolating the compound of formula (I) includes: culturing *Saccharopolyspora spinosa* strain, NRRL 18395, under fermentation conditions; obtaining a technical material comprising secondary metabolites from the *S. spinosa* fermentation culture; forming a slurry of the technical material in a solution comprising methanol and water in equal amounts (1:1); and filtering the slurry, so as to form a filtrate comprising an enriched quantity of the compound.

The following examples are provided to illustrate certain particular features and/or embodiments. The examples should not be construed to limit the disclosure to the particular features or embodiments exemplified.

EXAMPLES

Example 1

The Identification and Characterization of the Spinactin Molecule from *S. Spinosa*

Spinactin is a sulfur-containing compound which was identified from an *S. spinosa* fermentation culture. FIG. 1 illustrates the chemical structure of spinactin. This structure was determined using NMR spectroscopy and verified with X-ray crystallography. See FIG. 2.

A fermentation culture of *S. spinosa* from strain NRRL 18395 was propagated using the fermentation protocol described in Strobel and Nakatsukasa (1993) J. Ind. Microbiol. Biotechnol. 11(2):121-7. Liquid chromatographic analysis identified the presence of a previously undetected secondary metabolite having a characteristic UV spectrum, with $\lambda_{max}$=227 and 358 nm. The secondary metabolite was isolated using the following procedure. The technical material (3 kg) from a *S. spinosa* fermentation culture was slurried in methanol/water (1:1) and filtered. The filtrate was found to contain an enriched quantity of the previously undetected secondary metabolite. This secondary metabolite was separated from the remaining spinosyn material via preparative reverse phase liquid chromatography. Using this method, 6 gm of the new molecule was obtained, which accounted for about 0.02% by mass of the total technical material. The new molecule, which was named spinactin, was re-crystallized from methanol/water as a pale green solid (mp 79° C.). High resolution probe electron impact mass spectrometry (EI/MS) indicated that spinactin possessed a molecular formula of $C_{20}H_{28}N_4O_3S_2$. Analysis of $^1H$, $^{13}C$ and Distortionless Enhancement by Polarization Transfer (DEPT) spectra indicated the presence of a dimethylamine group, a second methylamine, and a single S-methyl group. Also apparent was a 1,2,4-trisubstituted benzene ring. The remainder of the spectrum in chloroform included complex non-first order multiplets including virtual coupling effects seen in 2-D spectra, caused by the coincident chemical shifts for 4-H and 5-H. Thus the structure was solved in methanol-d4 in which the spectrum was first-order as described below using standard 2-D NMR techniques including COSY, HSQC, and HMBC (see Table 1).

Three spin systems were readily identified in the $^1H$ spectrum; three aromatic multiplets were detected between 7.3 and 6.7 ppm, indicating a 1,2,4-trisubstituted benzene ring containing oxygen or nitrogen substituents; another spin-system of two methylenes (one oxygen substituted, and one with nitrogen) sandwiching a methine, which also indicated nitrogen substitution; and an elongated spin-system containing three contiguous methines, with methylenes at the termini. None of the multiplets resonated at higher field than 2.5 ppm indicating a high degree of heteroatom substitution. Aside from these spin systems, there were three methyl singlets, which were shown to be a dimethyl amino group, and another N-methyl group, and a methyl thioether. The coupling constant between two of the methines was small, suggesting that the carbon atoms were not directly connected. Both of these carbon atoms had HMBC cross-peaks from the N-methyl group, indicating that they were on either side of a methylated tertiary nitrogen.

The molecule was assembled by extensive analysis of the HMBC experiments. Thus an oxazoline ring was identified with attachment to the aromatic ring at C-2. This ring was determined to have a methylene group attached to C-5, which was used as a handle to aid in the assembly of the diazabicyclooctane ring system. This methylene (resonating at 3.9 and 3.5 ppm) indicated cross-peaks to one of the methines in the extended spin system (63 ppm), and also to an amide carbonyl at 172 ppm. Further cross peaks to this carbonyl came from another methine (4.1 ppm) and one of the other methylene groups (resonating at 3.5 and 3.2 ppm) indicating a 6-membered ring containing 2 nitrogen atoms. That this methylene was bridged back into the ring, was determined by the existence of cross-peaks to both of the methines connected to the methylated nitrogen atom, the thioether deduced by chemical shift. Assembly of the rest of the molecule was readily accomplished once this ring system was determined.

TABLE 1

NMR Spectrum of spinactin in MeOH.

| No. | $^1$H | $^{13}$C |
|---|---|---|
| 2 | — | 167.8 |
| 4 | 4.54, dd (8.7, 9.6) | 71.3 |
|   | 4.22, t (8.1) |   |
| 5 | 4.65, m | 65.8 |
| 6 | 3.86, dd (14.4, 7.0) | 46.6 |
|   | 3.53, dd (14.4, 4.5) |   |
| 8 | 4.02, ddd (10.6, 4.3, 4.3) | 62.7 |
| 9 | 5.11, dd (3.5, 1.6) | 78.3 |
| 11 | 4.09, dd (5.6, 1.3) | 71.5 |
| 12 | — | 172.7 |
| 13 | 3.22, dd (5.8, 10.7) | 34.5 |
|    | 3.53, d (10.7) |   |
| 14 | 3.15, dd (12.9, 4.3) | 35.9 |
|    | 2.79, dd (12.9, 4.3) |   |
| 15 | 2.15, s | 16.0 |
| 16 | 2.40, s | 40.0 |
| 1' | — | 154.0 |
| 2' | — | 111.4 |
| 3' | 7.14, d (3.1) | 114.1 |
| 4' | — | 145.7 |
| 5' | 7.08, dd (9.0, 3.1) | 122.9 |
| 6' | 6.90, d (9.0) | 118.2 |
| NMe$_2$ | 2.86, s | 42.6 |

Figure 2:
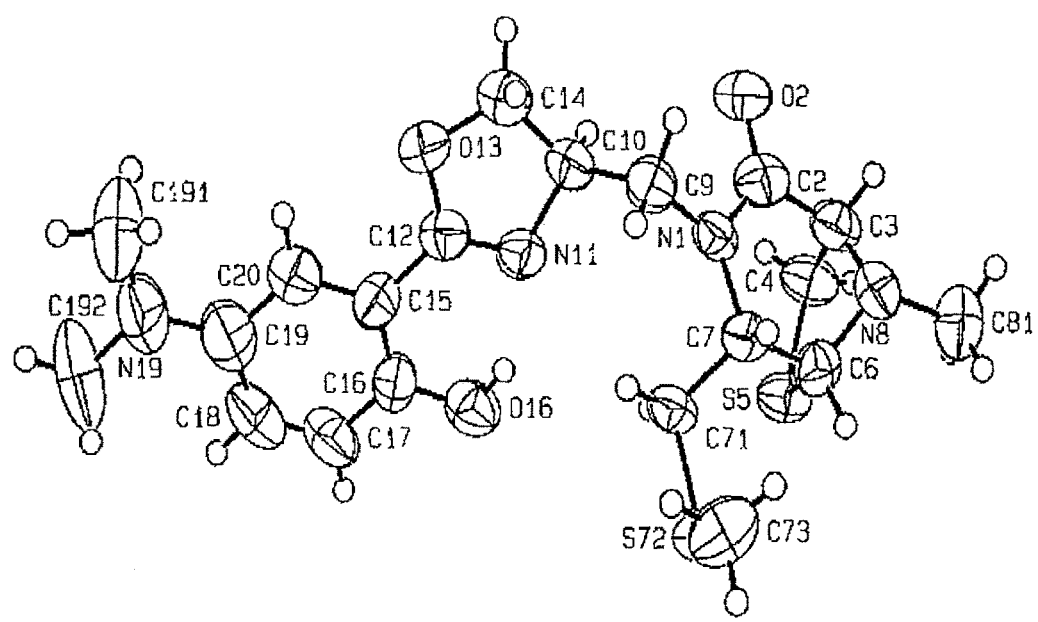
FIG. 2 includes the Oak Ridge Thermal Ellipsoid Plot Program (ORTEP) molecular modeling diagram for spinactin as determined from X-ray crystallography data.

An X-ray crystallography method was used to validate the structure of the spinactin molecule. An ORTEP (Oak Ridge Thermal Ellipsoid Program) model of the structure is shown in FIG. 2. A single crystal of spinactin (MP 79° C.) with dimensions 0.50×0.8×0.06 mm was irradiated with Mo K$_a$ radiation on a Nonius Kappa CCD X-ray diffractometer (Bruker-Noninus, Madison, Wis.). A total of 7,801 reflections were collected (of which 2,276 were unique). The data was refined and solved using standard methods and utilizing the data analysis programs SHELXS97 and SIR97.

Example 2

Identification and Characterization of the Spinactin Biosynthetic Gene Cluster

Figure 3:
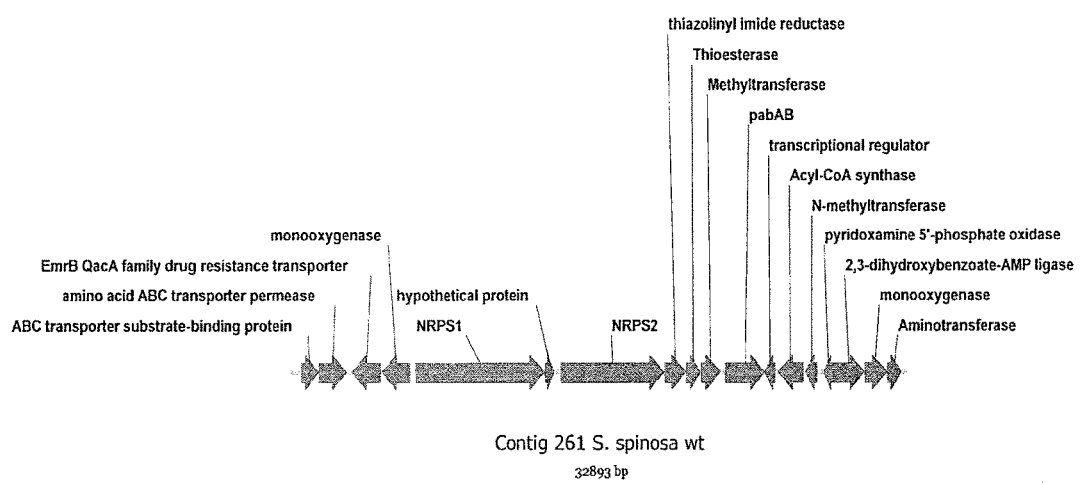
FIG. 3 includes an annotated physical map of the identified putative spinactin gene cluster from contig 261 from *S. spinosa* strain NRRL18395 genomic sequence.

Based on the structural resemblance of the 2-hydroxyphenyloxazoline moiety of spinactin as compared to the 2-hydroxyphenyloxazoline moiety of mycobactin A, it was hypothesized that both molecules are produced by similar biosynthetic pathways. The involvement of the mycobactin A biosynthetic gene cluster and the phenyloxazoline synthase mbtB gene (mbtB) in the biosynthesis of the 2-hydroxyphenyloxazoline moiety of mycobactin A was characterized in Quadri et al. (1998) 5:631-645. The amino acid sequence of phenyloxazoline synthase mbtB (Accession No: ZP_06505539) from the mycobactin gene cluster of *Mycobacterium tuberculosis* strain 02_1987 was used to screen, in silico, the genomic sequence obtained from the *S. spinosa* wild type strain (NRRL 18395). The resulting BLAST search identified the presence of a putative gene sequence from the *S. spinosa* genome which encoded an amino acid sequence with similarity to MbtB. The NRPS1 gene from the *S. spinosa* genome shared approximately 46% identity at the amino acid level with the mbtB gene from the *M. tuberculosis* gene cluster. The identification of this gene led to the subsequent identification of a *S. spinosa* gene cluster which contains additional genes that are proposed to be involved in the biosynthesis of spinactin. These gene sequences from the *S. spinosa* spinactin gene cluster were annotated using the computer program, FgenesB (Cambridge University, UK). FIG. 3 shows an annotation of the polynucleotide sequence for contig 261, which contains the NRPS1 gene sequence from the *S. spinosa* genomic sequence, the polynucleotide sequence for contig 261 is listed as SEQ ID NO:1. The polynucleotide sequence of NRPS1 is listed as SEQ ID NO:2.

Example 3

Screening and Identification of Cosmid Clones Containing the Spinactin Gene Cluster from a *S. spinosa* Genomic Cosmid Library A genomic cosmid library from *S. spinosa* (U.S. patent application Ser. No. 13/100,202) was screened to identify cosmid clones which contained the thiazolinyl imide reductase gene. The thiazolinyl imide reductase gene is located downstream of the NRPS1 gene, and was characterized as a putative member of the spinactin gene cluster which encodes an enzyme that is non-essential for the biosynthesis of spinosyn A/D. This gene was used to identify cosmid clones that could be modified by deleting a 7.6 Kb fragment which contains the spinactin gene cluster. The resulting cosmid clones were then used to generate *S. spinosa* knock-out strains.

Figure 4:
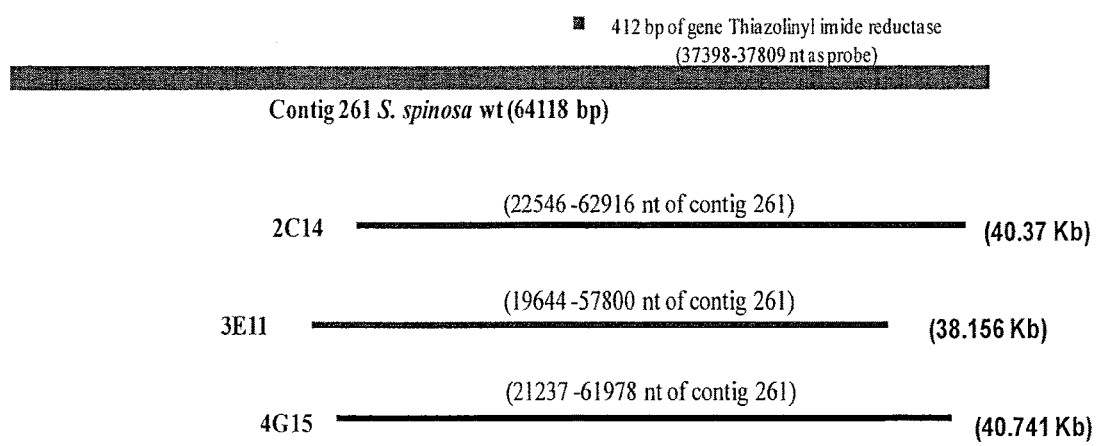
FIG. 4 includes an illustration of contig 261 consisting of the putative spinactin gene cluster from the *S. spinosa* genomic sequence that is shown in relation to the identified three cosmid clones with their respective insert sizes. The location of the partial fragment of thiazolinyl imide reductase that served as a probe in the screening strategy is shown.

A 412 bp fragment of the thiazolinyl imide reductase gene was prepared with a PCR digoxigenin (DIG) labeling kit. The 412 bp (SEQ ID NO:3) fragment was PCR amplified using a forward primer (SEQ ID NO:4) and a reverse primer (SEQ ID NO:5). Hybridization was completed at 42° C. in commercially supplied hybridization buffer (Roche) overnight. The nylon membranes were washed under stringent conditions for 5 minutes, twice in 2×SSC, 0.1% SDS at room temperature and for 15 minutes, twice in 0.1×SSC, 0.1% SDS at 68° C. Chemiluminescent labeling and detection was carried out by using the DIG Luminescent Detection Kit™ (Roche). Three positive cosmid clones were identified (2C14, 3E11 and 4G15) and confirmed by end-sequencing of the cosmid insert using T3 and T7 sequencing primers. FIG. 4 summarizes the details of the three identified cosmid clones and their respective fragment insert sizes and location corresponding to contig 261 and the 412 bp fragment of the thiazolinyl imide reductase gene from the genomic sequence of *S. spinosa*.

Example 4

Construction of an Apramycin Resistance Gene Cassette with an attB Attachment Site for Partial Deletion of the Spinactin Gene Cluster The construction of an apramycin-attB cassette was completed by cloning the attB sequence into an apramycin resistance gene cassette. Synthesis of the *Streptomyces lividans*, actinophage φC31 attachment site sequence (attB; Accession No: X60952) was carried out by a third party service provider (Integrated DNA Technologies, Coralville, Iowa). To facilitate the cloning of the synthesized attB fragment, BamHI and NdeI sites were added to the 5' and 3' ends, respectively (SEQ ID NO:6). The vector which contained the synthesized attB sequence was labeled as pIDTSMART.

Template plasmid, pIJ773 (Accession No: AX657063), containing the apramycin resistance gene cassette, aac(3)-IV (Accession No: X99313), and the oriT of plasmid RP4 (Accession No: L27758), flanked by FRT sites was PCR-amplified using a forward primer2 (SEQ ID NO:7) and a reverse primer2 (SEQ ID NO:8). The PCR fragment was cloned into the pCR8/GW/TOPO™ vector (Invitrogen, Carlsbad, Calif.) as instructed by the manufacturer's protocol, and the presence and integrity of the inserted apramycin cassette was confirmed via restriction digestion and sequencing.

Figure 5:
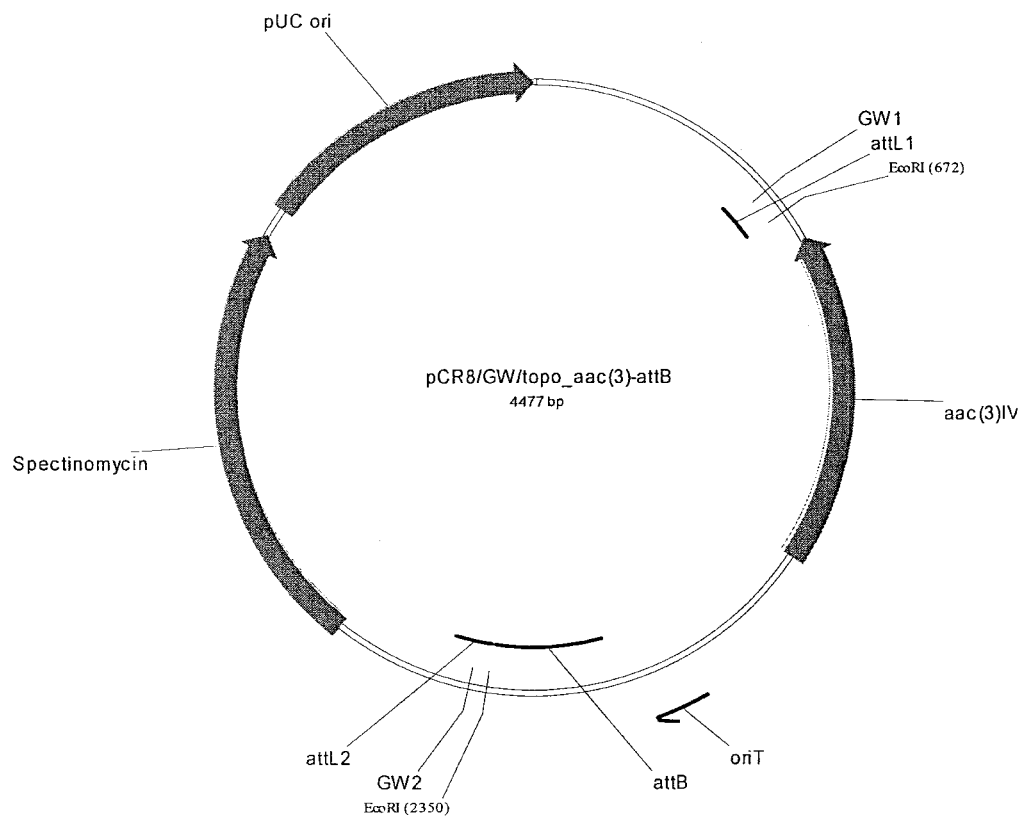
FIG. 5 includes an illustration of plasmid map of pCR8/GW/Topo_aac(3)-attB.

The attB fragment from pIDTSMART was digested with BamHI and NdeI and the resulting 300 bp DNA fragment was gel-purified using the QIAquick Gel Extraction Kit™ (Qiagen, Valencia, Calif.). The purified attB fragment was cloned into the pCR8/GW/TOPO™ vector, which contained the apramycin resistance gene cassette at the NdeI and BamHJ restriction sites, using standard molecular biological techniques. The construction of a new apramycin resistance gene cassette containing an attB attachment site was confirmed by restriction enzyme digestion and sequencing. The constructed pCR8/GW/TOPO_aac(3)-attB plasmid map and sequence are provided as FIG. 5 (SEQ ID NO:9).

Example 5

Generation of S. Spinosa Knock-Out Strains Containing a Partial Deletion of the Spinactin Gene Cluster A 7.6 Kb deletion of the spinactin gene cluster was achieved by targeting the thiazolinyl imide reductase region with a apramycin-attB cassette using the Redirect Recombineering Technology™ (Gust et al. (2003) Proc. Natl. Acad. Sci. USA 100(4):1541-6). A set of primers were designed to amplify the apramycin-attB cassette using forward primer3 (SEQ ID NO:10) and reverse primer3 (SEQ ID NO:11). These primers were designed to contain 5' sequences which shared homology to the spinactin gene cluster. The resulting PCR product was integrated into cosmid clone 4G15 by following the Redirect Recombineering protocol. A knock-out of the spinactin gene cluster within cosmid clone 4G15 resulted via a double cross over, wherein the apramycin-attB cassette replaced the native DNA sequence of cosmid clone 4G15. The resulting deletion was confirmed via DNA sequencing of the junction region. The nucleotide sequence of the junction, wherein the 7.6 Kb fragment of the spinactin gene cluster was deleted, is provided as SEQ ID NO:12.

The modified 4G15 cosmid DNA was isolated and transformed into a donor strain of E. coli, S17-1, and used in a conjugation experiment with S. spinosa strain NRRL 18538. The conjugation was completed following a protocol which had been modified to include ISP4-medium (Matsushima et al. (1994) Gene 146(1):39-45). Transconjugants were selected by flooding the conjugation media-plates with apramycin (50 µg/ml) and nalidixic acid (25 µg/ml). The transconjugants from the conjugation plates were patched onto ISP2 agar medium supplemented with 20 mM $CaCl_2$ and apramycin (50 µg/ml) and nalidixic acid (25 µg/ml). The double cross-over knock-outs (resistant to apramycin and sensitive to kanamycin antibiotics) were selected on ISP2 agar medium containing apramycin at 50 µg/ml.

Figure 6:
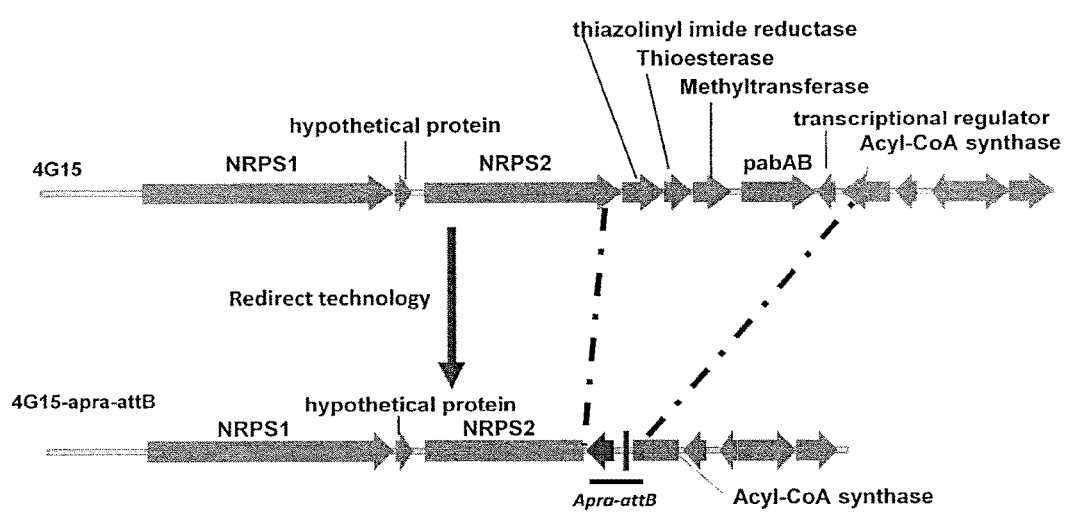
FIG. 6 includes an illustration of the deletion of a 7.6 kb fragment from the spinactin gene cluster in cosmid clone 4G15 which was produced using the Redirect Recombineering Technology™.

Five independent knock-out strains (labeled as 538-M2, 538-M4, 538-M6, 538-M7 and 538-M10) were selected. These knock-out strains were molecularly confirmed for the 7.6 Kb deletion of the spinactin gene cluster by PCR amplification. The PCR reactions produced a fragment of the expected size which indicated that a 7.6 Kb fragment was deleted from the genome of S. spinosa strain NRRL 18538 (See FIG. 6). Having confirmed the S. spinosa NRRL 18538 knock-out strains via phenotypic and genotypic assays, the strains were propagated as shake flask fermentation cultures and the spinosyn A and D production titers were quantitated.

Example 6

Spinosyn A and D Production and Confirmation of Abolishment of Spinactin Production in S. spinosa Strain NRRL 18538 Knock-Out Strains The knock-out strains derived from S. spinosa strain NRRL 18538, which were generated to contain a partial deletion of the spinactin gene cluster, were propagated as 6-day and 10-day shake flask fermentation cultures. The knock-out strains produced levels of spinosyn A and D comparable to the control strains that contained an intact spinactin gene cluster. Moreover, undetectable or very low levels of spinactin were detected in the S. spinosa NRRL 18538 knock-out strains. These results indicate that the removal of the secondary metabolite, spinactin, does not deleteriously affect the production and biosynthesis of spinosyns A and D.

Methanol extracts of the fermentation broth from wild-type S. spinosa strain NRRL 18538 and S. spinosa strain NRRL 18538 knock-out strains were analyzed for spinactin production using a LC-UV-MS method. The methanol extraction protocol was completed wherein one part of fermentation broth and three parts of methanol were incubated overnight at room temperature. Samples of the methanol extracts were chromatographed using an Agilent Eclipse Plus C18 (100×3 mm; 1.8 µm) column at 40° C. eluted at 0.5 mL/min using a linear gradient of A:B 50:50 (0 min) to 5:95 (12 mM) where A=25 mM ammonium acetate and B=acetonitrile-methanol (80:20). Spinactin, which eluted at approximately 8.8 mM, was detected either by UV absorbance at 227 nm or by selected ion monitoring mass spectrometry (SIM-MS), monitoring the ion at m/z 437.2. Quantitation was performed using an external standard method with calibration curves established from a pure sample of spinactin. In the wild-type S. spinosa strain NRRL 18538 and S. spinosa strain NRRL 18538 knock-out strains, the UV method was used for quantitation of spinactin when present above approximately 2 mg/L, whereas the SIM-MS method was used when the compound was present in the range approximately 0.02-2 mg/L.

The resulting spinosyn A and D and spinactin titers for the fermentation broth from wild-type S. spinosa strain NRRL 18538 and S. spinosa strain NRRL 18538 knock-out strains are summarized in Table 2. These data demonstrate that a partial gene deletion within the spinactin gene cluster had no effect on the titer of spinosyn production in the S. spinosa strain NRRL 18538 knock-out strains as compared to the wild-type S. spinosa strain NRRL 18538.

TABLE 2

Summary of HPLC analysis of methanol extracts from 6-day and 10-day fermentation broth of wild-type S. spinosa strain NRRL 18538 listed as "538" and S. spinosa NRRL 18538 knock-out strains listed as "538-M2," "538-M4," "538-M6," "538-M7," and "538-M10."

| | | Compound Titer mg/L | | | |
| --- | --- | --- | --- | --- | --- |
| Day | Strain | spin A | spin D | Total (spinA/spinD) | spinactin |
| 6 | 538 | 232.05 | 23.70 | 255.75 | 0.23 |
| 6 | 538-M2 | 269.68 | 31.96 | 301.64 | 0.11 |
| 6 | 538-M4 | 222.17 | 26.41 | 248.58 | 0.00 |
| 6 | 538-M6 | 265.62 | 33.57 | 299.19 | 0.00 |
| 6 | 538-M7 | 233.58 | 29.75 | 263.43 | 0.00 |
| 6 | 538-M10 | 274.41 | 35.38 | 309.79 | 0.13 |
| 10 | 538 | 213.18 | 33.87 | 247.04 | 5.36 |

TABLE 2-continued

Summary of HPLC analysis of methanol extracts from 6-day and 10-day fermentation broth of wild-type *S. spinosa* strain NRRL 18538 listed as "538" and *S. spinosa* NRRL 18538 knock-out strains listed as "538-M2," "538-M4," "538-M6," "538-M7," and "538-M10."

| Day | Strain | Compound Titer mg/L | | | |
|---|---|---|---|---|---|
| | | spin A | spin D | Total (spinA/spinD) | spinactin |
| 10 | 538-M2 | 186.93 | 27.03 | 213.95 | 0.14 |
| 10 | 538-M4 | 184.25 | 31.42 | 215.67 | 0.00 |
| 10 | 538-M6 | 258.14 | 45.06 | 303.20 | 0.09 |
| 10 | 538-M7 | 239.61 | 43.79 | 283.40 | 0.00 |
| 10 | 538-M10 | 145.07 | 27.46 | 172.53 | 0.08 |

An approximately 7.6 kb fragment of the spinactin biosynthetic gene cluster coding sequence including the thiazolinyl imide reductase gene was deleted, thereby abolishing spinactin production in *S. spinosa* strain NRRL 18538. Subsequent fermentation of the knock-out strains resulted in biosynthesis of spinosyns A and D at levels that were comparable to *S. spinosa* control strains. Therefore, the deletion of the 7.6 kb fragment from the spinactin biosynthetic gene cluster in *S. spinosa* strain NRRL 18538 resulted in the removal of the secondary metabolite, spinactin, from the felinentation culture without deleteriously effecting the production and biosynthesis of spinosyns A and D.

What may be claimed is:

1. A method for producing a modified spinosvn-producing host cell, the method comprising:
   identifying, in a spinosvn-producing host cell, a spinactin gene cluster comprising a thiazolinyl imide reductase gene comprising a polynucleotide that is at least 80% identical to SEQ ID NO:3; and
   knocking out the thiazolinyl imide reductase gene in the spinactin gene cluster by introducing a deletion or a stop codon into the gene, in the spinosvn-producing host cell, to produce the modified spinosyn-producing cell,
   wherein the modified spinosvn-producing host cell synthesizes a type and/or amount of polyketide different from the type and/or amount of polyketide that is synthesized from the spinosvn-producing host cell.

2. The method of claim 1, wherein the modified spinosvn-producing host cell produces spinosyn A and D, but does not produce spinactin.

3. The method of claim 1, wherein the modified spinosvn-producing host cell produces:
   an amount of spinosyn A that is substantially identical to the amount of spinosyn A produced in the spinosvn-producing host cell before the spinosvn-producing host cell was modified,
   an amount of spinosyn D that is substantially identical to the amount of spinosyn D produced in the spinosvn-producing host cell before spinosvn-producing host cell was modified, and
   an amount of spinactin that is less than the amount of spinactin produced in the spinosvn-producing host cell before the spinosvn-producing host cell was modified.

4. A method for producing a mixture of spinosyns, the method comprising:
   providing a culture of at least one modified spinosvn-producing host cell produced by the method of claim 1;
   culturing the at least one modified spinosvn-producing host cell under fermentation conditions; and
   obtaining a mixture of spinosyns from the fermentation culture.

5. The method of claim 4, wherein the mixture of spinosyns obtained from the fermentation culture comprises at least one of spinosyn A and spinosyn D.

6. The method of claim 4, wherein the mixture of spinosyns obtained from the fermentation culture comprises no spinactin.

* * * * *